US006161932A

United States Patent [19]

Goto et al.

[11] Patent Number: 6,161,932

[45] Date of Patent: Dec. 19, 2000

[54] VISUAL AXIS INPUT AND DECISION TRANSFER DEVICE AND METHOD

[75] Inventors: Hironori Goto; Masaaki Yoshida, both of Tokyo, Japan

[73] Assignee: Canon Kabushiki Kaisha, Tokyo, Japan

[21] Appl. No.: 09/265,587

[22] Filed: Mar. 10, 1999

[30] Foreign Application Priority Data

Mar. 13, 1998 [JP] Japan ................................ 10-082925

[51] Int. Cl.[7] ................................ A61B 3/14

[52] U.S. Cl. ................................ 351/208

[58] Field of Search ................................ 351/204, 201, 351/208, 209, 246; 396/51; 345/7; 382/117; 348/333

[56] References Cited

U.S. PATENT DOCUMENTS

| | | | |
|---|---|---|---|
| 4,595,990 | 6/1986 | Garwin et al. | 364/518 |
| 4,973,149 | 11/1990 | Hutchinson | 351/210 |
| 5,689,619 | 11/1997 | Smyth | 395/10 |
| 5,694,623 | 12/1997 | Akashi | 396/51 |
| 5,717,413 | 2/1998 | Mizouchi | 345/7 |

FOREIGN PATENT DOCUMENTS 2 281 838 3/1995 United Kingdom .

*Primary Examiner*—George Manuel
*Attorney, Agent, or Firm*—Fitzpatrick, Cella, Harper & Scinto

[57] ABSTRACT

A visual axis input and decision transfer device operates so that when a detection-result condition, such as a visual-axis-detection success or failure, blinking, selecting of the same choice, or the like is judged based on visual-point-position data, and a user is notified of detection-result information indicating the detection-result condition in response to a judgment result by changing a selection frame color of characters, the user can confirm the detection result of the visual axis, and is prevented from repeating wasteful operations many times.

42 Claims, 32 Drawing Sheets

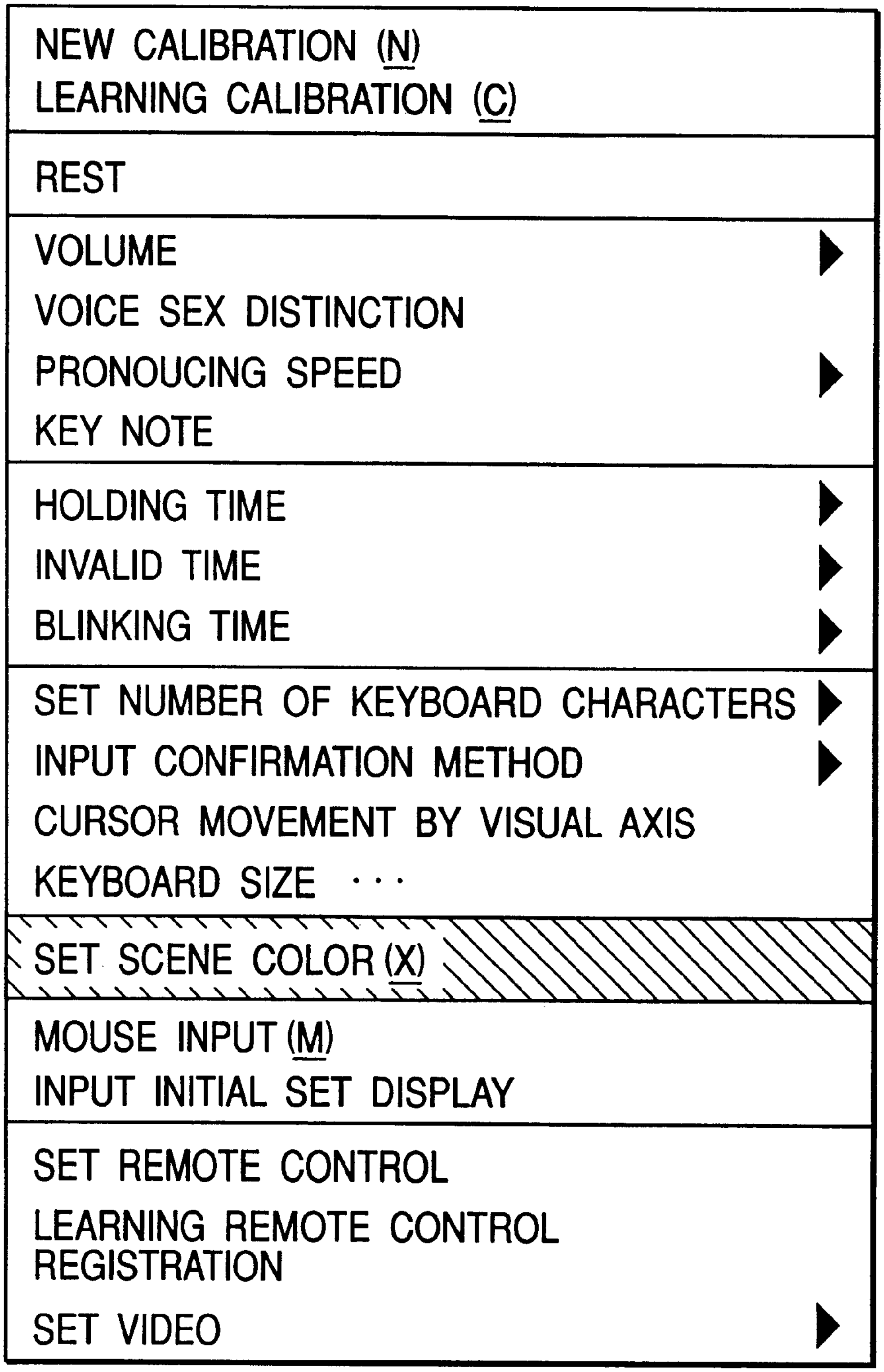

FIG. 21

| |
|---|
| NEW CALIBRATION (N) |
| LEARNING CALIBRATION (C) |
| REST |
| VOLUME ▶ |
| VOICE SEX DISTINCTION |
| PRONOUCING SPEED ▶ |
| KEY NOTE |
| HOLDING TIME ▶ |
| INVALID TIME ▶ |
| BLINKING TIME ▶ |
| SET NUMBER OF KEYBOARD CHARACTERS ▶ |
| INPUT CONFIRMATION METHOD ▶ |
| CURSOR MOVEMENT BY VISUAL AXIS |
| KEYBOARD SIZE ··· |
| SET SCENE COLOR (X) |
| MOUSE INPUT (M) |
| INPUT INITIAL SET DISPLAY |
| SET REMOTE CONTROL |
| LEARNING REMOTE CONTROL REGISTRATION |
| SET VIDEO ▶ |

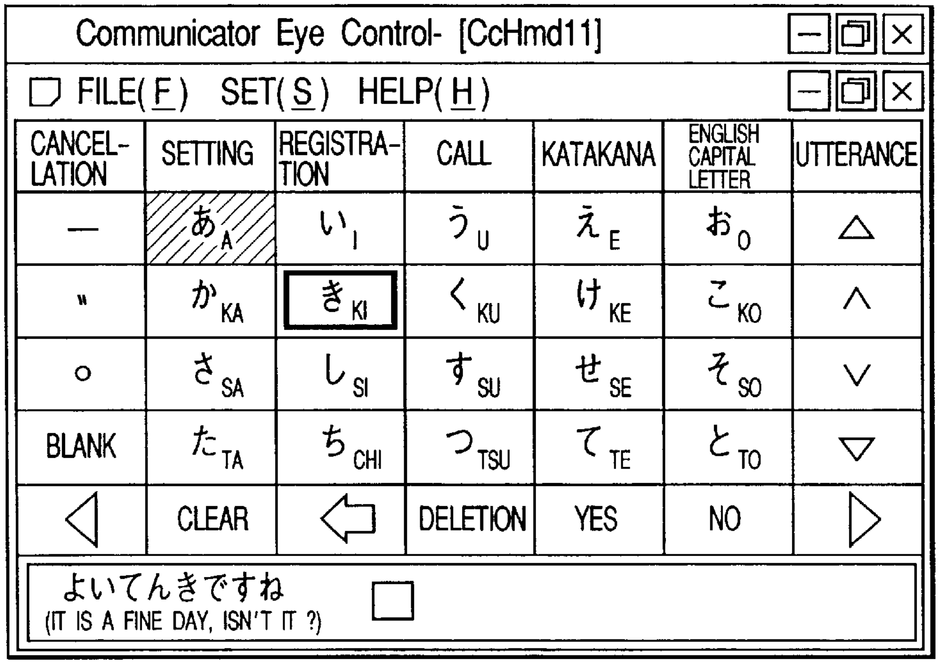

FIG. 23

| CANCEL-LATION | SETTING | REGISTRA-TION | CALL | KATAKANA | ENGLISH CAPITAL LETTER | UTTERANCE |
|---|---|---|---|---|---|---|
| — | あ A | い I | う U | え E | お O | △ |
| " | か KA | き KI | く KU | け KE | こ KO | ∧ |
| ○ | さ SA | し SI | す SU | せ SE | そ SO | ∨ |
| BLANK | た TA | ち CHI | つ TSU | て TE | と TO | ▽ |
| ◁ | CLEAR | ⇐ | DELETION | YES | NO | ▷ |

よいてんきですね
(IT IS A FINE DAY, ISN'T IT ?)

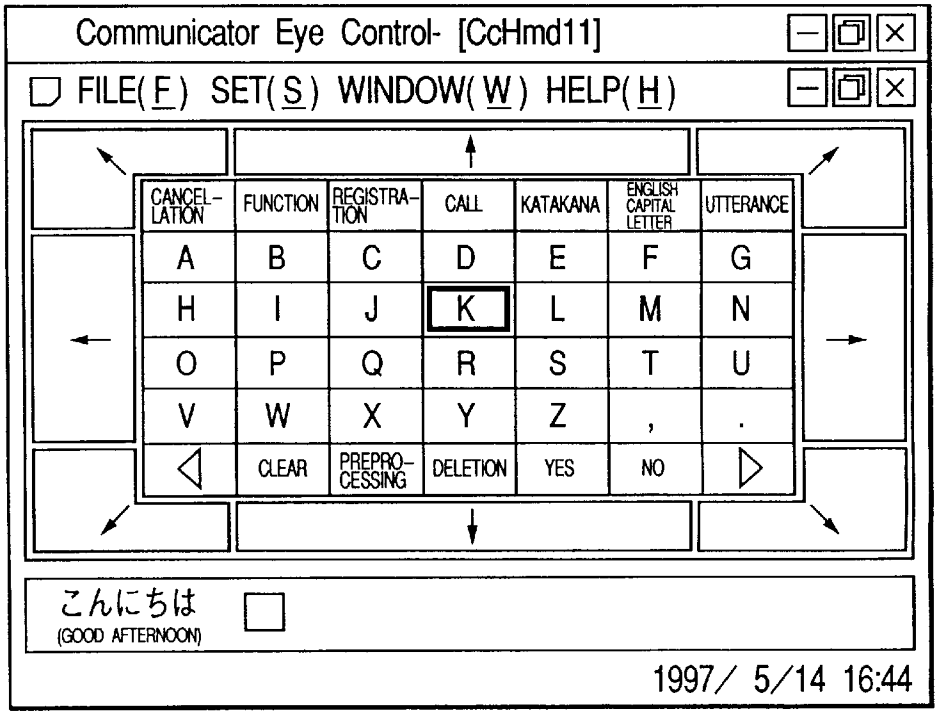

FIG. 24

Communicator Eye Control- [CcHmd11]

FILE(F) SET(S) WINDOW(W) HELP(H)

| CANCEL-LATION | FUNCTION | REGISTRA-TION | CALL | KATAKANA | ENGLISH CAPITAL LETTER | UTTERANCE |
|---|---|---|---|---|---|---|
| A | B | C | D | E | F | G |
| H | I | J | K | L | M | N |
| O | P | Q | R | S | T | U |
| V | W | X | Y | Z | , | . |
| ◁ | CLEAR | PREPRO-CESSING | DELETION | YES | NO | ▷ |

こんにちは
(GOOD AFTERNOON)

1997/ 5/14 16:44

VISUAL AXIS INPUT AND DECISION TRANSFER DEVICE AND METHOD

BACKGROUND OF THE INVENTION

1. Field of the Invention

The present invention relates to a visual-axis input and decision transfer device for detecting a visual axis of a user observing a display panel, and inputting a detection result of the user's visual axis as input information for the display panel to transfer a decision of the user, and a visual-axis input and decision-transfer method.

2. Related Background Art

A visual-axis input and decision-transfer device has been heretofore proposed and realized for detecting a visual axis of a user observing a display panel, and inputting a detection result of the user's visual axis as input information for the display panel to transfer user's decision. In an example of such visual axis input and decision-transfer device, a display panel indicating a plurality of characters such as hiragana or Japanese phonetic characters and alphabets is displayed on a computer screen, a visual axis of a user observing the display panel is detected, a character selected by the user is specified in accordance with a detection result of user's visual axis, and the specified character is inputted.

In the visual-axis input decision and transfer device, for example, in a known method of inputting the selected character, the selected character is confirmed as a character to be inputted by closing eyes while casting the visual axis to the character, or another action.

However, in the conventional visual-axis input and decision-transfer device, since the method of confirming the input by closing eyes or another action is used, the input cannot be performed if the eyes are closed too early. Therefore, in order to acquire an action timing for closing the eyes, the user is sometimes requested to have sufficient experience. Moreover, there is provided no means for notifying the user of an input failure caused by a too early timing of closing the eyes, of visual-axis detection failure by the user's eyes being not correctly captured, or of another visual-axis detection error. When the visual-axis detection errors frequently occur, the user cannot be notified of such condition, and may repeat wasteful input operations in vain without knowing the condition. In this manner, the user can obtain no visual-axis detection result such as the success or failure of the input by visual-axis detection. There is a possibility of user's repeating wasteful operations many times without noticing the failure of the input by visual axis including detection.

Moreover, when a large number of choices are displayed in the display panel, the display area of each choice is reduced, which makes it difficult to select an intended choice from the choices.

SUMMARY OF THE INVENTION

A first object of the present invention is to allow a user to confirm a detection result of a visual axis, and eliminate a possibility of a user's repeating wasteful operations many times.

A second object of the present invention is to allow the user to observe a display panel while observing an external video transmitted from outside.

A third object of the present invention is to allow the user to select a choice by visual-axis input while seeing the external video transmitted from the outside.

A fourth object of the present invention is to display selection items on the display panel in such a manner that the user can easily recognize them.

A fifth object of the present invention is to control an external device to continuously vary its control amount.

A sixth object of the present invention is to construct an operation environment in which the user can securely and easily perform a predetermined input, and user's input operation is facilitated.

In order to attain the aforementioned objects, the present invention provides a visual-axis input and decision-transfer device which is provided with visual-axis input means for detecting a visual axis of a user observing a display panel, and inputting a detection result of the user's visual axis as input information for the display panel to transfer a user's decision by the input information from the visual-axis input means. The device comprises visual-axis-detection-result-notification means for notifying the user of detection-result information indicating a visual-axis detection success, visual-axis detection failure, blinking, selecting of the same choice, and the like, in response to the detection result of user's visual axis.

There is also provided a visual-axis input and decision-transfer device which is provided with video-observation means for displaying a display panel which can be observed by a user, visual-axis detection means for detecting a visual axis of the user observing the display panel displayed by the video-observation means, and visual-axis input means for inputting a detection result of the user's visual axis by the visual-axis detection means as input information for the display panel displayed in the video-observation means, so that a user's decision is transferred by the input information from the visual-axis input means. The device comprises display-control means for performing a control to arrange and display the display panel and external video transmitted from outside in the video-observation means.

There is further provided a visual-axis input and decision-transfer device which is provided with video-observation means for displaying video which can be observed by a user, visual-axis detection means for detecting a visual axis of the user observing the video displayed by the video observation means, and visual-axis input means for inputting a detection result of the user's visual axis by the visual-axis detection means as input information for the video displayed in the video-observation means, so that a user's decision is transferred by the input information from the visual-axis input means. The device comprises external video-input means for inputting video from outside; and display-control means for performing a control to display the external video transmitted via the external video-input means in the video-observation means. When the external video is displayed in the video-observation means, the display control means can overlap and display a choice selected by the user's visual axis on the external video.

Moreover, there is provided a visual-axis input and decision-transfer device which is provided with video-observation means for displaying a display panel including selection items which can be observed by a user, visual-axis detection means for detecting a visual axis of the user observing the display panel displayed by the video-observation means, and visual-axis input means for inputting a detection result of the user's visual axis by the visual-axis detection means as input information for the display panel, so that a user's decision is transferred by the input information from the visual-axis input means. The device comprises display-control means for performing a control to change and display a display mode of the selection items on the display panel displayed by the video-observation means based on a user's instruction.

Furthermore, there is provided a visual-axis input and decision-transfer device which is provided with visual-axis input means for detecting a visual axis of a user facing a display panel, and inputting a detection result of the user's visual axis as input information for the display panel to transfer a user's decision by the input information from the visual-axis input means. The device comprises connection means for connecting an external device; display-control means for performing a control to display control items for the external device on the display panel; and output means for, when the input information is transmitted from the visual-axis input means to select an item for continuously varying a control amount from the control items of the display panel, continuously transmitting a command to continuously vary the control amount to the external device via the connection means.

Additionally, there is provided a visual-axis input and decision-transfer device which is provided with visual-axis input means for detecting a visual axis of a user facing a display panel, and inputting a detection result of the user's visual axis as input information for the display panel to transfer a user's decision by the input information from the visual-axis input means. The device comprises display-control means for performing a control to hierarchically display selection items on the display panel, so that a mode of confirming one decision of the user to transfer can be executed by sequentially following and selecting selection items positioned subordinate to the abovementioned selection items to input the input information according to a sequence of display of the selection items via the visual-axis input means.

There is also provided a visual-axis input and decision-transfer method for detecting a visual axis of a user observing a display panel, and inputting a detection result of the user's visual axis as input information for the display panel to transfer a user's decision. In the device, the user is notified of detection-result information indicating a visual-axis detection success, visual-axis detection failure, blinking, selecting of the same choice, and the like, in response to the detection-result of the user's visual axis.

Moreover, there is provided a visual-axis input and decision-transfer method for displaying a display panel which can be observed by a user by video-observation means, detecting a visual axis of the user observing the display panel displayed by the video-observation means, and inputting a detection result of the user's visual axis as input information for the display panel displayed by the video-observation means to transfer a user's decision. In the device, an external video is taken from outside, and the external video and the display panel can be arranged and displayed in the video-observation means.

There is further provided a visual-axis input and decision-transfer method for displaying a video which can be observed by a user by video-observation means, detecting a visual axis of the user observing the video displayed by the video-observation means, and inputting a detection result of the user's visual axis as input information for the video displayed by the video-observation means to transfer a user's decision. The method comprises steps of: inputting an external video from outside, and performing a control to display the inputted external video in the video-observation means; and, when the external video is displayed in the video-observation means, performing a control to overlap and display a choice selected by the user's visual axis on the external video.

Furthermore, there is provided a visual-axis input and decision-transfer method for displaying a display panel including selection items which can be observed by a user by video-observation means, detecting a visual axis of the user observing the display panel displayed by the video-observation means, and inputting a detection result of the user's visual axis as input information for the display panel to transfer a user's decision. In the device, a display mode of the selection items on the display panel displayed by the video-observation means is changed and displayed based on a user's instruction.

Additionally, there is provided a visual-axis input and decision-transfer method for detecting a visual axis of a user facing a display panel, and inputting a detection result of the user's visual axis as input information for the display panel to transfer a user's decision. The method comprises steps of: connecting an external device via connection means; performing a control to display control items for the external device on the display panel; and, when the input information is received to select an item for continuously varying a control amount from the control items of the display panel, continuously transmitting a command to continuously vary the control amount to the external device via the connection means.

There is also provided a visual-axis input and decision-transfer method for detecting a visual axis of a user facing a display panel, and inputting a detection result of the user's visual axis as input information for the display panel to transfer a user's decision by the input information. The method comprises steps of: performing a control to hierarchically display selection items on the display panel; and executing a mode of confirming one user's decision to transfer by sequentially following and selecting selection items positioned subordinate to the above-mentioned selection items to input the input information according to a sequence of display of the selection items.

BRIEF DESCRIPTION OF THE DRAWINGS

FIGS. 20, 21, 22 and 23 are views showing examples of a screen displayed in the head-mount display by the video-display processing in the visual-axis input and decision-transfer device according to a seventh embodiment of the present invention.

FIG. 24 is a view showing an example of a selection screen displayed in the head-mount display by a selection processing in the visual-axis input and decision-transfer device according to an eighth embodiment of the present invention.

DETAILED DESCRIPTION OF THE PREFERRED EMBODIMENTS

Embodiments of the present invention will be described hereinafter with reference to the drawings.

(a) First Embodiment

Figure 1A:
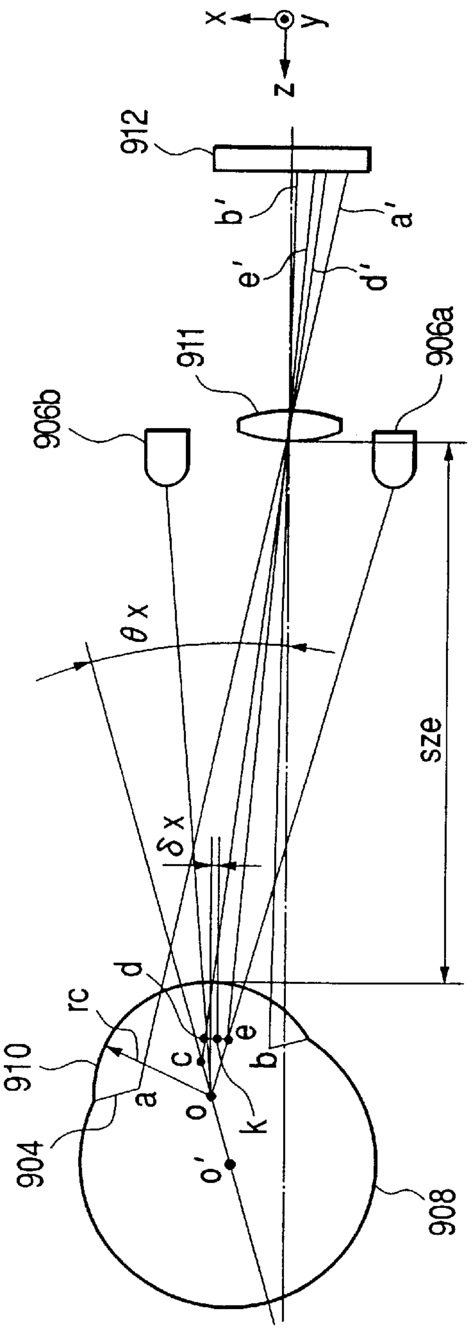
FIGS. 1A and 1B are views showing a principle of a visual-axis detection method.
Figure 1B:
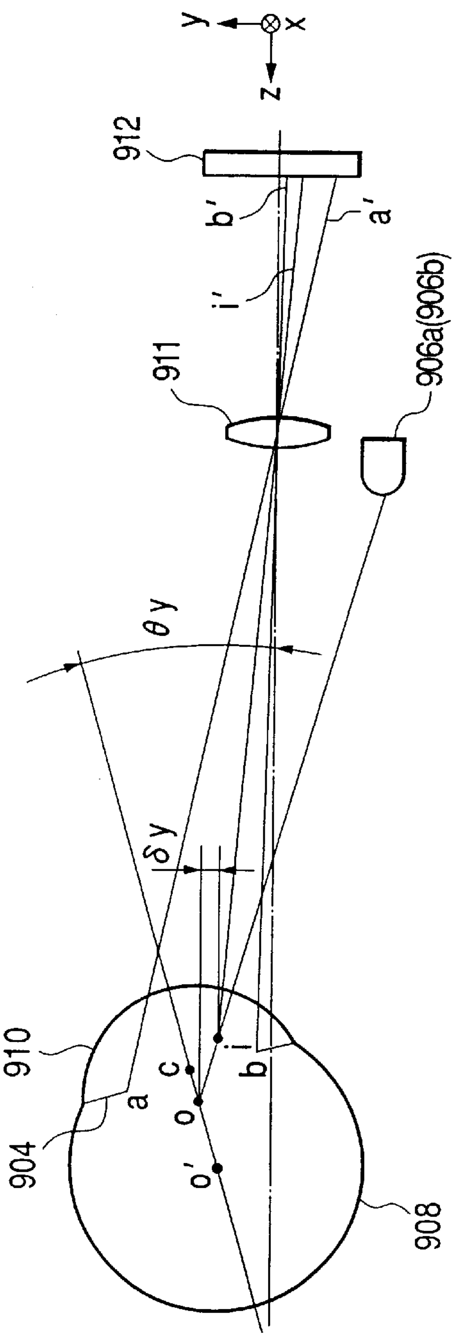
Figure 2A:
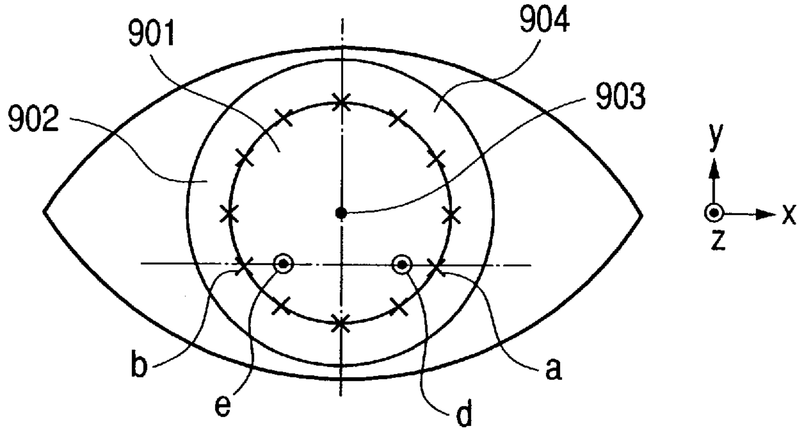
FIGS. 2A and 2B are views showing an image of an eyeball projected on an image sensor 912 of FIGS. 1A and 1B and a signal intensity.
Figure 2B:
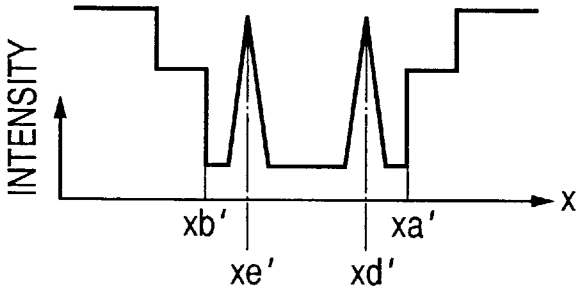

First, a principle of the visual-axis detection method will be described with reference to FIGS. 1A, 1B, 2A and 2B. FIGS. 1A and 1B show the principle of the visual-axis detection method: FIG. 1A is a top view; and FIG. 1B is a side view. FIGS. 2A and 2B show an image of the eyeball projected on an image sensor 912 of FIGS. 1A and 1B, and its signal intensity.

For the visual-axis detection, as shown in FIGS. 1A and 1B, light sources 906*a,* 906*b* are used, which comprise light emitting diodes (IRED) for radiating infrared rays insensitive to an observer. The light sources 906*a* and 906*b* are arranged substantially symmetrically in an x direction (horizontal direction) and slightly lower in a y direction (vertical direction), relative to a light axis of image forming lens 911. Infrared rays radiated from each light source 906*a,* 906*b* are reflected by observer's eyeballs, and a part of the reflected infrared rays are passed through the image forming lens 911 to form an image on the image sensor 912.

Here, first in a supposed horizontal plane, as shown in FIG. 1A, a cornea 910 of eyeball 908 of the observer is irradiated with the infrared rays radiated from the light source 906*b*. In this case, a cornea reflecting image d (virtual image) formed by the infrared rays reflected by a surface of cornea 910 is converged by the image forming lens 911 to form the image in position d' of the image sensor 912. Similarly, the observer's cornea 910 of eyeball 908 is irradiated with the infrared rays radiated from the light source 906*a*. In this case, a cornea reflecting image e (virtual image) formed by the infrared rays reflected by the surface of cornea 910 is converged by the image forming lens 911 to form the image in position e' on the image sensor 912. Moreover, luminous flux from ends a, b of iris 904 forms images in positions a', b' on the image sensor 912 via the image forming lens 911.

When a rotation angle θ of light axis of eyeball 908 relative to light axis of image forming lens 911 is small, and x-coordinates of the ends a, b of iris 904 are set to xa, xb, and a large number of points xa, xb are obtained on the image sensor 912 (refer to marks x in FIG. 2A). In this case, a pupil center xc is calculated by a least square method of a circle. On the other hand, when an x-coordinate of curvature center o of cornea 910 is set to xo, a rotation angle θx relative to the light axis of eyeball 908 is represented by following equation (1):

$$o{\cdot}c \sin \theta x = xc - xo \quad (1)$$

Moreover, when considering a predetermined correction value δx in a midpoint k of the cornea reflecting images d and e, xo is obtained by following equation (2):

$$xh=(xd+xe)/2xo=(xd+xe)/2+\delta x \quad (2)$$

Here, δx is a numeric value geometrically obtained from a device installation method, the eyeball distance, and the like. Therefore, θx is obtained from the equations (1), (2) as shown in following equation (3):

$$\theta x = \text{arc}\sin[[xc-\{(xd+xe)/2+\delta x\}]/oc] \quad (3)$$

Furthermore, when the coordinate of each characteristic point projected on the image sensor 912 is rewritten by affixing a dash thereto, following equation (4) is obtained:

$$\theta x = \text{arc}\sin[[xc'-\{(xd'+xe')/2+\delta x'\}]/oc/\beta] \quad (4)$$

Here, beta indicates a magnification determined by the eyeball distance size relative to the image forming lens 911, and is actually obtained as a function of the interval of cornea reflecting images |xd'−xe'|.

In a supposed vertical plane, as shown in FIG. 1B, the cornea reflecting images formed by two light sources 906*a,* 906*b* are generated in the same position, which is set to i. A method of calculating a rotation axis θy of eyeball 908 is the same as in the horizontal plane, but only the above equation (2) is different, and the y-coordinate yo of each curvature center o is obtained by the following equation (5):

$$yo=yi+\delta y \quad (5)$$

Here, δy is a numeric value geometrically obtained from the device installation method, the eyeball distance, and the like. Therefore, a rotation axis θy in the vertical direction is obtained as shown in the following equation (6):

$$\theta y=\text{arc}\ \sin[[yc'-(yi'+\delta y')]/oc/\beta] \quad (6)$$

Furthermore, the position coordinate (xn, yn) on a finder or another screen is represented on horizontal and vertical planes by the following equations (7), (8), respectively, using a constant m determined by a finder optical system:

$$xn=m\cdot\text{arc}\ \sin[[xc'-\{(xd'+xe')/2+\delta x'\}]/oc/\beta] \quad (7)$$

$$yn=m-\text{arc}\ \sin[[yc'-(yi'+\delta y')]/oc/\beta] \quad (8)$$

As is apparent from FIG. 2B, the pupil edge is detected using a trailing edge xb' and rising edge xa' of an output waveform of image sensor 912. Moreover, the coordinate of the cornea reflecting image is detected using sharp rising portions xe' and xd'.

Figure 4:
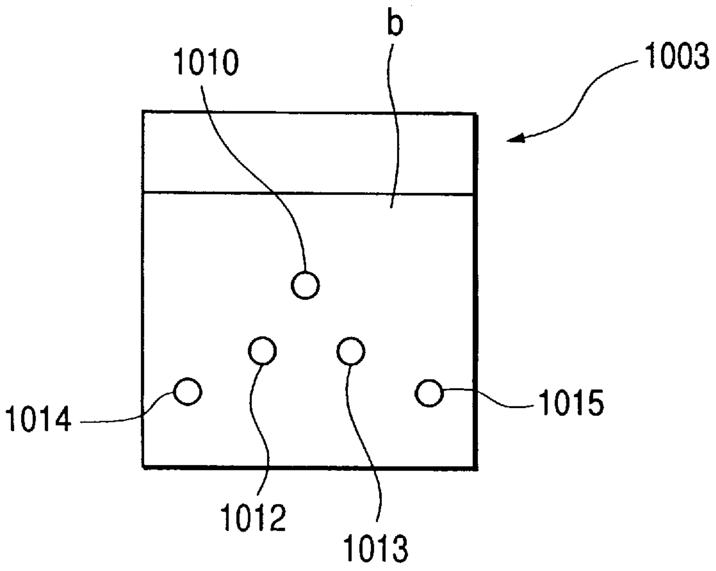
FIG. 4 is a side view showing a shape of prism 1003 in the visual-axis input and decision-transfer device of FIG. 3.
Figure 3:
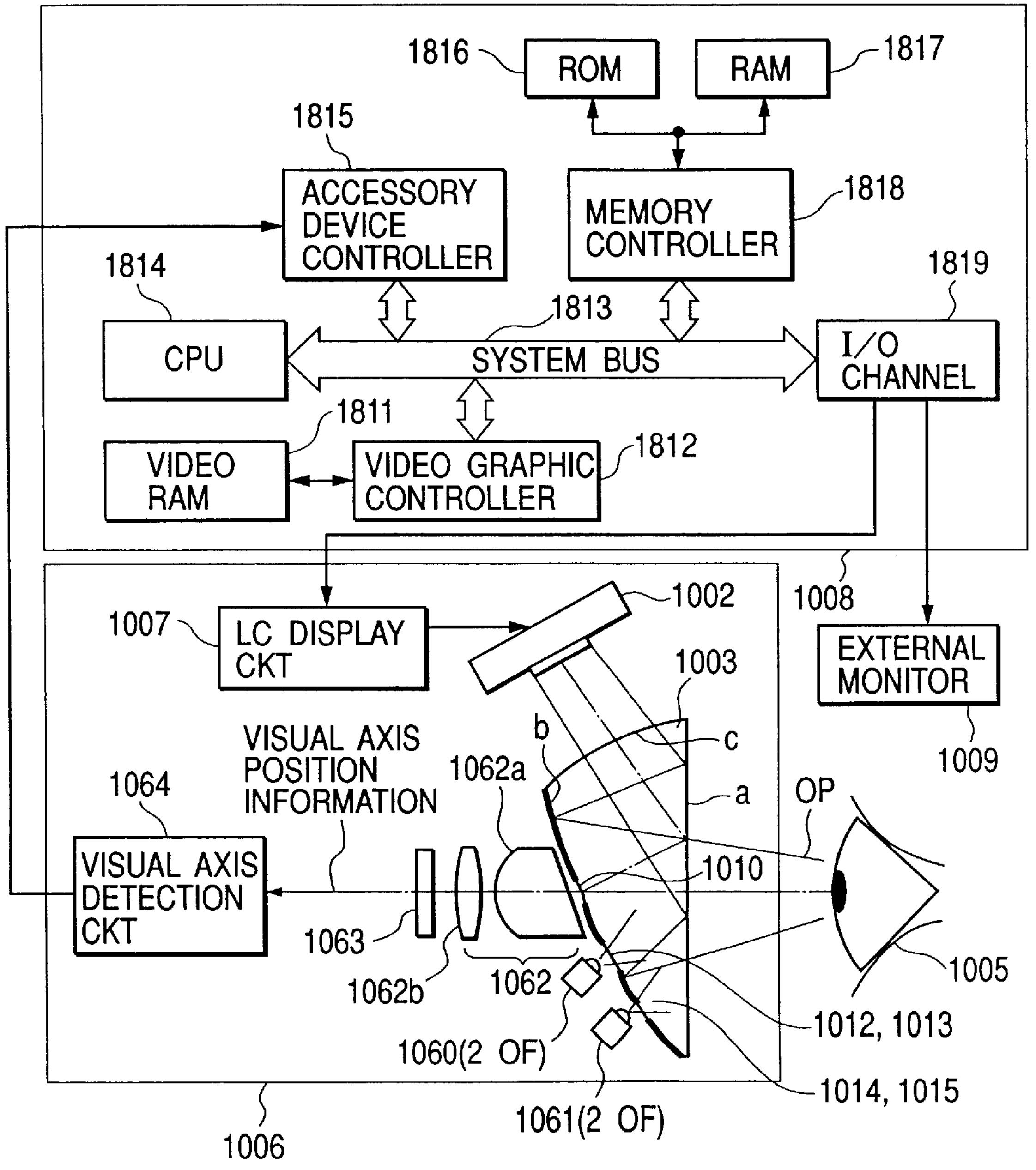
FIG. 3 is a block diagram showing a structure of a visual-axis input and decision-transfer device according to a first embodiment of the present invention.
Figure 5:
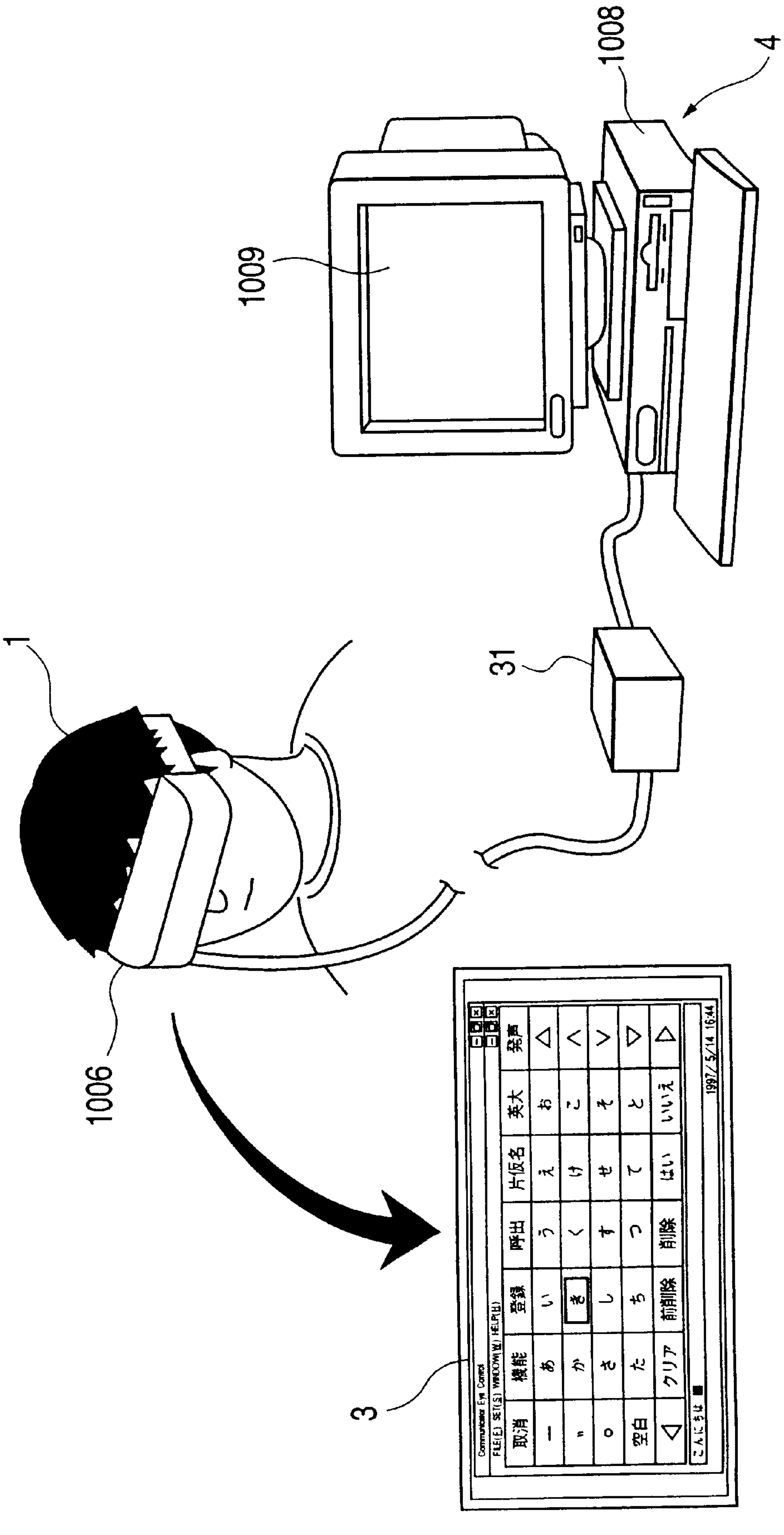
FIG. 5 is a schematic view showing an operation state of the visual-axis input and decision-transfer device of FIG. 3.

A structure of the visual-axis input and decision-transfer device in the embodiment will next be described with reference to FIGS. 3 to 5. FIG. 3 is a block diagram showing the structure of the visual-axis input and decision-transfer device according to the first embodiment of the present invention, FIG. 4 is a side view showing a shape of prism 1003 in the visual-axis input and decision-transfer device of FIG. 3, and FIG. 5 is a schematic view showing an operation state of the device of FIG. 3.

The visual-axis input and decision-transfer device is, as shown in FIG. 3, constituted of a head-mount display 1006, a personal computer (hereinafter referred to as PC) 1008, and an external monitor 1009. The head-mount display 1006 is in the form of goggles, glass frames, or the like, and attached to the user in such a manner that it is positioned in the vicinity of the user's eyes. The head-mount display 1006 observes a video displayed in a screen of an external monitor 1009, detects a position of user's visual axis cast to the video, and inputs the detection result into PC 1008.

The head-mount display 1006 comprises video-observation means for displaying the video on the external monitor 1009 in such a manner that the user can observe it, and visual-axis detection means for detecting a visual-axis of the user observing the video displayed by the video-observation means to input the visual-axis detection result into the PC 1008.

Specifically, the video-observation means comprises a liquid crystal display element 1002 for indicating the video displayed by the external monitor 1009, a liquid-crystal display circuit 1007 for operating the liquid-crystal display element 1002, and a special prism 1003 for enlarging the video displayed by the liquid crystal display element 1002 to project it to user's eyes 1005. Moreover, the visual-axis detection means comprises infrared-ray emitting diodes 1060, 1061 for radiating infrared-rays to the user's eyes 1005 via the special prism 1003, and image-forming lens system 1062 for receiving the infrared rays reflected by the user's eyes 1005 via the special prism 1003 to form an image of incident infrared rays to an image pickup face of photoelectric conversion element 1063. The image forming lens system 1062 is constituted of two lenses 1062*a*, 1062*b*. The photoelectric-conversion element 1063 converts the infrared rays formed in the image on the image-pickup face to electric signals by photoelectric conversion, and the electric signals are transmitted to a visual-axis detection circuit 1064 as visual-axis position information. The visual-axis detection circuit 1064 obtains the user's attention point on the image projected via the special prism 1003 based on the inputted visual-axis position information, and transmits the obtained attention point to the PC 1008 as the visual-axis position information. A method of obtaining the attention point is performed in accordance with the aforementioned principle of visual-axis detection method. Additionally, the infrared ray emitting diode 1060 comprises, for naked eyes, two light-emitting diodes arranged in a depth direction of sheet surface, while the infrared-ray emitting diode 1061 comprises, for eyeglasses, two light-emitting diodes arranged in the depth direction of sheet surface.

An optical action of video-observation means in the head-mount display 1006 will next be described. Light from the liquid-crystal display element 1002 is refracted/transmitted through a third optical-action face c of special prism 1003 to enter the special prism 1003, and the incident light is totally reflected by a first optical-action face a. After the totally reflected light is reflected by a second optical-action face or special action face b, it is refracted/transmitted through the first optical-action face a to form a luminous flux having a spreading angle (converging angle) suitable for user's vision degree, and radiated toward the eyes.

Additionally, a straight line connecting the user's eyes 1005 and center of liquid-crystal display element 1002 is indicated as a basic light axis. Adjustment of the user's vision degree is realized by moving the liquid-crystal display element 1002 in parallel along the light axis of the special prism 1003. In order to form the special prism 1003 in a ter-centric system by correcting image performance and strain, three optical action faces are preferably constituted of three-dimensional curved faces each having no rotating symmetrical axis. In this case, the prism includes the basic light axis and has a curved face structure symmetrical only to a plane parallel with a sheet face.

An optical action of visual-axis detection means will next be described. The infrared rays emitted from the infrared ray emitting diodes 1060, 1061 are radiated to the user's eyes 1005 via openings 1012, 1013, 1014, 1015 formed in the second optical action face b from a direction different from the light axis of the visual-axis detection means.

The infrared rays radiated to the user's eyes 1005 are reflected by the corneas and pupils of the eyes 1005 and scattered. The infrared rays reflected by the corneas form a cornea reflecting image, while the infrared rays reflected by the pupils form a pupil image. These infrared rays are guided to the image forming lens system 1062 via an opening 1010 formed in the second optical action face b to form the image on the image-pickup face of the photoelectric conversion element 1063 by the image-forming lens system 1062. The photoelectric conversion element 1063 converts the image of infrared rays formed on its image pickup face to electric signals, and the electric signals are transmitted to the visual axis detection circuit 1064.

The openings 1012, 1013, 1014, 1015 formed in the second optical-action face b of the special prism 1003 are, as shown in FIG. 4, arranged on opposite sides of the opening 1010. Here, the openings 1012, 1013 are, as described above, formed opposite to the infrared-ray emitting diodes 1060 for naked eyes, while the openings 1014, 1015 are formed opposite to the infrared ray emitting diodes 1061 for eyeglasses. The arrangement of openings is determined by the arrangement of infrared-ray emitting diodes. In the embodiment, the infrared ray emitting diodes 1060 for naked eyes are arranged below and slightly apart from the light axis of the visual-axis detection means, at the same height, and symmetrically with a narrow width on opposite sides of the light axis. On the other hand, the infrared-ray emitting diodes 1061 for eyeglasses are arranged below and slightly apart from the light axis of the visual-axis detection means, at the same height, and symmetrically with a broad width on opposite sides of the light axis. In the arrangement, eyeballs can uniformly be irradiated, and the visual axis can precisely be detected. Additionally, the naked eyes are distinguished from the eyeglasses by calculating the distance between eyeglasses and special prism 1003 from the interval of cornea reflecting images |xd'−xe'|.

Furthermore, in the embodiment, the image-forming lens system 1062 is constituted of two lenses 1062*a,* 1062*b*. When the lens 1062*b* has a wedge shape, however, the image-forming lens system 1062 can be constituted of a small number of lenses, which contributes to miniaturization of the head-mount display. Moreover, an eccentricity aberration generated on the second optical-action face b can effectively be corrected by applying a curvature to a face (slanting face) of lens 1062*a* opposite to the special prism 1003. Furthermore, the image-forming performance outside the axis can effectively be corrected by providing the image forming lens system with at least one non-spherical face.

Moreover, when a diaphragm is provided between image-forming lens system 1062 and special prism 1003, and positioned closer to the opening 1010, the opening 1010 can be reduced in size, and null areas of image for the video-observation means can be minimized. Especially, the diaphragm is preferably equal in size to the opening 1010. When the size of the opening 1010 is set to 2 mm or less, it becomes smaller than the eye pupil, so that the generation of image-null areas for the user can securely be suppressed.

Furthermore, in the embodiment, the infrared rays to which the user's eyes are insensitive are used, but in this case, visual-axis detection accuracy can be enhanced by providing the image-forming lens system with a lens formed of a member which cuts visible rays.

The PC 1008 will next be described. The PC 1008 comprises CPU 1814 for performing various arithmetic operations and processings; memory controller 1818 for controlling reading or writing for ROM 1816 with BIOS program stored therein and RAM 1817 as an operation area of CPU 1814; accessory-device controller 1815 with a mouse or another pointing device, keyboard, visual-axis detection circuit of head-mount display 1006, and the like connected thereto for receiving outputs from these devices; video graphic controller 1812 for controlling in such a manner that the content written in video RAM 1811 is displayed on the external monitor 1009 or the liquid-crystal display element 1002 of head mount-display 1006; and I/O channel 1819 to which the external monitor 1009 or the liquid-crystal display circuit 1007 of head-mount display 1006 is connected. These blocks are connected to one another via a system bus 1813.

In the embodiment, the PC 1008 performs a video-display processing for supplying video data observed by the user to the liquid-crystal display circuit 1007 of head-mount display 1006; and an input processing for receiving visual-point position data from the visual-axis detection circuit 1064 of head-mount display 1006 via the accessory device controller 1815, and specifying a choice selected from choices included in the video displayed on the liquid-crystal display element 1002 based on the visual point position data to input the specified choice. Moreover, a detection result-notification processing can be performed, in which the visual-axis detection success, the visual-axis detection failure, blinking, selecting of the same choice, or another detection-result condition is judged based on the visual-point position data, and the user is notified of detection-result information indicating the detection-result condition in accordance with the judgment result. Whether or not to perform the detection-result notification processing can be selected and set in accordance with user's instruction. Additionally, in the embodiment, the user is notified of the detection-result information by changing and displaying frame colors of selection items included in the video observed by the user.

These processings are performed by executing a program for constructing a visual-axis input and decision-transfer system read beforehand from a hard disc (not shown) or another storage medium by CPU 1814.

The operation of the visual-axis input and decision-transfer device will next be described with reference to FIG. 5. Here, the visual-axis input and decision-transfer device comprises the head-mount display 1006 attached to a head of user 1 in the same manner as eyeglasses, a PC unit 4 having the PC 1008 and external monitor 1009, and an adapter 31 for connecting the head mount display 1006 and PC 1008 and supplying electric power to the head mount display 1006.

In the operation, the PC unit 4 is first started to execute the program for constructing the visual-axis input and decision-transfer system. Subsequently, the user 1 puts on the head-mount display 1006 connected to the PC 1008 via the adapter 31. Video is supplied to the head-mount display 1006 from the PC 1008, and the head mount display 1006 displays the supplied video for the user 1. For example, as shown in FIG. 5, a screen 3 on which hiragana or Japanese phonetic characters, alphabets and the like are selected and inputted is displayed in the head mount display 1006, so that the user 1 can observe the screen 3. When a desired character on the screen 3 is selected and inputted, the user 1 casts his visual axis to the desired character on the screen 3. When the position of the cast visual axis is detected, the corresponding character is selected and inputted based on the detected visual-axis position. The head-mount display 1006 serves as a pointing device for the video generated by the PC 1008 in this manner.

Figure 6:
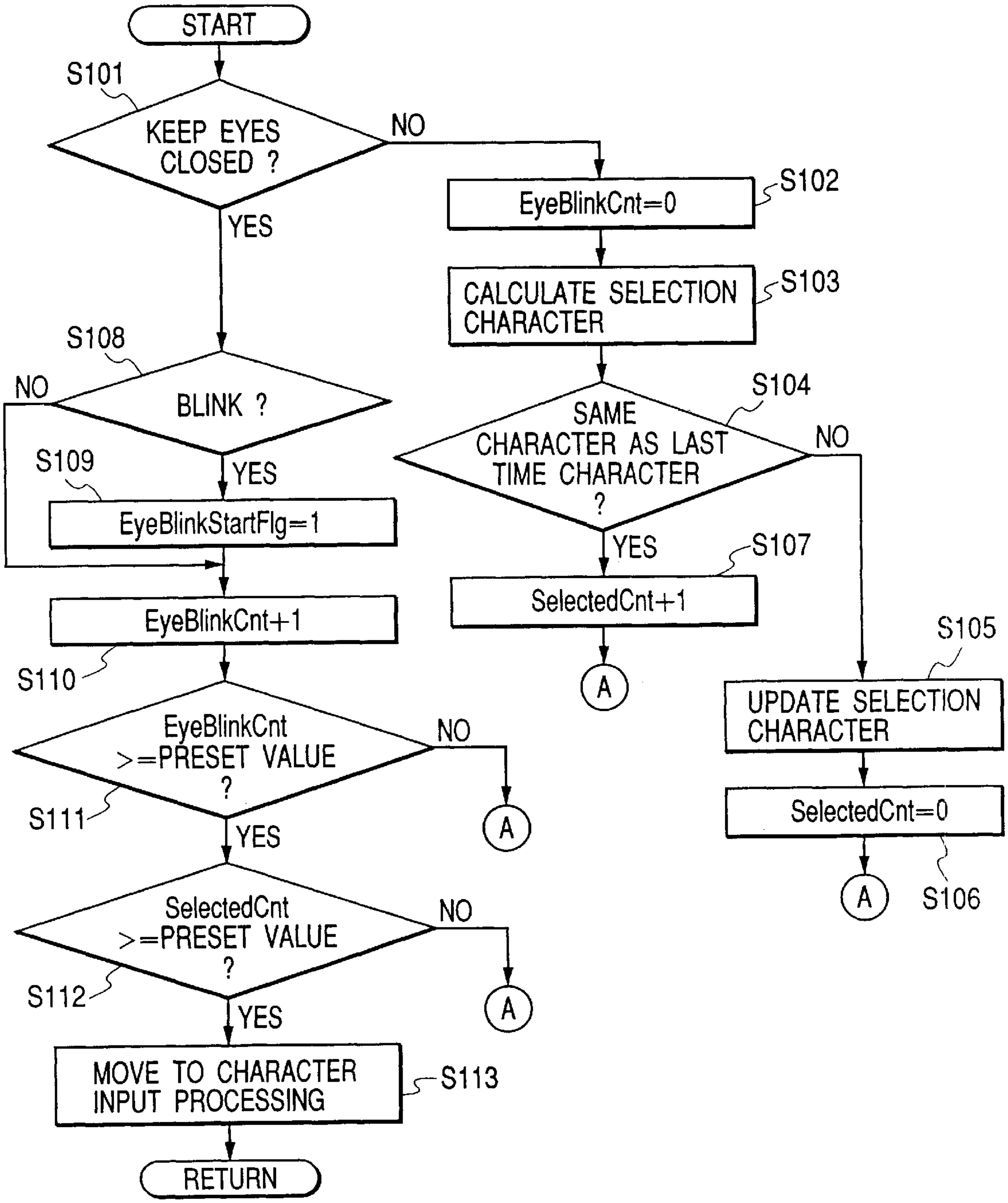
FIGS. 6 and 7 are flowcharts showing a procedure of visual-axis-detection-result-information-notification processing in the visual-axis input and decision-transfer device of FIG. 3.
Figure 7:
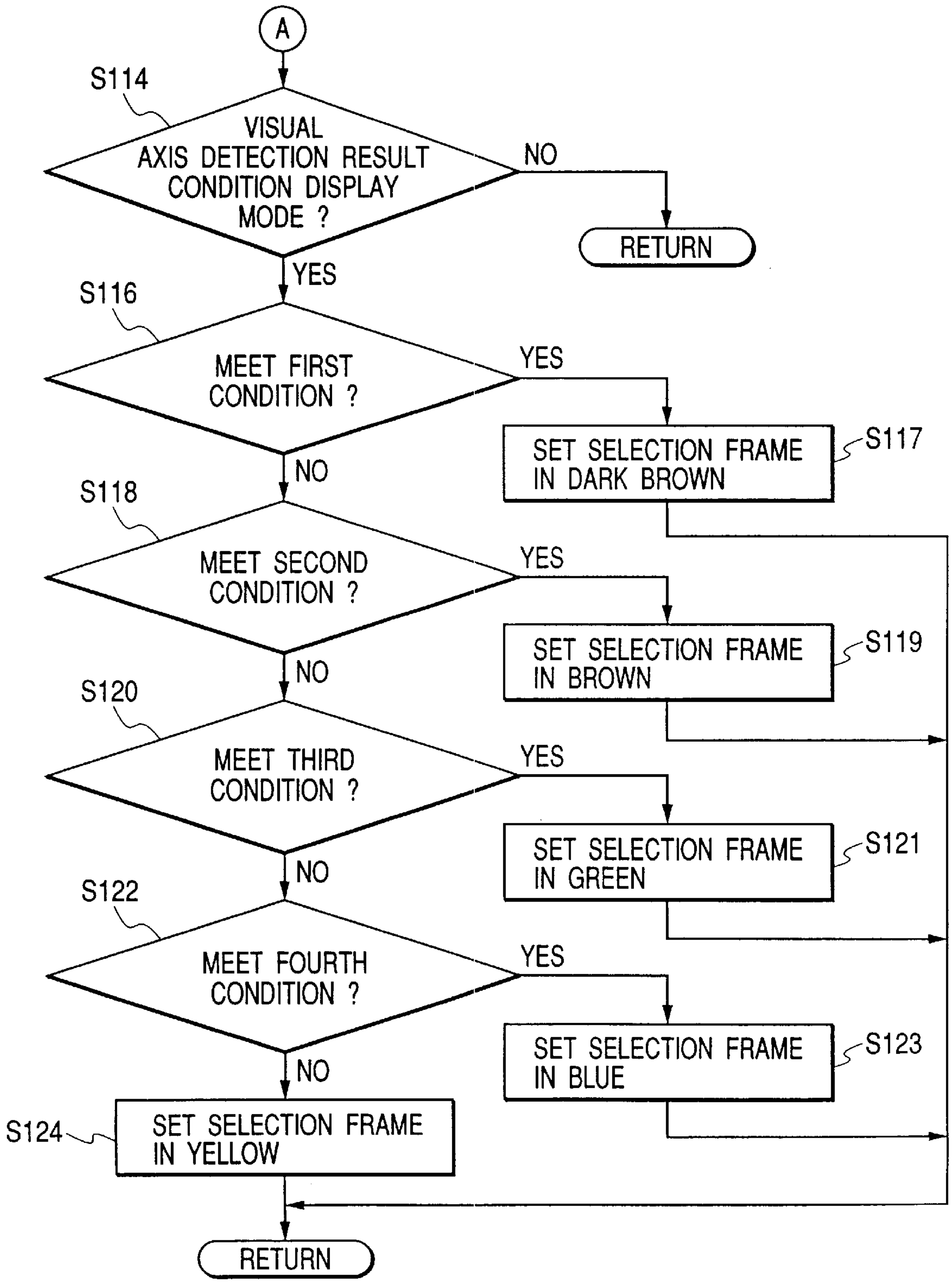

A procedure of visual-axis detection result information notification processing will next be described with reference to FIGS. 6 and 7. FIGS. 6 and 7 are flowcharts showing a procedure of visual-axis-detection-result-information-notification processing in the visual-axis input and decision transfer device of FIG. 3.

Referring to FIG. 6, first in step S101, it is determined based on visual-axis position data from the visual axis detection circuit 1064 of head-mount display 1006 whether or not the user keeps his eyes closed. When the user does not close his eyes, the processing goes to step S102 to reset to zero a counter EyeBlinkCnt for counting a time to keep the eyes closed. Subsequently, at step S103, the character present in the visual-axis position is calculated as the selected character based on the visual-axis position data from the visual-axis detection circuit 1064. Subsequently, it is determined at step S104 whether or not the present-selected character is the same as the last-time character. When the present-selected character is the same as the last-time character, the processing advances to step S107 to increment by one a counter SelectedCnt constituted of an up-counter. Then the processing advances to step S114 shown in FIG. 7. On the other hand, when the present-selected character is not the same as the last-time character, at step S105, selected character data is updated to the present-selected character. Subsequently, at step S106, the counter SelectedCnt is reset to zero, and the processing advances to the step S114.

When it is determined in the step S101 that the user keeps his eyes closed, the processing advances to step S108 to determine whether the user closes or blinks his eyes by judging whether or not detection data indicative of a blink is transmitted from the visual-axis detection circuit 1064. When it is determined that the user blinks, the processing advances to step S109 for setting a flag EyeBlinkStartFlg to one, then advances to step S110. On the other hand, when it is determined that the user does not blink, the processing skips the step S109 and advances to the step S110 to increment by one the counter EyeBlinkCnt for counting the time to keep the eyes closed. Subsequently, at step S111, it is determined whether or not a count value of counter EyeBlinkCnt is equal to or more than a preset value. When the count value of counter EyeBlinkCnt is less than the preset value, the processing advances to the step S114 shown in FIG. 7.

On the other hand, when the count value of counter EyeBlinkCnt is equal to or more than the preset value, the processing advances to step S112 to determine whether or not a count value of counter SelectedCnt is equal to or more than a preset value. Here, the preset value for the counter SelectedCnt is different from the preset value for the counter EyeBlinkCnt. When the count value of counter SelectedCnt is less than the preset value, the processing advances to the step S114 shown in FIG. 7. When the count value of counter SelectedCnt is equal to or more than the preset value, and the values of counters EyeBlinkCnt and SelectedCnt meet the preset values, it is judged that conditions for performing character input are established, thereby advancing to step S113 to move to a character input processing.

After the step S106 or S107 is executed, or when a negative response is made at the step S111 or S112, the processing advances to step S114. As shown in FIG. 7, it is determined at the step S114 whether or not a visual-axis-detection-result-condition-display mode is set. When the mode is not set, the processing returns. On the other hand, when the visual-axis-detection-result-condition-display mode is set, the processing advances to step S116 to determine whether or not the count value of counter EyeBlinkCnt and the value of flag EyeBlinkStartFlg meet values defined by a first condition. Here, to meet the first condition means that relationships of the count value of counter EyeBlinkCnt≧1, value of flag EyeBlinkStartFlg=0 is established. When the first condition is met, i.e., when the count value of counter EyeBlinkCnt is one or more, but the value of flag EyeBlinkStartFlg is zero, it is judged that the user keeps his eyes closed and no blink is detected. The processing advances to step S117 to change a color of selection of frame of the corresponding character in the video of liquid-crystal display element 1002 observed by the user to a color indicating that the user keeps his eyes closed and no blink is detected, and the processing returns. For example, the frame is set in dark brown as the color indicating that no blink is detected.

On the other hand, when the first condition is not met, the processing advances to step S118 to determine whether or not the count value of counter EyeBlinkCnt, the value of flag EyeBlinkStartFlg, and the count value of counter SelectedCnt meet values defined by a second condition. Here, to meet the second condition means that the relationships of the count value of counter EyeBlinkCnt≧1, the value of flag EyeBlinkStartFlg=1, the count value of counter SelectedCnt<preset value are established. When the second condition is met, i.e., when the count value of counter EyeBlinkCnt is one or more, and the value of flag EyeBlinkStartFlg is one, blinks are detected to confirm the input of the selected character. However, since the count value of counter SelectedCnt does not reach the preset value, it is judged that the selected character is not confirmed, and the processing advances to step S119. After the color of the selection frame of the corresponding character in the video of liquid-crystal display element 1002 observed by the user is changed to a color indicating that selection is not confirmed, the processing returns. Here, the frame is set in brown as an example of the color indicating that the selection is not confirmed.

Moreover, when the second condition is not met, the processing advances to step S120 to determine whether or not the count value of counter EyeBlinkCnt, the value of flag EyeBlinkStartFlg and count value of counter SelectedCnt meet values defined by a third condition. Here, to meet the third condition means that relationships of the count value of counter EyeBlinkCnt≧1, the value of flag EyeBlinkStartFlg=1, the count value of counter SelectedCnt≧preset value are established. When the third condition is met, i.e., when the count value of counter SelectedCnt reaches the preset value, the selected character is confirmed. However, since the count value of counter EyeBlinkCnt is one or more, and the value of flag EyeBlinkStartFlg is one, it is judged that the input of the selected character can be defined after the eyes are kept closed for a predetermined time. The processing advances to step S121 to change the display color of the selection frame of the corresponding character in the video of liquid-crystal display element 1002 observed by the user to a color indicating that the character input can be defined after the eyes are kept closed for the predetermined time, and the processing returns. Here, the frame is set in green as an example of the color indicating that if the eyes are kept closed for the predetermined time, the character input can be defined.

On the other hand, when the third condition is not met, the processing advances to step S122 to determine whether or not the count value of counter SelectedCnt meets a value defined by a fourth condition. Here, to meet the fourth condition means that the relationship of the count value of counter SelectedCnt≧preset value is established. When the fourth condition is met, i.e., when the count value of counter SelectedCnt reaches the preset value, the selected character is confirmed. However, since the first and third conditions are not met, it is judged that the eyes are not closed, and the processing advances to step S123. The display color of the selection frame of the corresponding character in the video of liquid-crystal display element 1002 observed by the user is changed to a color indicating that the character selection is defined, and the processing returns. Here, the frame is set in blue as an example of the color indicating that the character selection is defined.

When the fourth condition is not met, i.e., when the first to fourth conditions are not met, it is judged that the eyes are open. Moreover, since the relationship of the count value of counter SelectedCnt<preset value is satisfied, it is judged that the character selection is not performed, and the processing advances to step S124. The display color of the selection frame of the corresponding character in the video of the liquid crystal display element 1002 observed by the user is changed to a color indicating that the item selection is not performed, and the processing returns. Here, the frame is set in yellow as an example of the color indicating that the character selection is not performed.

As described above, in the embodiment, the user is notified of the detection-result information by changing and displaying the color of the selection frame of selectable character included in the video observed by the user. Therefore, the user can confirm the visual-axis-detection result. A possibility of the user's repeating wasteful operation can be eliminated.

Additionally, in the embodiment, the user is notified of the detection-result information by changing and displaying the color of the selection frame of selectable character observed by the user, but instead, the user may be notified of the detection-result information by changing a color of the selection character, the background color of the selection character, or the like. Furthermore, the case for selecting the character has been described, but it goes without saying that even when another selection item constituted of a graphic or the like is selected, the visual-axis detection result state can be notified in the same manner.

(b) Second Embodiment

Figure 8:
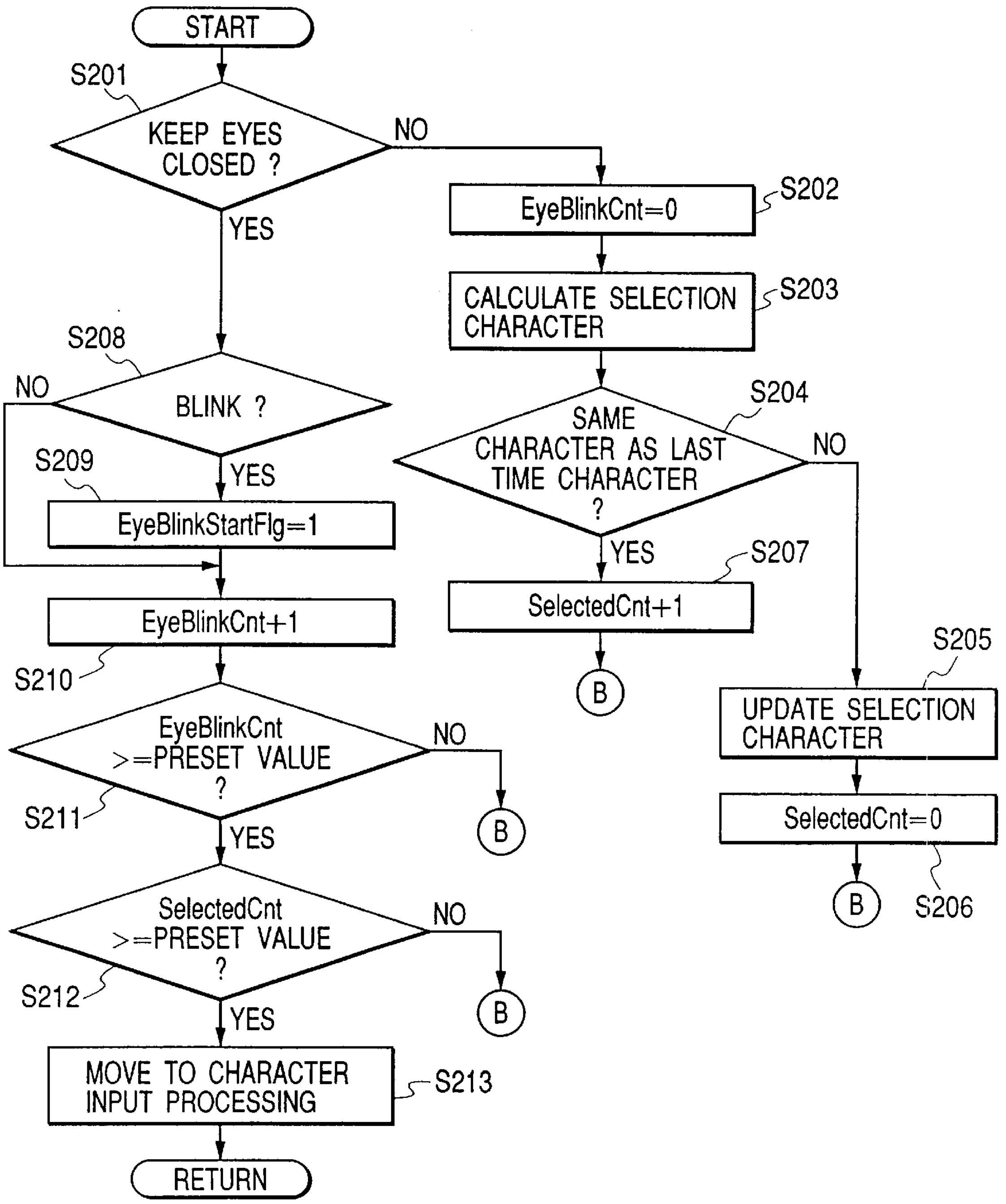
FIGS. 8 and 9 are flowcharts showing a procedure of visual-axis-detection-result-information-notification processing in the visual-axis input and decision-transfer device according to a second embodiment of the present invention.
Figure 9:
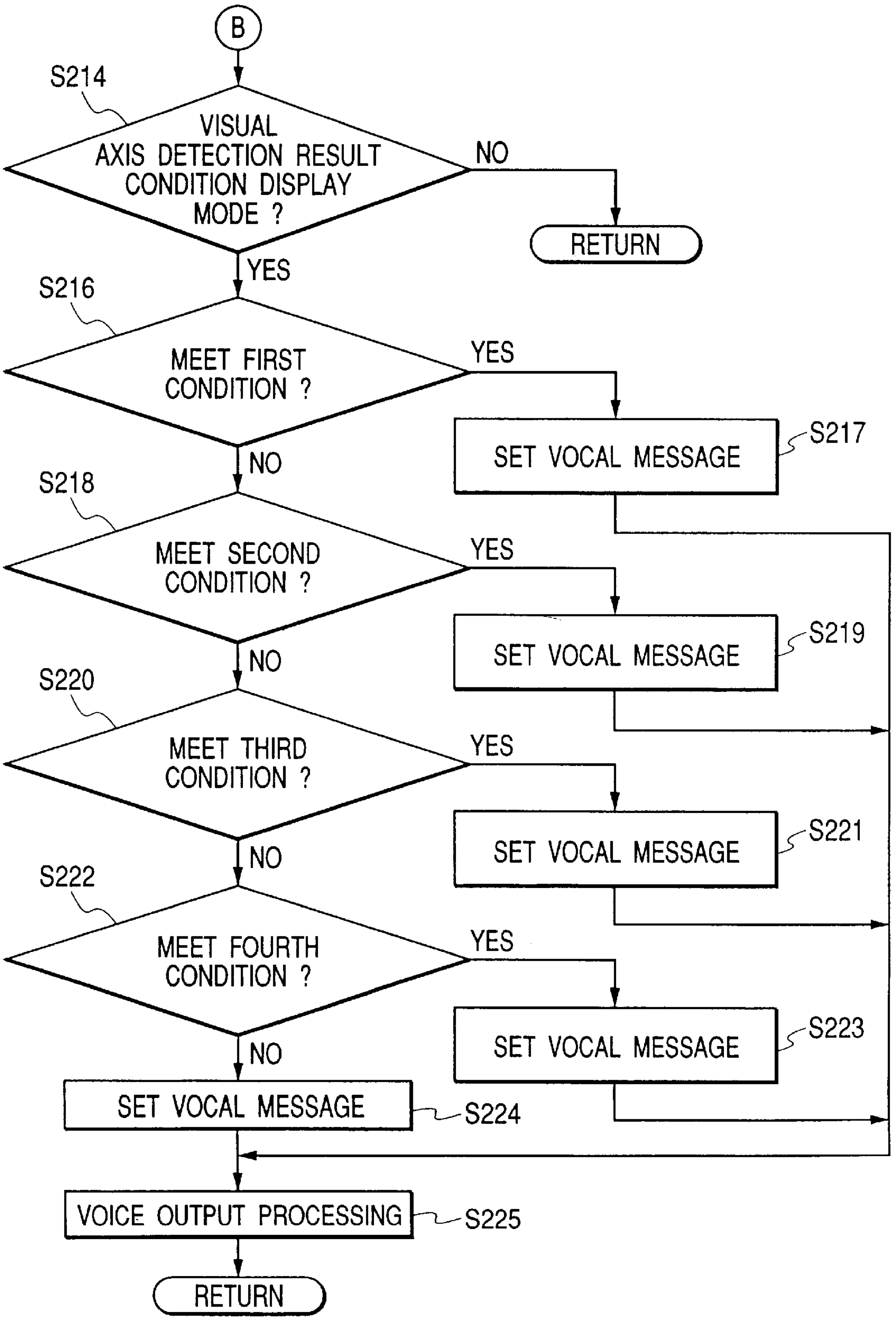

A second embodiment of the present invention will next be described with reference to FIGS. 8 and 9. FIGS. 8 and 9 are flowcharts showing the procedure of visual-axis-detection-result-information-notification processing in the visual-axis input and decision-transfer device according to the second embodiment of the present invention.

The embodiment is different from the first embodiment in that the detection-result information is notified by a vocal message emitted from a speaker incorporated in the PC 1008. Additionally, the embodiment has the same constitution as the first embodiment, and the description thereof is omitted.

The procedure of the visual-axis-detection-result-information-notification processing will next be described with reference to FIGS. 8 and 9.

Referring to FIG. 8, first in step S201, it is determined based on the visual-axis position data from the visual-axis detection circuit 1064 of head-mount display 1006 whether or not the user keeps his eyes closed. When the user does not close his eyes, the processing goes to step S202 for resetting the counter EyeBlinkCnt to zero. Subsequently, at step S203, the character present in the visual-axis position is calculated as the selected character based on the visual-axis position data from the visual-axis detection circuit 1064. Subsequently, it is determined at step S204 whether or not the present selected character is the same as the last time character. When the present-selected character is the same as the last-time character, the processing advances to step S207 for incrementing the counter SelectedCnt by one. Then the processing advances to step S214 shown in FIG. 9. On the other hand, when the present-selected character is not the same as the last-time character, at step S205, the selected character data is updated to the present selected character. Subsequently, at step S206, the counter SelectedCnt is reset to zero, and the processing advances to the step S214.

When it is determined in the step S201 that the user keeps his eyes closed, the processing advances to step S208. It is then determined whether the user closes or blinks his eyes by judging whether or not the detection data indicative of a blink is transmitted from the visual-axis detection circuit 1064. When it is determined that the user blinks, the processing advances to step S209 for setting the flag EyeBlinksStartFlg to one, then advances to step S210. On the other hand, when it is determined that the user does not blink, the processing skips step S209 and advances to the step S210 to increment the counter EyeBlinkCnt by one.

Subsequently at step S211, it is determined whether or not the count value of counter EyeBlinkCnt is equal to or more than the preset value. When the count value of counter EyeBlinkCnt is less than the preset value, the processing advances to the step S214 shown in FIG. 9.

On the other hand, when the count value of counter EyeBlinkCnt is equal to or more than the preset value, the processing advances to step S212 for determining whether or not the count value of counter SelectedCnt is equal to or more than the preset value. Here, the preset value for the counter SelectedCnt is different from the preset value for the counter EyeBlinkCnt. When the count value of counter SelectedCnt is less than the preset value, the processing advances to the step S214 shown in FIG. 9. When the count value of counter SelectedCnt is equal to or more than the preset value, and the values of counters EyeBlinkCnt and SelectedCnt meet the preset values, it is judged that the conditions for performing the character input are established, thereby advancing to step S213 to move to the character-input processing.

After the step S206 or S207 is executed, or when a negative response is made at the step S211 or S212, the processing advances to step S214. As shown in FIG. 9, it is determined at the step S214 whether or not the visual-axis-detection-result-condition-display mode is set. When the mode is not set, the processing returns. On the other hand, when the visual-axis-detection-result-condition-display mode is set, the processing advances to step S216 to determine whether or not the count value of counter EyeBlinkCnt and the value of flag EyeBlinkStartFlg meet values defined by the first condition. Here, to meet the first condition means that the relationships of the count value of counter EyeBlinkCnt≧1, and the value of flag EyeBlinkStartFlg=0 are established. When the first condition is met, i.e., when the count value of counter EyeBlinkCnt is one or more, but the value of flag EyeBlinkStartFlg is zero, it is judged that the user keeps his eyes closed and no blink is detected. The processing advances to step S217, in which a vocal message indicating that the eyes are closed and no blink is detected is set in a voice-output memory. Subsequently, the processing advances to step S225, a voice output processing is performed so that the vocal message set in the voice-output memory is emitted from the speaker, and the processing returns.

On the other hand, when the first condition is not met, the processing advances to step S218 to determine whether or not the count value of counter EyeBlinkCnt, the value of flag EyeBlinkStartFlg and the count value of counter SelectedCnt meet values defined by the second condition. Here, to meet the second condition means that the relationships of the count value of counter EyeBlinkCnt≧1, the value of flag EyeBlinkStartFlg=1, and the count value of counter SelectedCnt<preset value are established. When the second condition is met, i.e., when the count value of counter EyeBlinkCnt is one or more, and the value of flag EyeBlinkStartFlg is one, blinks are detected to define the input of selected item. However, since the count value of counter SelectedCnt does not reach the preset value, it is judged that the selected item is not defined, and the processing advances to step S219. A vocal message indicating that the selection is not defined is set in the voice-output memory. Subsequently, the processing advances to step S225, the voice-output processing is performed so that the vocal message set in the voice-output memory is emitted from the speaker, and the processing returns.

Moreover, when the second condition is not met, the processing advances to step S220 to determine whether or not the count value of counter EyeBlinkCnt, the value of flag EyeBlinkStartFlg and the count value of counter SelectedCnt meet values defined by the third condition. Here, to meet the third condition means that the relationships of the count value of counter EyeBlinkCnt≧1, the value of flag EyeBlinkStartFlg=1, and the count value of counter SelectedCnt≧preset value are established. When the third condition is met, i.e., when the count value of counter SelectedCnt reaches the preset value, the selected item is defined. However, since the count value of counter EyeBlinkCnt is one or more, and the value of flag EyeBlinkStartFlg is one, it is judged that the input of the selected item can be defined after the eyes are kept closed for the predetermined time. The processing advances to step S221, and a vocal message indicating that the input can be defined after the eyes are closed for the predetermined time is set in the voice-output memory. Subsequently, the processing advances to step S225, the voice-output processing is performed so that the vocal message set in the voice output memory is emitted from the speaker, and the processing returns.

On the other hand, when the third condition is not met, the processing advances to step S222 to determine whether or not the count value of counter SelectedCnt meets a value defined by the fourth condition. Here, to meet the fourth condition means that the relationship of count value of counter SelectedCnt≧preset value is established. When the fourth condition is met, i.e., when the count value of counter SelectedCnt reaches the preset value, the selected item is defined. However, since the first and third conditions are not met, it is judged that the eyes are not closed, and the processing advances to step S223. A vocal message indicating that the character selection is defined is set in the voice output memory. Subsequently, the processing advances to step S225, the voice-output processing is performed so that the vocal message set in the voice-output memory is emitted from the speaker, and the processing returns.

When the fourth condition is not met, i.e., when the first to fourth conditions are not met, it is judged that the eyes are open. Moreover, since the relationship of the count value of counter SelectedCnt<preset value is satisfied, it is judged the item selection is not performed, and the processing advances to step S224. A vocal message indicating that the character selection is not performed is set in the voice-output memory. Subsequently, the processing advances to step S225, the voice-output processing is performed so that the vocal message set in the voice output memory is emitted from the speaker, and the processing returns.

As described above, in the embodiment, since the user is notified of the detection-result information by the vocal message, the same effect as the first embodiment can be obtained.

(c) Third Embodiment

Figure 10:
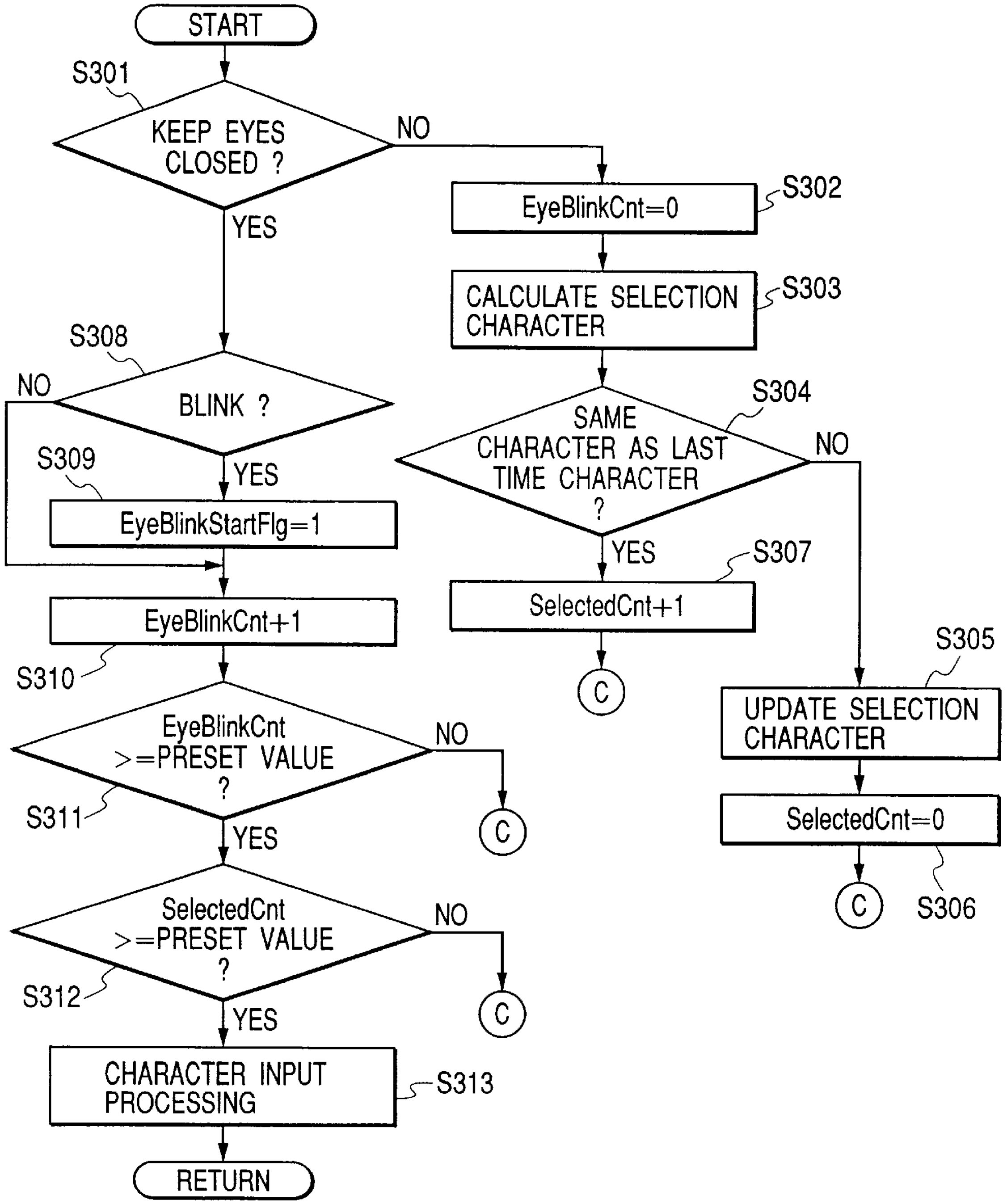
FIGS. 10 and 11 are flowcharts showing a procedure of visual-axis-detection-result-information-notification processing in the visual-axis input and decision-transfer device according to a third embodiment of the present invention.
Figure 11:
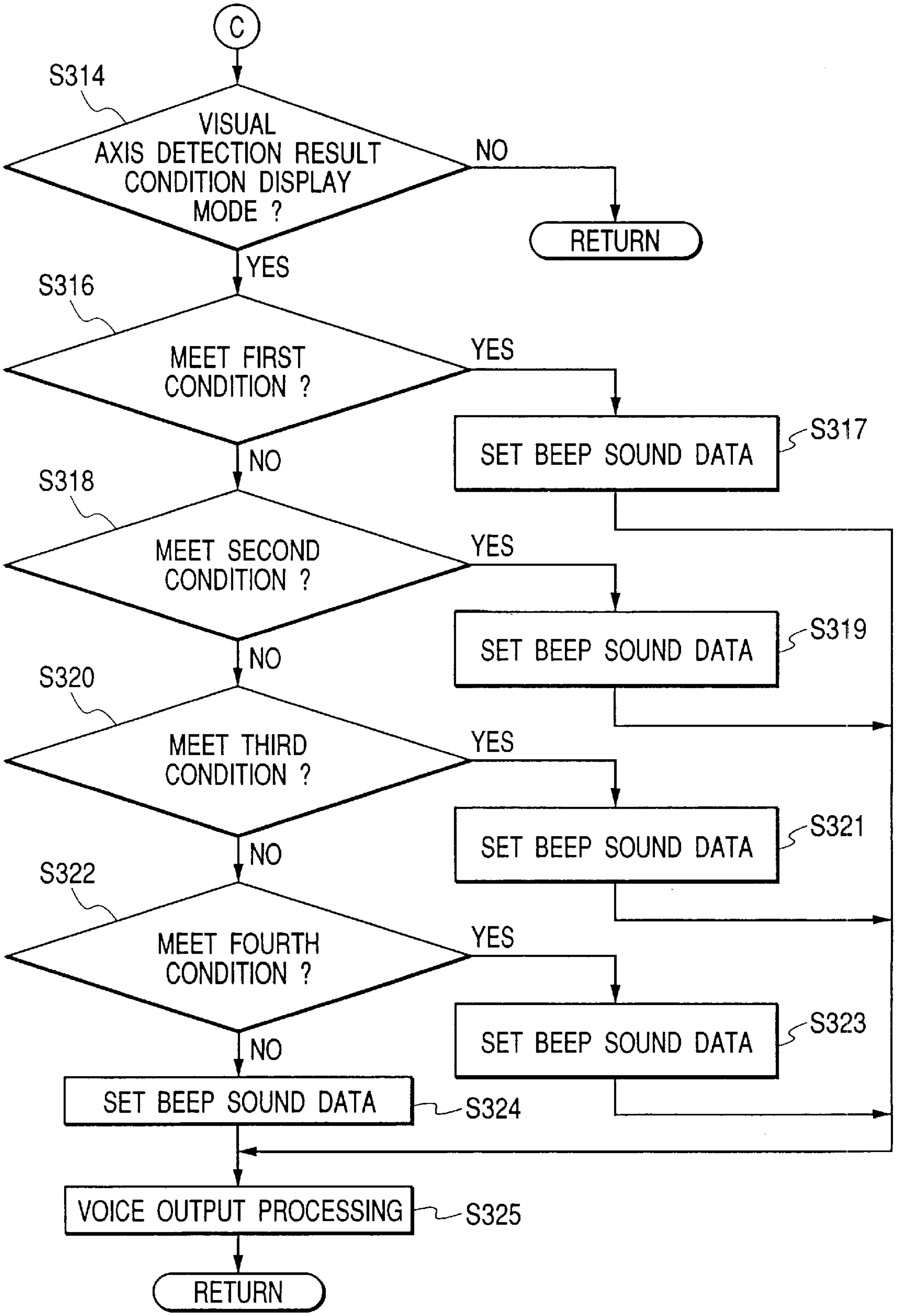

A third embodiment of the present invention will next be described with reference to FIGS. 10 and 11. FIGS. 10 and 11 are flowcharts showing the procedure of visual-axis-detection-result-information-notification processing in the visual-axis input and decision-transfer device according to the third embodiment of the present invention.

The embodiment is different from the first embodiment in that the user is notified of the detection-result information by a beep sound emitted from the speaker incorporated in the PC 1008. Additionally, the embodiment has the same constitution as the first embodiment, and the description thereof is omitted.

The procedure of the visual-axis-detection-result-information-notification processing will next be described with reference to FIGS. 10 and 11. Additionally, the processing of the embodiment is different from the second embodiment only in that notification is performed by the beep sound instead of the vocal message, and only the different portions are described. Moreover, since the processing of steps S301 to S313 shown in FIG. 10 is the same as that of the steps S201 to S213 in the second embodiment, the description thereof is omitted.

After the step S306 or S307 is executed, or when a negative response is made at the step S311 or S312, the processing advances to step S314. As shown in FIG. 11, it is determined at the step S314 whether or not the visual-axis-detection-result-condition-display mode is set. When the mode is not set, the processing returns. On the other hand, when the visual-axis-detection-result-condition-display mode is set, the processing advances to step S316 to determine whether or not the count value of counter EyeBlinkCnt and the value of flag EyeBlinkStartFlg meet values defined by the first condition. Here, to meet the first condition means that relationships of the count value of counter EyeBlinkCnt≧1, and the value of flag EyeBlinkStartFlg=0 are established. When the first condition is met, i.e., when the count value of counter EyeBlinkCnt is one or more, but the value of flag EyeBlinkStartFlg is zero, it is judged that the user keeps his eyes closed and no blink is detected. The processing advances to step S317, in which a beep sound indicating that the eyes are closed and no blink is detected is set in the voice-output memory. Subsequently, the processing advances to step S325, the voice output processing is performed so that the beep sound set in the voice output memory is emitted from the speaker, and the processing returns.

On the other hand, when the first condition is not met, the processing advances to step S318 to determine whether or not the count value of counter EyeBlinkCnt, value of flag EyeBlinkStartFlg and the count value of counter SelectedCnt meet values defined by the second condition. Here, to meet the second condition means that the relationships of the count value of counter EyeBlinkCnt≧1, the value of flag EyeBlinkStartFlg=1, and the count value of counter SelectedCnt<preset value are established. When the second condition is met, i.e., when the count value of counter EyeBlinkCnt is one or more, and the value of flag EyeBlinkStartFlg is one, blinks are detected to define the input of selected character. However, since the count value of counter SelectedCnt does not reach the preset value, it is judged that the selected character is not defined, and the processing advances to step S319. A beep sound indicating that the character selection is not defined is set in the voice output memory. Subsequently, the processing advances to step S325, the voice-output processing is performed so that the beep sound set in the voice-output memory is emitted from the speaker, and the processing returns.

Moreover, when the second condition is not met, the processing advances to step S320 to determine whether or not the count value of counter EyeBlinkCnt, the value of flag EyeBlinkStartFlg and the count value of counter SelectedCnt meet values defined by the third condition. Here, to meet the third condition means that the relationships of the count value of counter EyeBlinkCnt≧1, the value of flag EyeBlinkStartFlg=1, and the count value of counter SelectedCnt≧preset value are established. When the third condition is met, i.e., when the count value of counter SelectedCnt reaches the preset value, the selected character is defined. However, since the count value of counter EyeBlinkCnt is one or more, and the value of flag EyeBlinkStartFlg is one, it is judged that the input of the selected character can be defined after the eyes are kept closed for the predetermined time. The processing advances to step S321, and a beep sound indicating that the input can be defined after the eyes are closed for the predetermined time is set in the voice-output memory. Subsequently, the processing advances to step S325, the voice-output processing is performed so that the beep sound set in the voice-output memory is emitted from the speaker, and the processing returns.

On the other hand, when the third condition is not met, the processing advances to step S322 to determine whether or not the count value of counter SelectedCnt meets a value defined by the fourth condition. Here, to meet the fourth condition means that the relationship of the count value of counter SelectedCnt≧preset value is established. When the fourth condition is met, i.e., when the count value of counter SelectedCnt reaches the preset value, the selected character is defined. However, since the first and third conditions are not met, it is judged that the eyes are not closed, and the processing advances to step S323. A beep sound indicating that the character selection is defined is set in the voice-output memory. Subsequently, the processing advances to step S325, the voice-output processing is performed so that the beep sound set in the voice-output memory is emitted from the speaker, and the processing returns.

When the fourth condition is not met, i.e., when the first to fourth conditions are not met, it is judged that the eyes are open. Moreover, since the relationship of the count value of counter SelectedCnt<preset value is satisfied, it is judged that the item selection is not performed, and the processing advances to step S324. A beep sound indicating that the character selection is not performed is set in the voice-output memory. Subsequently, the processing advances to step S325, the voice-output processing is performed so that the beep sound set in the voice-output memory is emitted from the speaker, and the processing returns.

As described above, in the embodiment, since the user is notified of the detection-result information by the beep sound, the same effect as the second embodiment can be obtained.

(d) Fourth Embodiment

Figure 12:
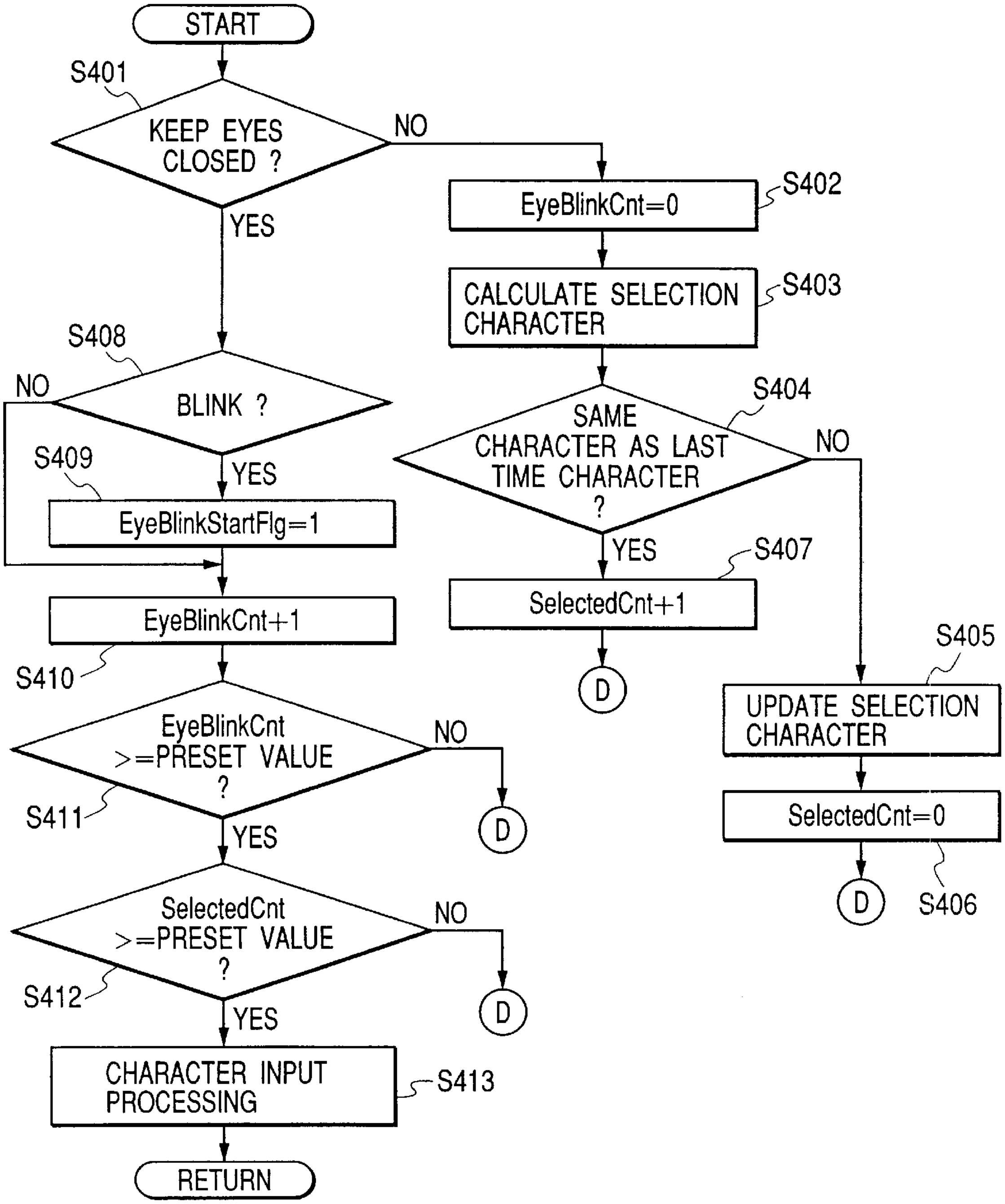
FIGS. 12 and 13 are flowcharts showing a procedure of visual-axis-detection-result-information-notification processing in the visual-axis input and decision-transfer device according to a fourth embodiment of the present invention.
Figure 13:
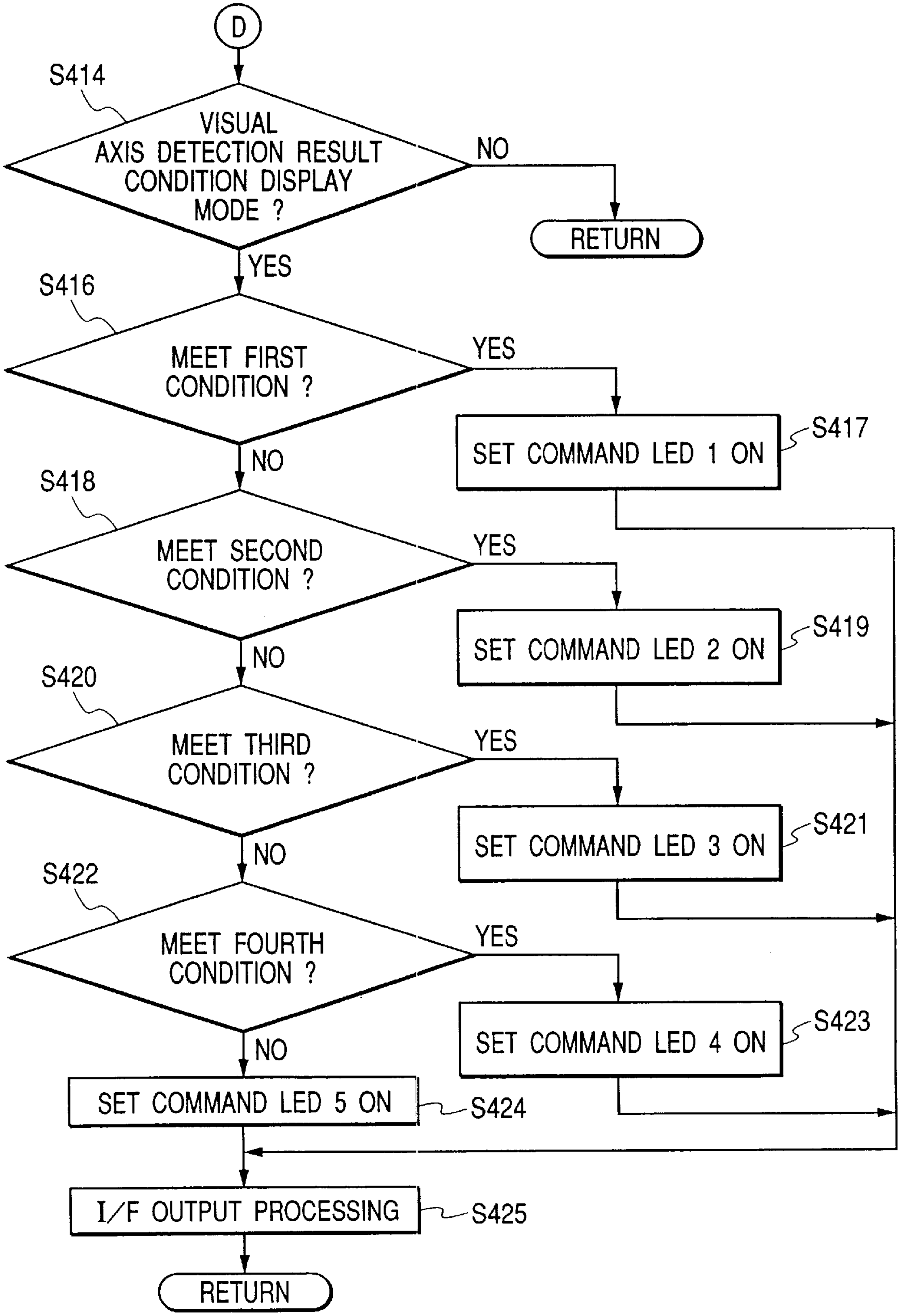

A fourth embodiment of the present invention will next be described with reference to FIGS. 12 and 13. FIGS. 12 and 13 are flowcharts showing the procedure of visual-axis-detection-result-information-notification processing in the visual-axis input and decision-transfer device according to the fourth embodiment of the present invention.

The embodiment is different from the first embodiment in that the user is notified of the detection result information by incorporating a plurality of light emitting diodes (not shown) into the head-mount display 1006 and controlling light emitting of the plurality of diodes. Additionally, the embodiment has the same constitution as the first embodiment, and the description thereof is omitted.

The procedure of the visual-axis-detection-result information-notification processing will next be described with reference to FIGS. 12 and 13. Additionally, the processing of the embodiment is different from the second embodiment only in that notification is performed by the light emitting state of the plurality of diodes emitting visible rays instead of the vocal message, and only the different portions are described. Moreover, since the processing of steps S401 to S413 shown in FIG. 12 is the same as that of the steps S201 to S213 in the second embodiment, the description thereof is omitted.

After the step S406 or S407 is executed, or when a negative response is made at the step S411 or S412, the processing advances to step S414. As shown in FIG. 13, it is determined at the step S414 whether or not the visual-axis-detection-result-condition-display mode is set. When the mode is not set, the processing returns. On the other hand, when the visual-axis-detection-result-condition-display mode is set, the processing advances to step S416 to determine whether or not the count value of counter EyeBlinkCnt and the value of flag EyeBlinkStartFlg meet values defined by the first condition. Here, to meet the first condition means that the relationships of the count value of counter EyeBlinkCnt≧1, and the value of flag EyeBlinkStartFlg=0 are established. When the first condition is met, i.e., when the count value of counter EyeBlinkCnt is one or more, but the value of flag EyeBlinkStartFlg is zero, it is judged that the user keeps his eyes closed and no blink is detected. The processing advances to step S417, in which a command for turning on a light emitting diode LED 1 is set in I/F output memory to indicate that the eyes are closed and no blink is detected. Subsequently, the processing advances to step S425, the command for turning on the LED 1 is outputted from the I/F output memory, and the processing returns. Here, when the LED 1 is turned on in response to the ON command, the user is notified that the eyes are closed and no blink is detected.

On the other hand, when the first condition is not met, the processing advances to step S418 to determine whether or not the count value of counter EyeBlinkCnt, the value of flag EyeBlinkStartFlg and count value of counter SelectedCnt meet values defined by the second condition. Here, to meet the second condition means that the relationships of the count value of counter EyeBlinkCnt>1, the value of flag EyeBlinkStartFlg=1, and the count value of counter SelectedCnt<preset value are established. When the second condition is met, i.e., when the count value of counter EyeBlinkCnt is one or more, and the value of flag EyeBlinkStartFlg is one, blinks are detected to define the input of selected character. However, since the count value of counter SelectedCnt does not reach the preset value, it is judged that the selected character is not defined, and the processing advances to step S419. A command for turning on a light emitting diode LED 2 is set in I/F output memory to indicate that the character selection is not defined. Subsequently, the processing advances to step S425, the command for turning on the LED 2 is transmitted to LED 2 from the I/F output memory, and the processing returns. Here, when the LED 2 is turned on in response to the ON command, the user is notified that the character selection is not defined.

Moreover, when the second condition is not met, the processing advances to step S420 to determine whether or not the count value of counter EyeBlinkCnt, the value of flag EyeBlinkStartFlg, and the count value of counter SelectedCnt meet values defined by the third condition. Here, to meet the third condition means that the relationships of the count value of counter EyeBlinkCnt≧1, the value of flag EyeBlinkStartFlg=1, and the count value of counter SelectedCnt≧preset value are established. When the third condition is met, i.e., when the count value of counter SelectedCnt reaches the preset value, the selected character is defined. However, since the count value of counter EyeBlinkCnt is one or more, and the value of flag EyeBlinkStartFlg is one, it is judged that the input of the selected character can be defined after the eyes are kept closed for the predetermined time. The processing advances to step S421, and a command for turning on a light emitting diode LED 3 is set in I/F output memory to indicate that the input can be defined after the eyes are closed for the predetermined time.

Subsequently, the processing advances to step S425, an ON command is transmitted to the LED 3 from the I/F output memory, and the processing returns. Here, when the LED 3 is turned on in response to the ON command, the user is notified that if the eyes are closed for the predetermined time, the input can be defined.

On the other hand, when the third condition is not met, the processing advances to step S422 to determine whether or not the count value of counter SelectedCnt meets a value defined by the fourth condition. Here, to meet the fourth condition means that the relationship of the count value of counter SelectedCnt≧preset value is established. When the fourth condition is met, i.e., when the count value of counter SelectedCnt reaches the preset value, the selected character is defined. However, since the first and third conditions are not met, it is judged that the eyes are not closed, and the processing advances to step S423. A command for turning on a light emitting diode LED 4 is set in I/F output memory to indicate that character selection is defined. Subsequently, the processing advances to step S425, an ON command is transmitted to the LED 4 from the I/F output memory, and the processing returns. Here, when the LED 4 is turned on in response to the ON command, the user is notified that the character selection is defined.

When the fourth condition is not met, i.e., when the first to fourth conditions are not met, it is judged that the eyes are open. Moreover, since the relationship of the count value of counter SelectedCnt<preset value is satisfied, it is judged the character selection is not performed, and the processing advances to step S424. An ON command for a light emitting diode LED 5 is set in I/F output memory to indicate that the character selection is not performed. Subsequently, the processing advances to step S425, the ON command is transmitted to the LED 5 from the I/F output memory, and the processing returns. Here, when the LED 5 is turned on in response to the ON command, the user is notified that the character selection is not performed.

As described above, in the embodiment, since the user is notified of the detection-result information is by the lighting state of LED 1 to 5, the same effect as the first embodiment can be obtained.

(e) Fifth Embodiment

Figure 14:
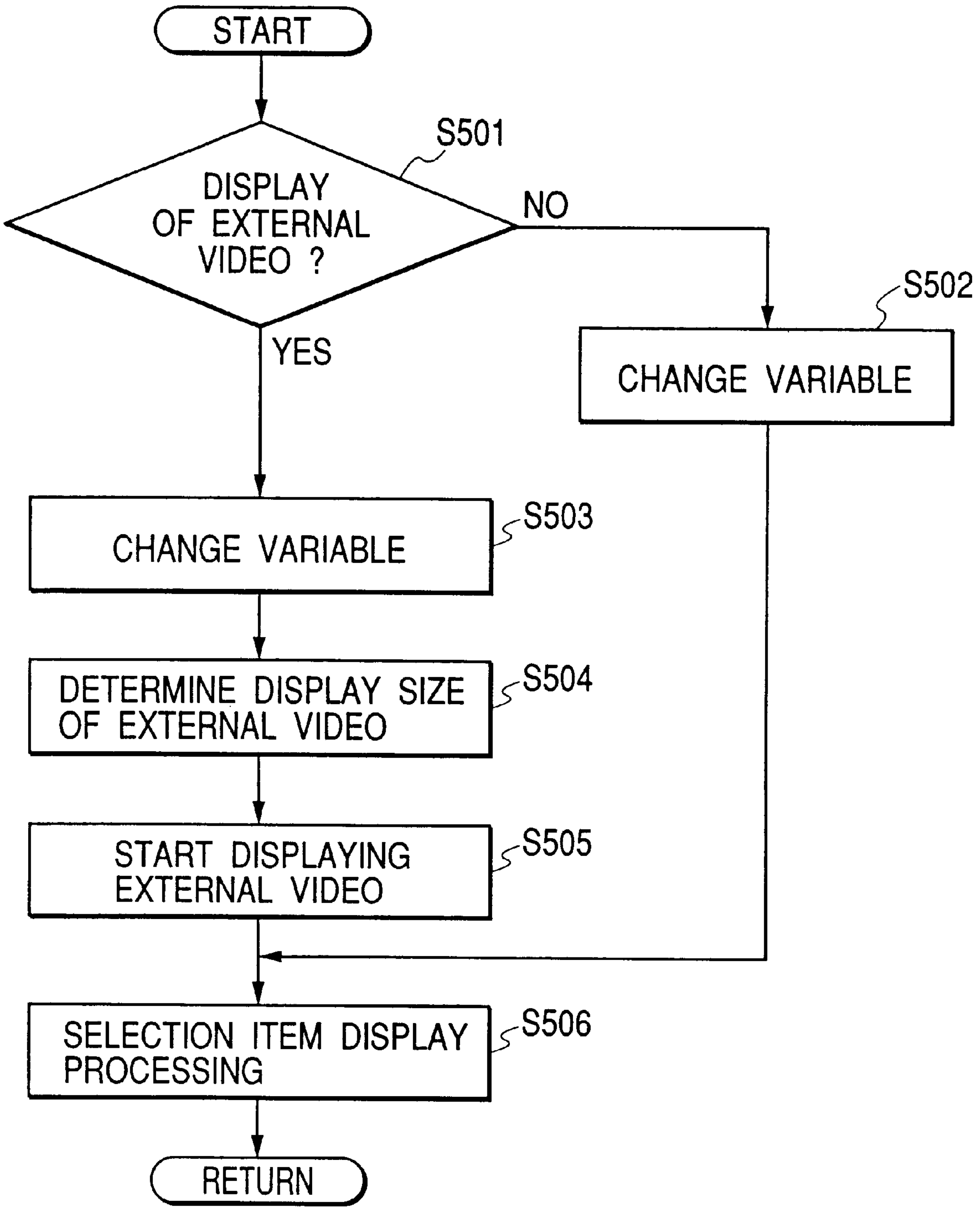
FIG. 14 is a flowchart showing a procedure of external video display processing in the visual-axis input and decision-transfer device according to a fifth embodiment of the present invention.
Figure 15:
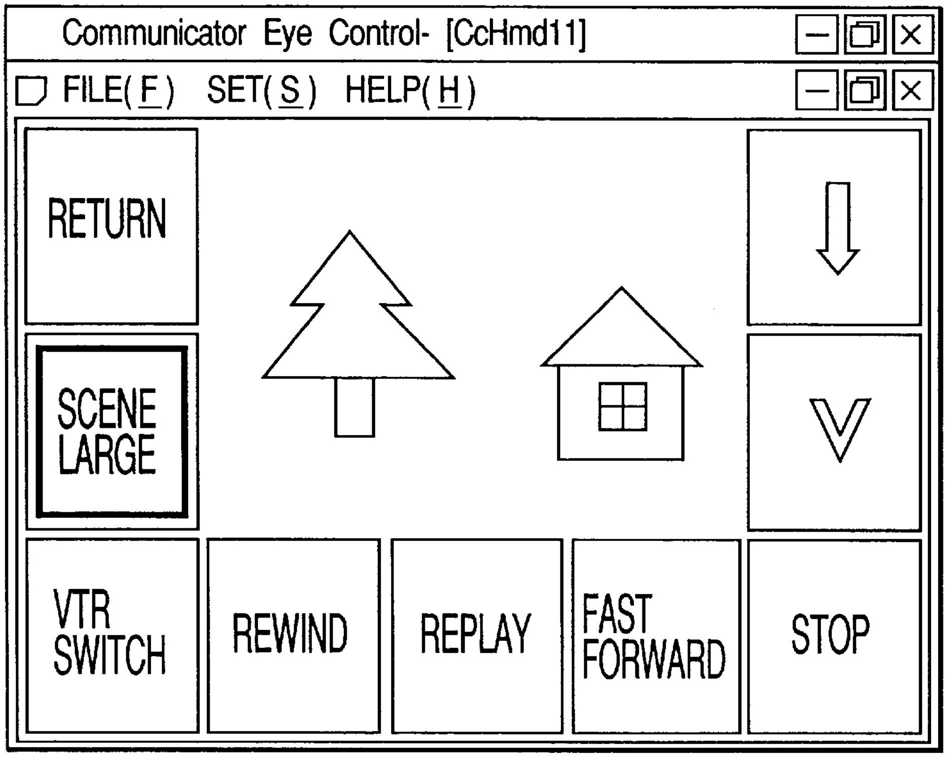
FIGS. 15 and 16 are views showing examples of screen a displayed in a head-mount display by the external video-display processing of FIG. 14.
Figure 16:
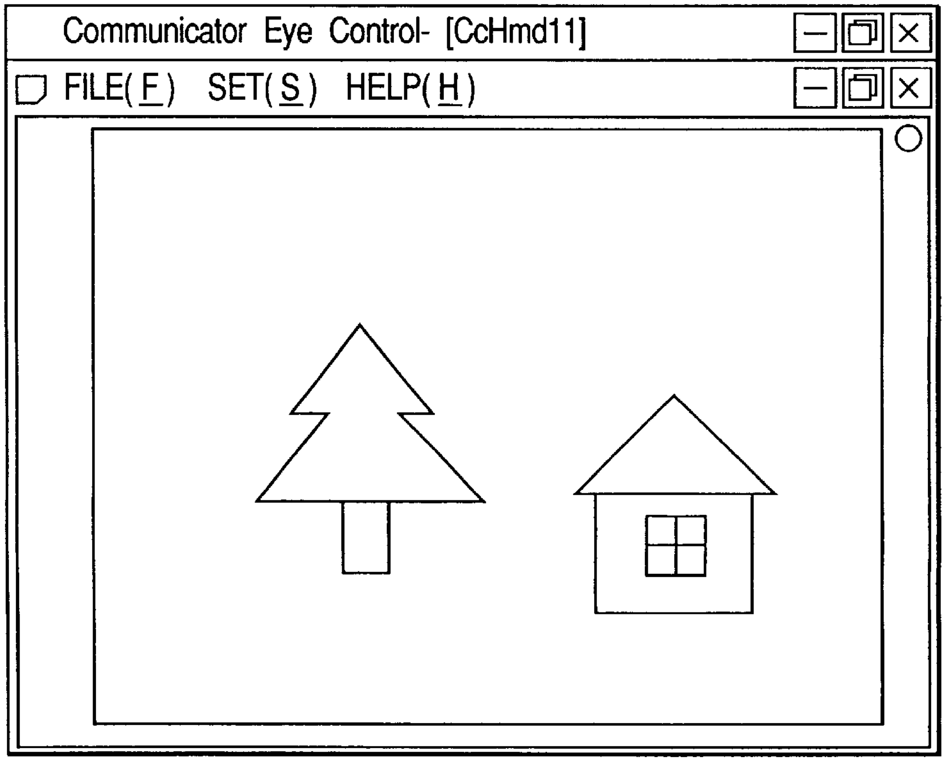

A fifth embodiment of the present invention will next be described with reference to FIGS. 14 to 16. FIG. 14 is a flowchart showing a procedure of external video-display processing in the visual-axis input and decision-transfer device according to the fifth embodiment of the present invention. FIGS. 15 and 16 are views showing examples of screen displayed in the head-mount display by the external video-display processing of FIG. 14.

In the embodiment, the PC 1008 comprises an interface for taking video from an external source to perform a display processing in which the taken external video and display panel indicative of selection items selectable by visual-axis input are arranged and displayed in the liquid-crystal display element 1002 of head-mount display 1006. Additionally, a rate of display areas of the external video and display panel in the liquid-crystal display element 1002 of head-mount display 1006 is arbitrarily set based on user's instruction.

A procedure of external video-display processing in the embodiment will next be described with reference to FIG. 14.

First, in step S501, it is determined whether or not the external video is displayed. When the external video is not displayed, the processing advances to step S502, in which a variable indicating the rate of display areas of external video and display panel in the liquid-crystal display element 1002 is changed to a value for displaying only the display panel. The processing then advances to step S506 for displaying the selection items on the display panel, and returns.

On the other hand, when the display of external video is determined at the step S501, the processing advances to step S503, in which the rate of display areas of external video and the display panel in the liquid-crystal display element 1002 is changed to a desired value. Subsequently, at step S504 a display size of external video is determined based on the rate set in the step S503. Subsequently, the processing advances to step S505, in which control of the liquid-crystal display circuit 1007 is started to start displaying the external video in the liquid-crystal display element 1002. Subsequently, at step S506 the selection items are displayed in the area other than the display area of the external video, and the processing returns.

For example, a screen shown in FIG. 15 is displayed for the user through the aforementioned processing. In the screen shown in FIG. 15, when the external video is further enlarged and displayed, an icon "SCENE LARGE" is selected by the visual axis input. Through the selection, as shown in FIG. 16, the external video is enlarged and displayed in the entire display area of the liquid crystal display element 1002. In this case, no selection item is displayed, and only an icon (round button on the upper right of the screen) is displayed for returning the enlarged screen displaying the enlarged external video back to FIG. 15.

Therefore, in the embodiment, the external video transmitted from outside can be seen while looking at the selection items.

(f) Sixth Embodiment

Figure 17:
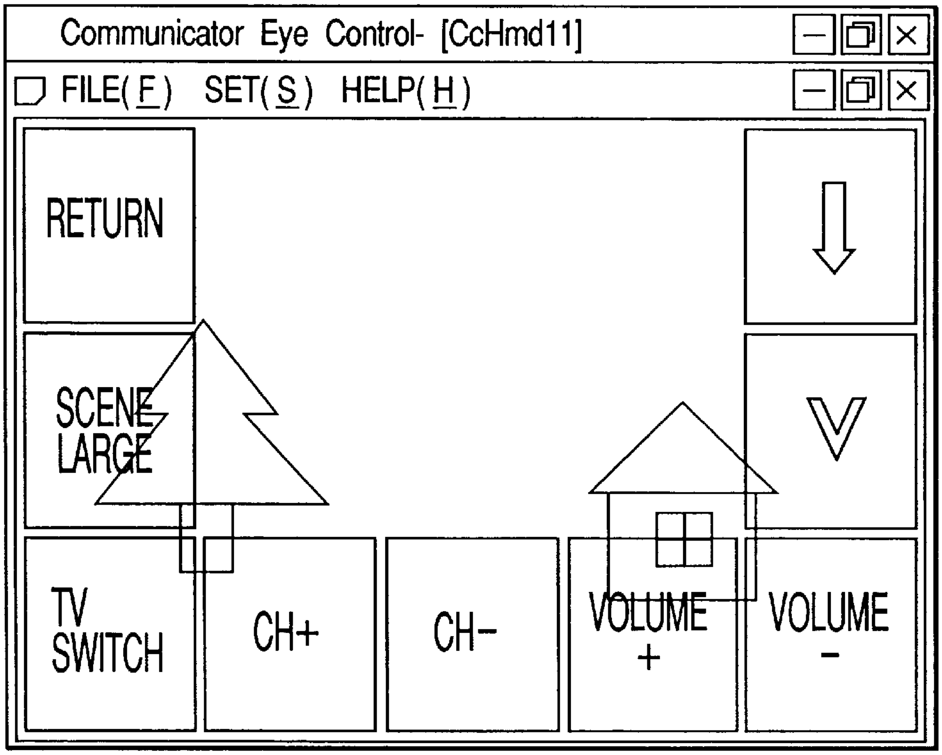
FIGS. 17, 18 and 19 are views showing examples of a screen displayed in the head mount display by a video-display processing in the visual-axis input and decision-transfer device according to a sixth embodiment of the present invention.
Figure 18:
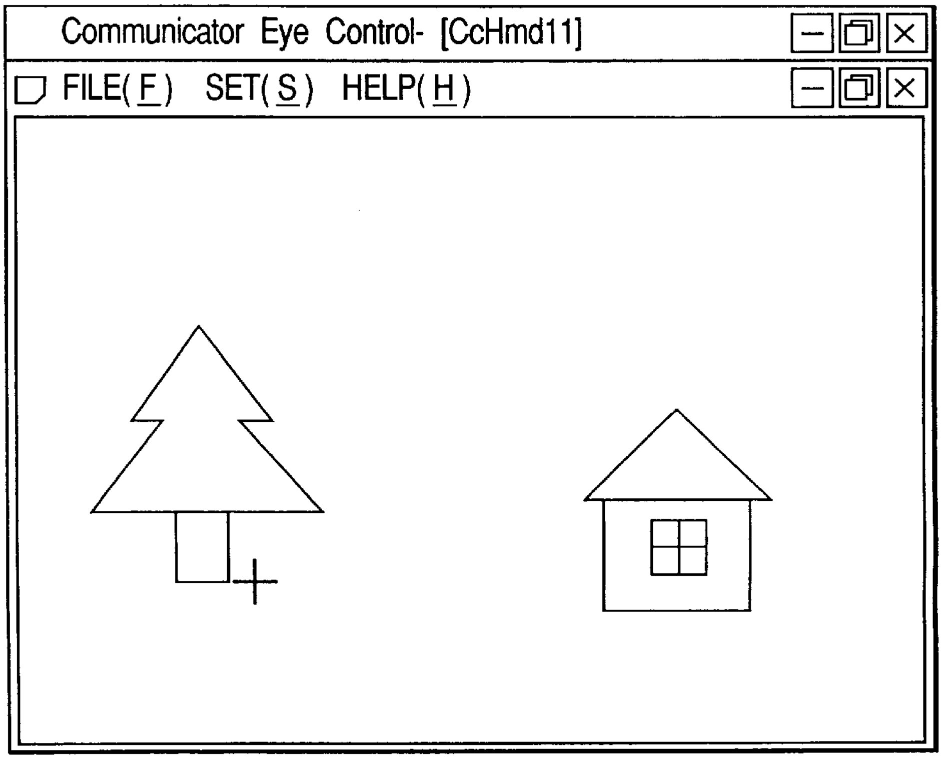
Figure 19:
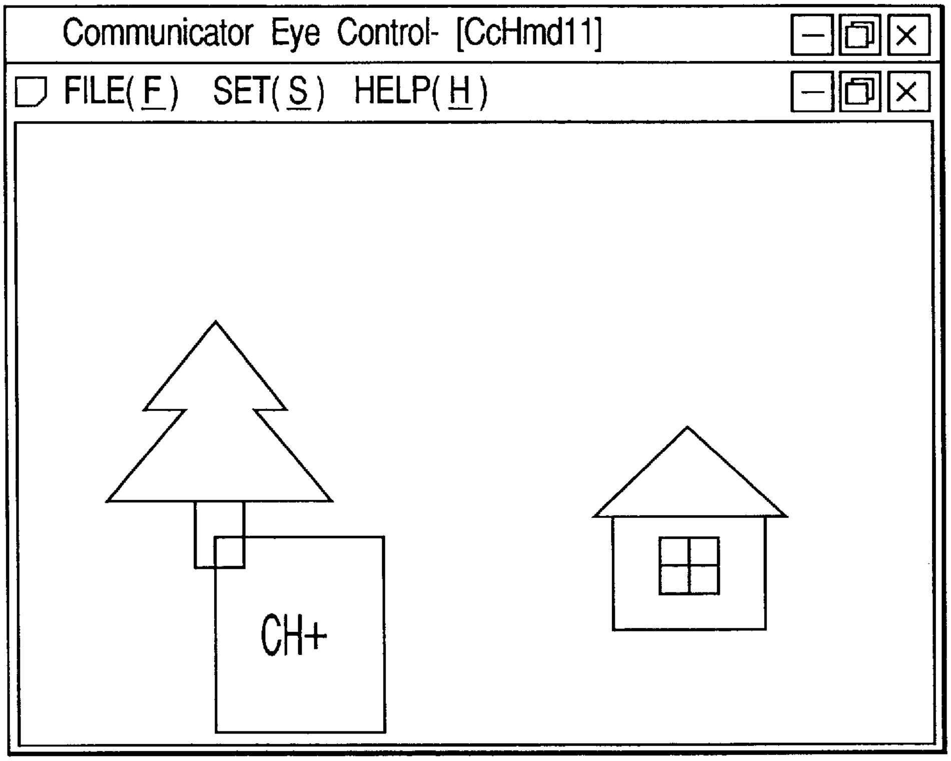

A sixth embodiment of the present invention will next be described with reference to FIGS. 17 to 19. FIGS. 17 to 19 are views showing examples of a screen displayed in the head-mount display by video-display processing in the visual-axis input and decision-transfer device according to the sixth embodiment of the present invention.

In the embodiment, the PC 1008 comprises the interface for taking video from an external source to perform a display processing in which the display panel indicating the selection items selectable by the visual-axis input is overlapped and displayed on the taken external video in the liquid-crystal display element 1002 of head-mount display 1006. Additionally, it can be selected whether or not the external video and selection items are overlapped for the display. Moreover, in the screen displaying only the external video, when a certain position on the external video is selected by the visual-axis input, it is determined whether or not the position selected by the visual-axis input is a display position of selection item. When the position inputted by the visual-axis input is the display position of the selection item, the selection item corresponding to the position is overlapped and displayed on the external video.

In the display processing of the embodiment, for example, the external video and selection items can be overlapped and displayed as shown in FIG. 17.

Moreover, as shown in FIG. 18, in the screen in which only the external video is displayed, when a certain position on the external video (mark x in the drawing) is selected by the visual-axis input, it is determined whether the position selected by the visual-axis input is a display position of selection item. Here, when the position inputted by the visual-axis input is a display position of selection item CH+, as shown in FIG. 19, the selection item CH+ is overlapped and displayed on the external video. The selection item is inputted by selecting the selection item by the visual-axis input, and the corresponding processing is executed.

Therefore, in the embodiment, the selection item can be selected by the visual axis input while looking at the external video transmitted from outside.

(g) Seventh Embodiment

A seventh embodiment of the present invention will next be described with reference to FIGS. 20 to 23. FIGS. 20 to 23 are views showing examples of screen displayed in the head-mount display by the video display processing in the visual-axis input and decision-transfer device according to the seventh embodiment of the present invention.

In a display processing of the embodiment, a display mode of selection item displayed in the liquid-crystal display element 1002 of head-mount display 1006 is changed and displayed.

Figure 20:
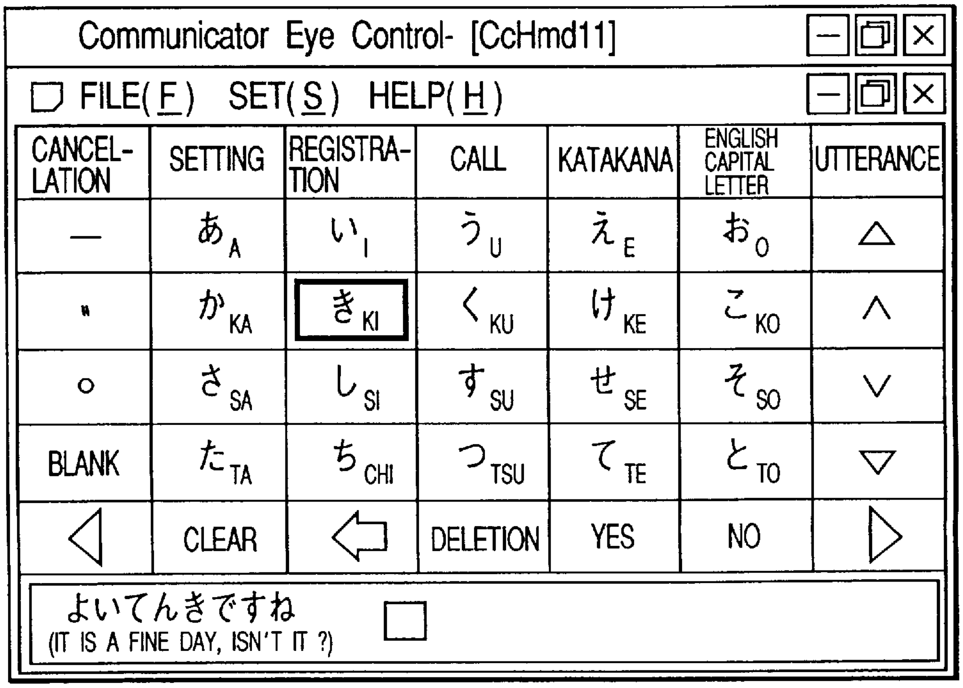
Figure 22:
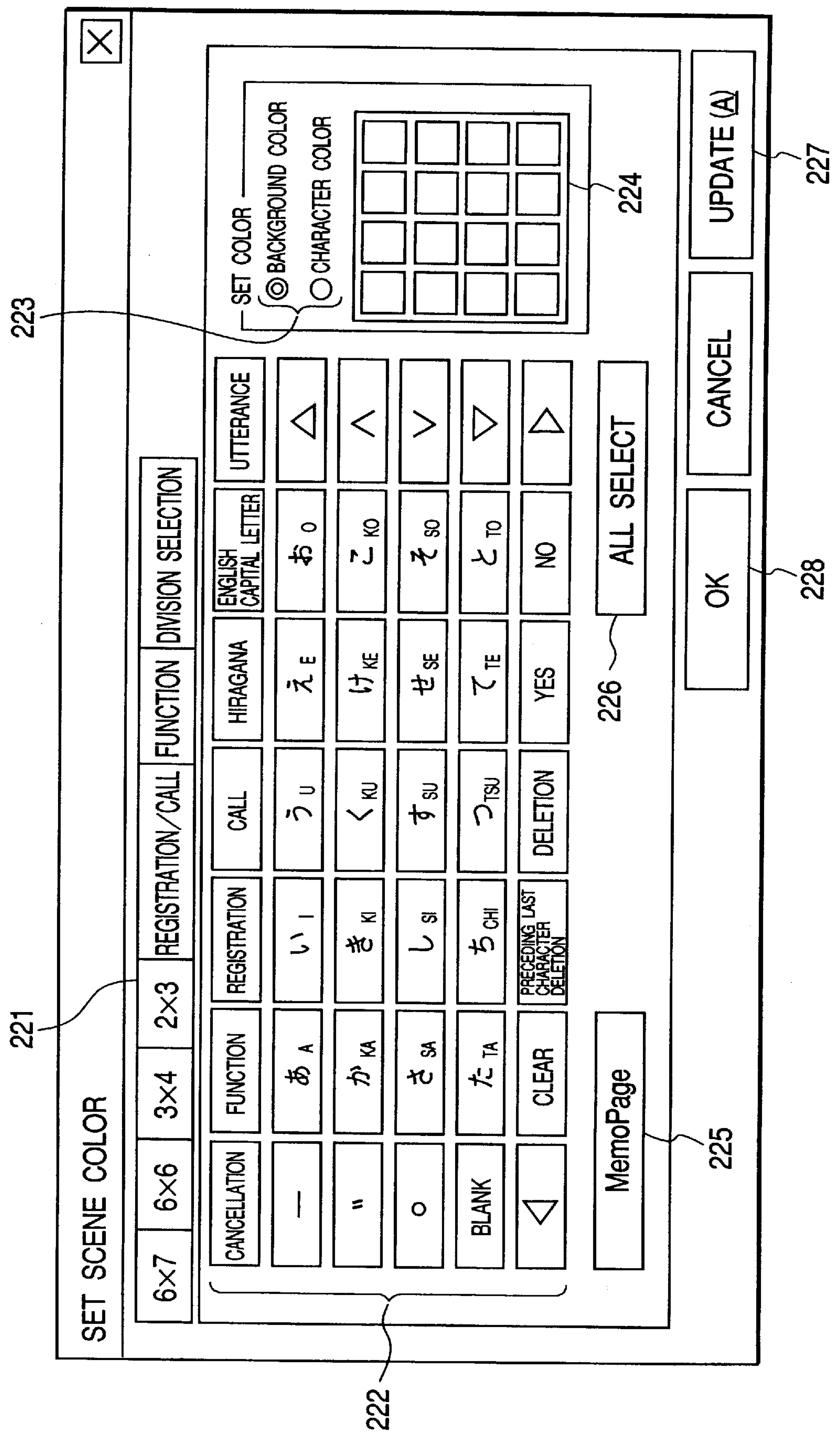

In the display processing of the embodiment, for example, as shown in FIG. 20, when the display mode of selection item displayed in the head-mount display 1006 is changed, the setting menu is selected on the screen to open a menu screen shown in FIG. 21. When SET SCENE COLOR is selected in the menu screen, a dialog box SET SCENE COLOR shown in FIG. 22 is open, a scene is selected with a scene selection tag 221 in the dialog box, and an item whose color is to be changed is indicated by input of selection buttons 222. Subsequently, a background or character color to be changed is indicated with check button BACKGROUND COLOR/CHARACTER COLOR 223 in SET COLOR, and a color after the change is designated using color buttons 224.

Moreover, in order to change a color of a memo page display, after a button MemoPage 225 is selected, the background or character color to be changed is indicated using the button BACKGROUND COLOR/CHARACTER COLOR 223 in SET COLOR, the color after the change is designated with the color button 224, and the selection button 222 is inputted.

Furthermore, all the selection items and the memo page display area in the selection screen are changed to one color, button ALL SELECT 226 is selected, the background or character color to be selected is instructed with the check button BACKGROUND COLOR/CHARACTER COLOR 223 in SET COLOR, and the color after the change is designated with the color button 224. When the change to the desired color is set, the display color of the selection item displayed in the head mount display 1006 is changed and displayed by pressing button UPDATE 227. Furthermore, the display color of the selection item displayed in the head mount display 1006 is changed and displayed by pressing button OK 228 to complete the dialog box SET SCENE COLOR without pressing the button UPDATE 227.

Here, for example, when the dialog box SET SCENE COLOR is used to change a color of character A in the selection items to black and change its background color to white, a screen shown in FIG. 23 is displayed in the head-mount display 1006.

As described above, in the embodiment, the selection item can be displayed in such a manner that the user can easily perform a visual check.

(h) Eighth Embodiment

Figure 25:
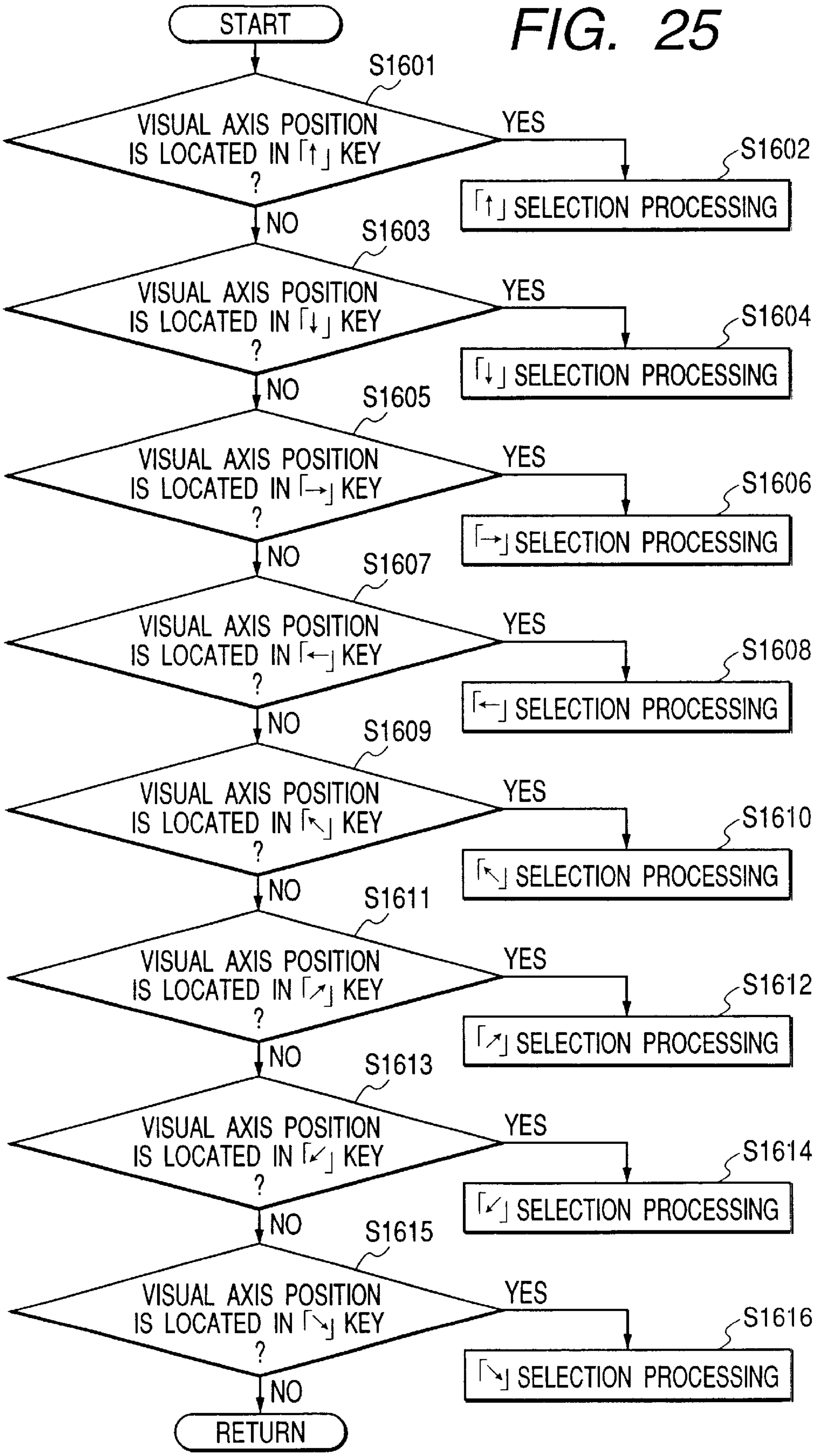
FIG. 25 is a flowchart of a procedure of the selection processing in the visual-axis input and decision transfer device according to the eighth embodiment.

An eighth embodiment of the present invention will next be described with reference to FIGS. 24 to 33. FIG. 24 is a view showing an example of a selection screen displayed in the head mount display by a selection processing, and FIG. 25 is a flowchart of a procedure of the selection processing in the visual-axis input and decision-transfer device according to the eighth embodiment of the present invention. FIGS. 26 to 33 are flowcharts showing an upward arrow-mark selection processing of step S1602, downward arrow-mark selection processing of step S1604, rightward arrow-mark selection processing of step S1606, leftward arrow-mark selection processing of step S1608, left upward arrow-mark selection processing of step S1610, right upward arrow-mark selection processing of step S1612, left downward arrow-mark selection processing of step S1614, and right downward arrow-mark selection processing of step S1616 of FIG. 25, respectively.

In the embodiment, a processing is performed for selecting one selection item by a plurality of visual-axis inputs. Specifically, as shown in FIG. 24, in the selection screen, selection items are arranged in a central portion, while upward, downward, leftward, rightward, left upward, left downward, right upward, and right downward arrow-marks are arranged in a periphery. The user selects these arrow-mark keys of eight directions by visual-axis input, moves a selection frame to a desired character or item position, and performs the visual-axis input satisfying visual-axis input confirmation conditions in the position, so that a character or an item present in the position is selected and inputted.

The procedure of the selection processing using the selection screen will next be described with reference to FIG. 25. First at step S1601, it is determined whether or not a visual-axis position on the selection screen displayed in the head-mount display 1006 is located in a position of upward arrow-mark key. When the visual axis position is in the upward arrow-mark key, the processing advances to step S1602 to perform the upward arrow-mark selection processing. When the visual-axis position is not in the upward arrow-mark key, the processing advances to step S1603 to determine whether or not the visual-axis position on the selection screen is located in a position of downward arrow-mark key. When the visual-axis position is in the downward arrow-mark key, the processing advances to step S1604 to perform the downward arrow-mark selection processing. When the visual-axis position is not in the downward arrow-mark key, the processing advances to step S1605 to determine whether or not the visual-axis position on the selection screen is located in a position of rightward arrow-mark key. When the visual-axis position is in the rightward arrow-mark key, the processing advances to step S1606 to perform the rightward arrow-mark selection processing. When the visual-axis position is not in the rightward arrow-mark key, the processing advances to step S1607 to determine whether or not the visual-axis position on the selection screen is located in a position of leftward arrow-mark key. When the visual-axis position in the selection screen is in the leftward arrow-mark key, the processing advances to step S1608 to perform the leftward arrow-mark selection processing. When the visual-axis position is not in the leftward arrow-mark key, the processing advances to step S1609 to determine whether or not the visual-axis position on the selection screen is located in a position of left upward arrow mark key. When the visual-axis position is in the left upward arrow-mark key, the processing advances to step S1610 to perform the left upward arrow-mark selection processing. When the visual-axis position is not in the left upward arrow-mark key, the processing advances to step S1611 to determine whether or not the visual-axis position on the selection screen is located in a position of right upward arrow-mark key. When the visual-axis position is in the right upward arrow-mark key, the processing advances to step S1612 to perform the right upward arrow-mark selection processing. When the visual-axis position is not in the right upward arrow-mark key, the processing advances to step S1613 to determine whether or not the visual-axis position on the selection screen is located in a position of left downward arrow-mark key. When the visual-axis position is in the left downward arrow-mark key, the processing advances to step S1614 to perform the left downward arrow-mark selection processing. When the visual-axis position is not in the left downward arrow-mark key, the processing advances to step S1615 to determine whether or not the visual-axis position on the selection screen is located in a position of right downward arrow-mark key. When the visual-axis position is in the right downward arrow-mark key, the processing advances to step S1616 to perform the right downward arrow-mark selection processing. When the visual-axis position is not in the right downward arrow-mark key, it is judged that the visual-axis position is not in any of the direction arrow-mark keys, and the processing returns.

Figure 26:
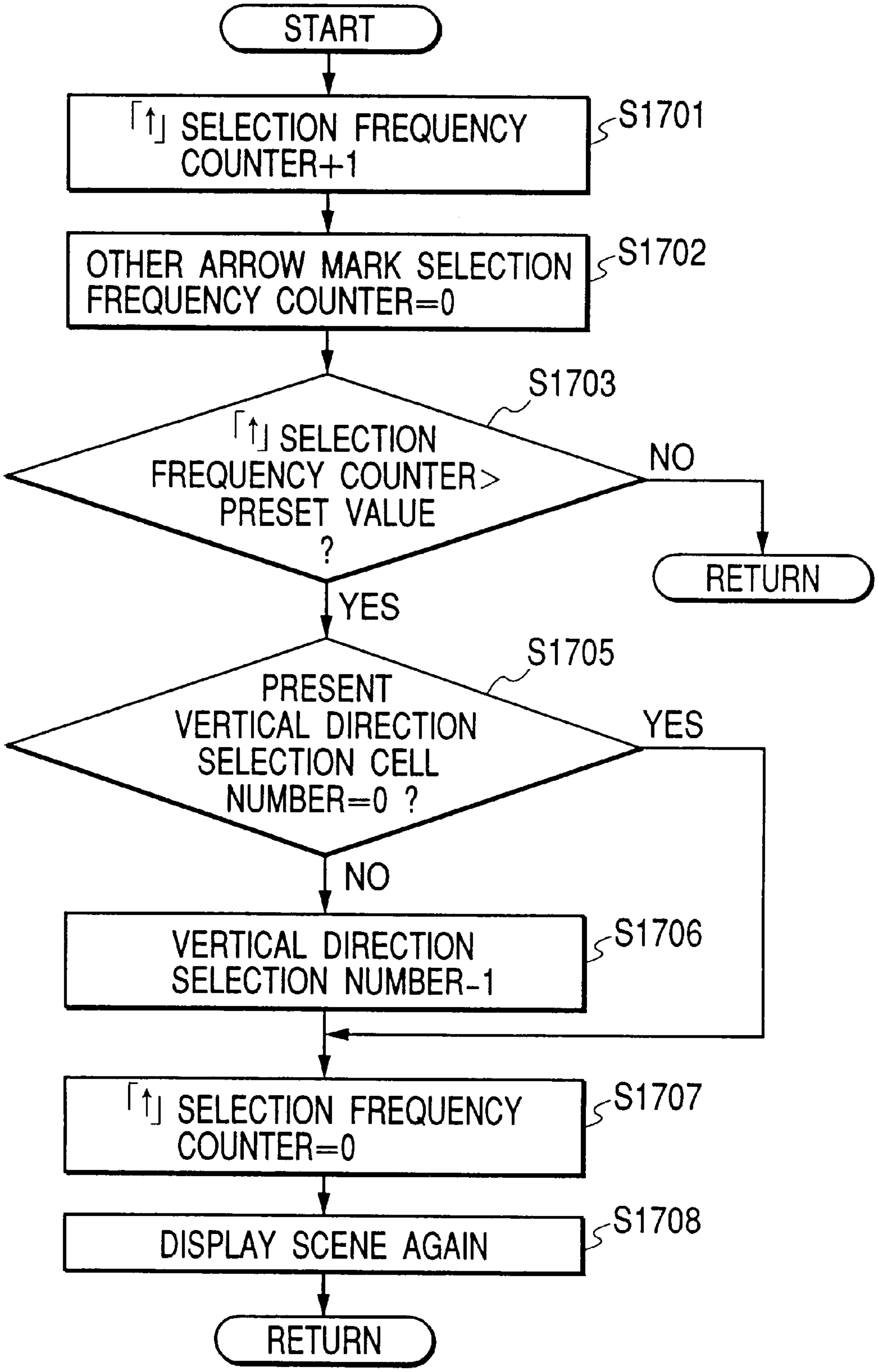
FIG. 26 is a flowchart of an upward arrow-mark selection processing of step S1602 of FIG. 25.

The upward arrow-mark selection processing will next be described with reference to FIG. 26. In the upward arrow-mark selection processing, first at step S1701, an upward arrow-mark-selection-frequency counter is incremented by one. Subsequently, at step S1702, other arrow-mark-selection-frequency counters are reset to zero. Subsequently, the processing advances to step S1703 to determine whether or not a value of upward arrow-mark-selection-frequency counter is equal to or more than a preset value. When the value of the upward arrow-mark-selection-frequency counter is less than the preset value, the processing returns. When the value of the upward arrow-mark-selection-frequency counter is equal to or more than the preset value, the processing advances to step S1705 to determine whether or not present vertical-direction selection cell number is zero, i.e., whether or not the present selected item is in an uppermost cell position. When the present selected item is not in the uppermost cell position, the processing advances to step S1706 to decrement a vertical-direction selection cell number by one, then advances to step S1707. On the other hand, when the present selected item is in the uppermost cell position, the processing skips the step S1706 and advances to the step S1707.

At the step S1707, the upward arrow-mark-selection-frequency counter is reset to zero. Subsequently at step S1708, the scene is displayed again, and the processing returns.

Figure 27:
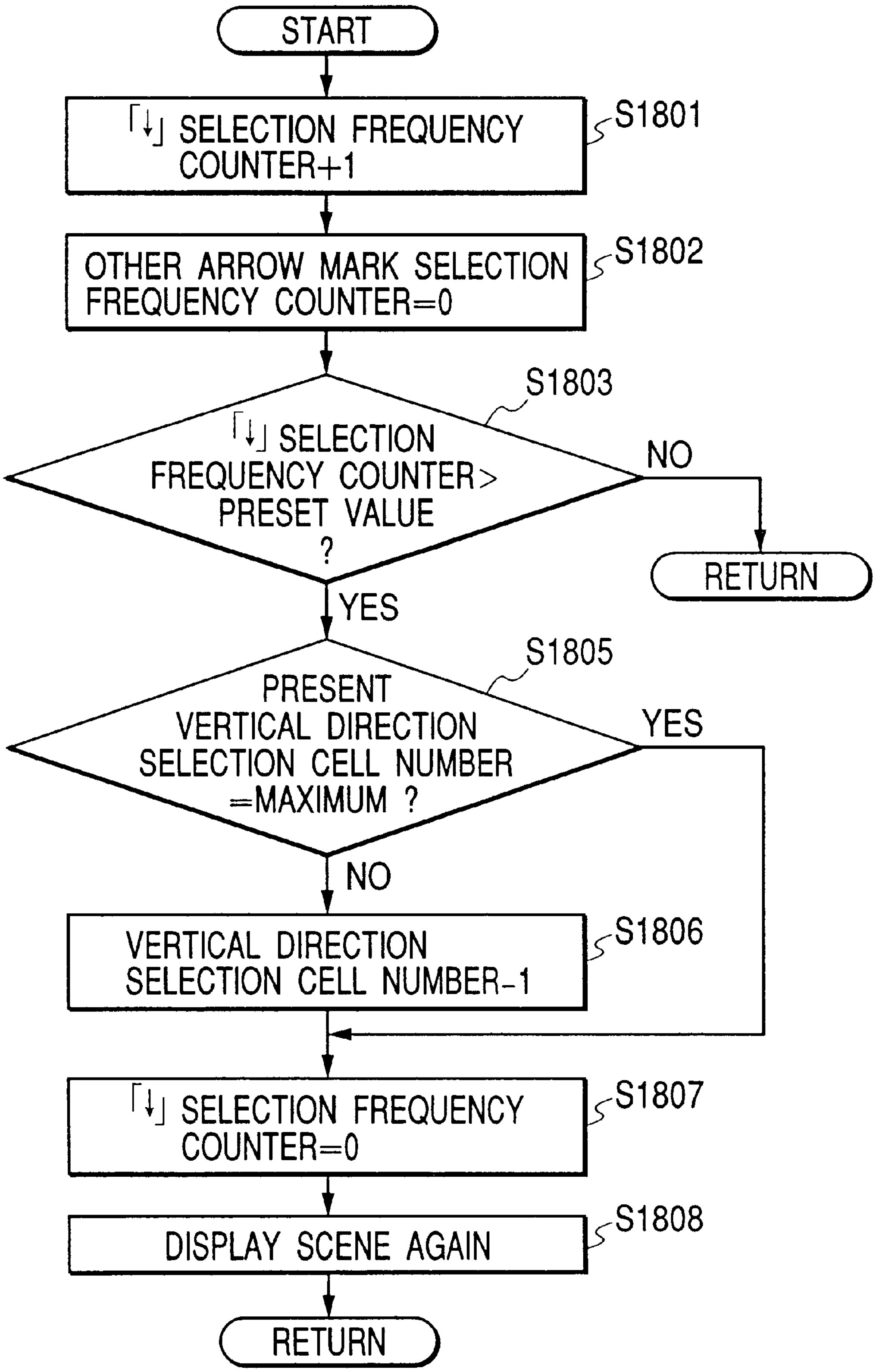
FIG. 27 is a flowchart of a downward arrow-mark selection processing of step S1604 of FIG. 25.

The downward arrow-mark selection processing will next be described with reference to FIG. 27. In the downward arrow-mark selection processing, first at step S1801, a downward arrow-mark-selection-frequency counter is incremented by one. Subsequently, at step S1802, other arrow-mark-selection-frequency counters are reset to zero. Subsequently, the processing advances to step S1803 to determine whether or not a value of downward arrow-mark selection-frequency-counter is equal to or more than a preset value. When the value of downward arrow-mark-selection-frequency counter is less than the preset value, the processing returns. When the value of downward arrow-mark-selection-frequency counter is equal to or more than the preset value, the processing advances to step S1805 to determine whether or not present vertical-direction selection cell number is a maximum, i.e., whether or not the present selected item is in a lowermost cell position. When the present selected item is not in the lowermost cell position, the processing advances to step S1806 to decrement a vertical-direction selection cell number by one, then advances to step S1807. On the other hand, when the present selected item is in the lowermost cell position, the processing skips the step S1806 and advances to the step S1807.

At the step S1807, the downward arrow-mark-selection-frequency counter is reset to zero. Subsequently at step S1808, the scene is displayed again, and the processing returns.

Figure 28:
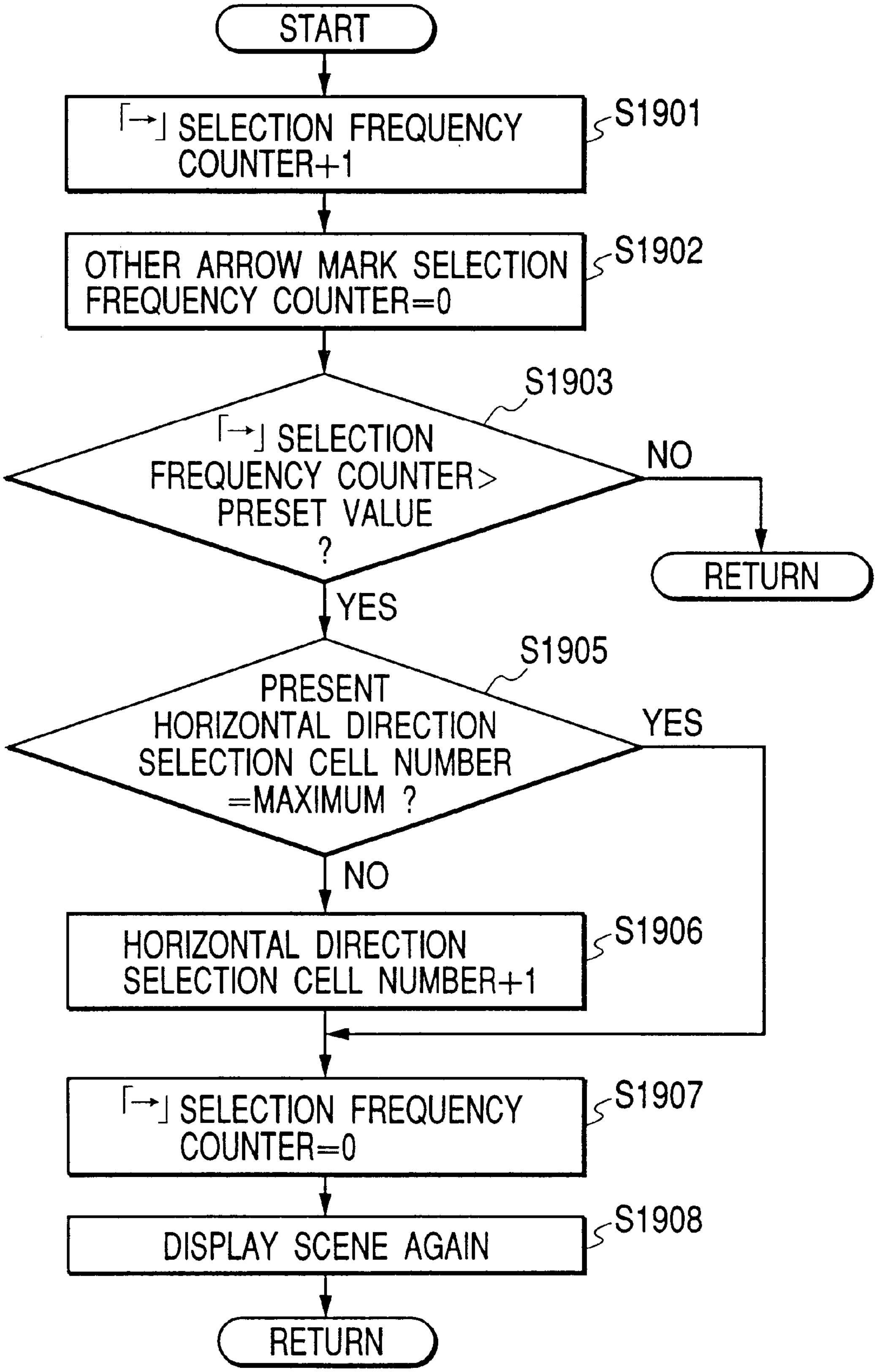
FIG. 28 is a flowchart of a rightward arrow-mark selection processing of step S1606 of FIG. 25.

The rightward arrow-mark selection processing will next be described with reference to FIG. 28. In the rightward arrow-mark selection processing, first at step S1901, a rightward arrow-mark-selection-frequency counter is incremented by one. Subsequently, at step S1902, other arrow-mark-selection-frequency counters are reset to zero. Subsequently, the processing advances to step S1903 to determine whether or not a value of rightward arrow-mark-selection-frequency counter is equal to or more than a preset value. When the value of rightward arrow-mark-selection-frequency counter is less than the preset value, the processing returns. When the value of rightward arrow-mark-selection-frequency counter is equal to or more than the preset value, the processing advances to step S1905 to determine whether or not present horizontal-direction selection cell number is maximum, i.e., whether or not the present selected item is in a right-end cell position. When the present selected item is not in the right-end cell position, the processing advances to step S1906 to increment a horizontal-direction selection cell number by one, then advances to step S1907. On the other hand, when the present selected item is in the right-end cell position, the processing skips the step S1906 and advances to the step S1907.

At the step S1907, the rightward arrow-mark-selection-frequency counter is reset to zero. Subsequently at step S1908, the scene is displayed again, and the processing returns.

Figure 29:
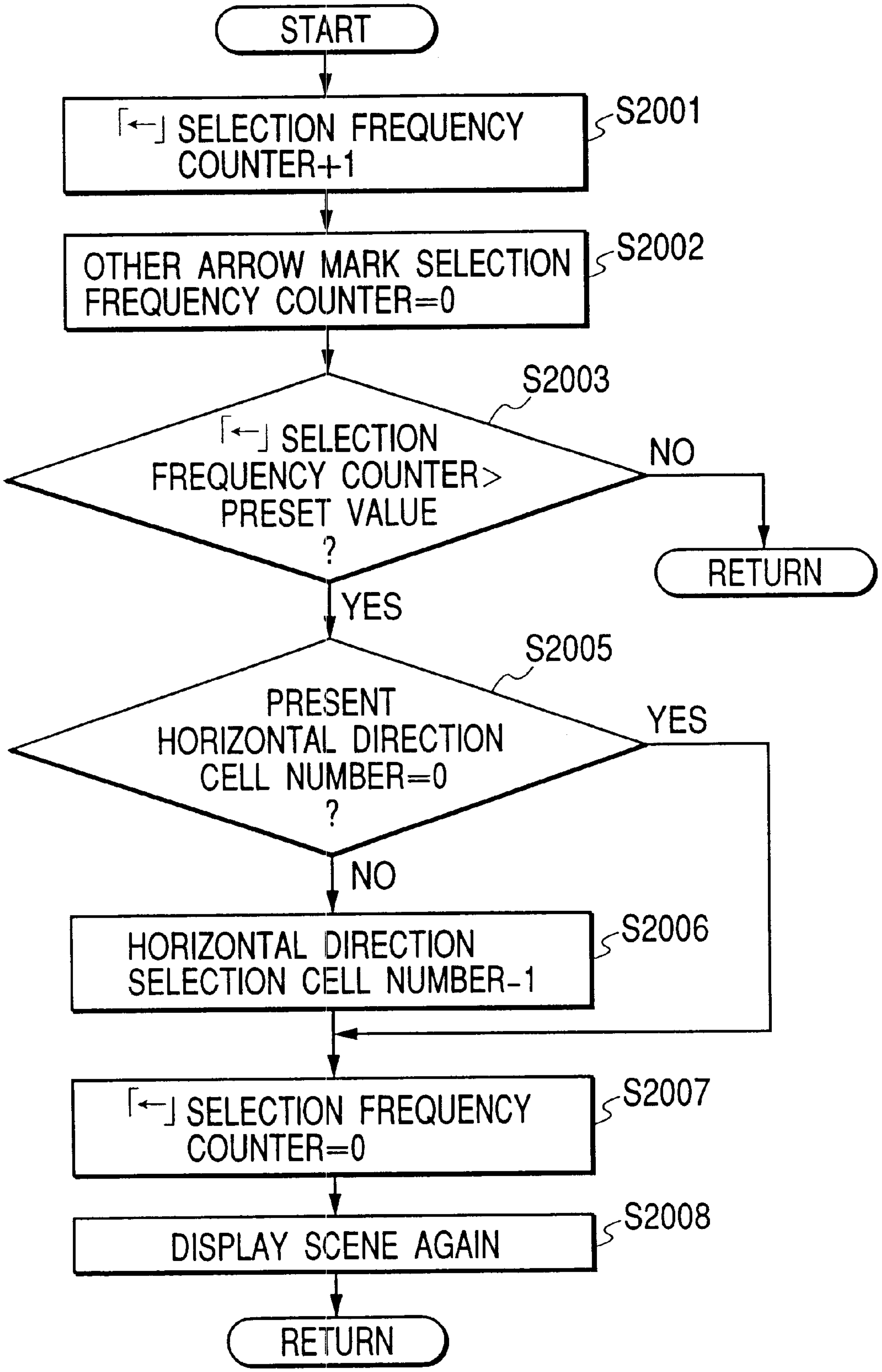
FIG. 29 is a flowchart of a leftward arrow-mark selection processing of step S1608 of FIG. 25.

The leftward arrow-mark selection processing will next be described with reference to FIG. 29. In the leftward arrow-mark selection processing, first at step S2001, a leftward arrow-mark-selection-frequency counter is incremented by one. Subsequently, at step S2002, other arrow-mark-selection-frequency counters are reset to zero. Subsequently, the processing advances to step S2003 to determine whether or not a value of leftward arrow-mark-selection-frequency counter is equal to or more than a preset value. When the value of leftward arrow-mark-selection-frequency counter is less than the preset value, the processing returns. When the value of leftward arrow-mark-selection-frequency counter is equal to or more than the preset value, the processing advances to step S2005 to determine whether or not present horizontal-direction selection cell number is zero, i.e., whether or not the present selected item is in a left-end cell position. When the present selected item is not in the left-end cell position, the processing advances to step S2006 to decrement the horizontal-direction selection cell number by one, then advances to step S2007. On the other hand, when the present selected item is in the left-end cell position, the processing skips the step S2006 and advances to the step S2007.

At the step S2007, the leftward arrow-mark-selection-frequency counter is reset to zero. Subsequently at step S2008, the scene is displayed again, and the processing returns.

Figure 30:
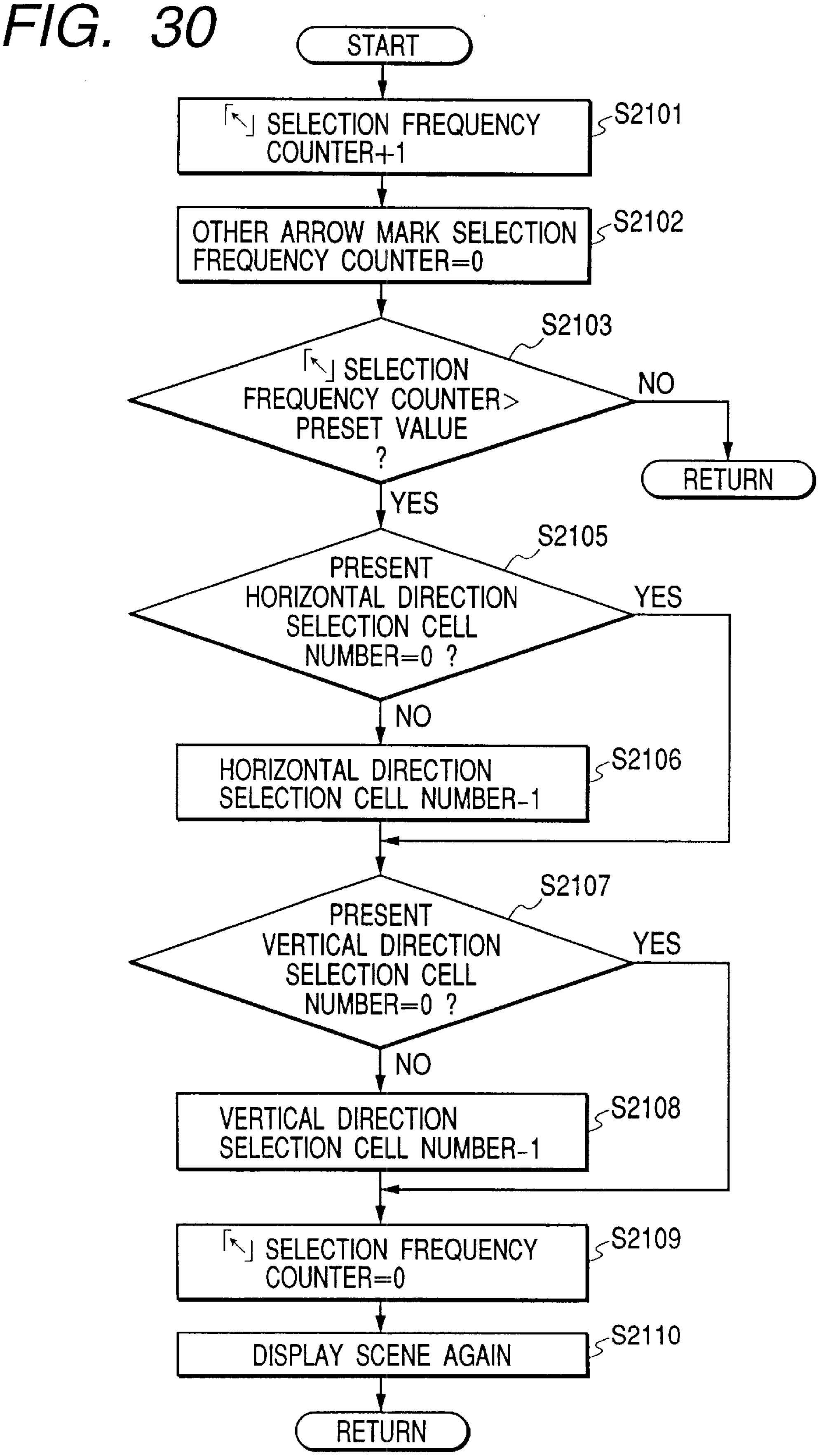
FIG. 30 is a flowchart of a left upward arrow-mark selection processing of step S1610 of FIG. 25.

The left upward arrow-mark selection processing will next be described with reference to FIG. 30. In the left upward arrow-mark selection processing, first at step S2101, a left upward arrow-mark-selection-frequency counter is incremented by one. Subsequently, at step S2102, other arrow-mark-selection-frequency counters are reset to zero. Subsequently, the processing advances to step S2103 to determine whether or not a value of left upward arrow-mark-selection-frequency counter is equal to or more than a preset value. When the value of left upward arrow-mark-selection-frequency counter is less than the preset value, the processing returns. When the value of left upward arrow-mark-selection-frequency counter is equal to or more than the preset value, the processing advances to step S2105 to determine whether or not the present horizontal-direction selection cell number is zero, i.e., whether or not the present selected item is in the left-end cell position. When the present selected item is not in the left-end cell position, the processing advances to step S2106 to decrement the horizontal-direction selection cell number by one, then advances to step S2107. On the other hand, when the present selected item is in the left-end cell position, the processing skips the step S2106 and advances to the step S2107.

At the step S2107, it is determined whether or not the present vertical-direction selection cell number is zero, i.e., whether or not the present selected item is in the uppermost cell position. When the present selected item is not in the uppermost cell position, the processing advances to step S2108 to decrement the vertical-direction selection cell number by one, then advances to step S2109. On the other hand, when the present selected item is in the uppermost cell position, the processing skips the step S2108 and advances to step S2109.

At the step S2109, the left upward arrow-mark-selection-frequency counter is reset to zero. Subsequently, at step S2110, the scene is displayed again, and the processing returns.

Figure 31:
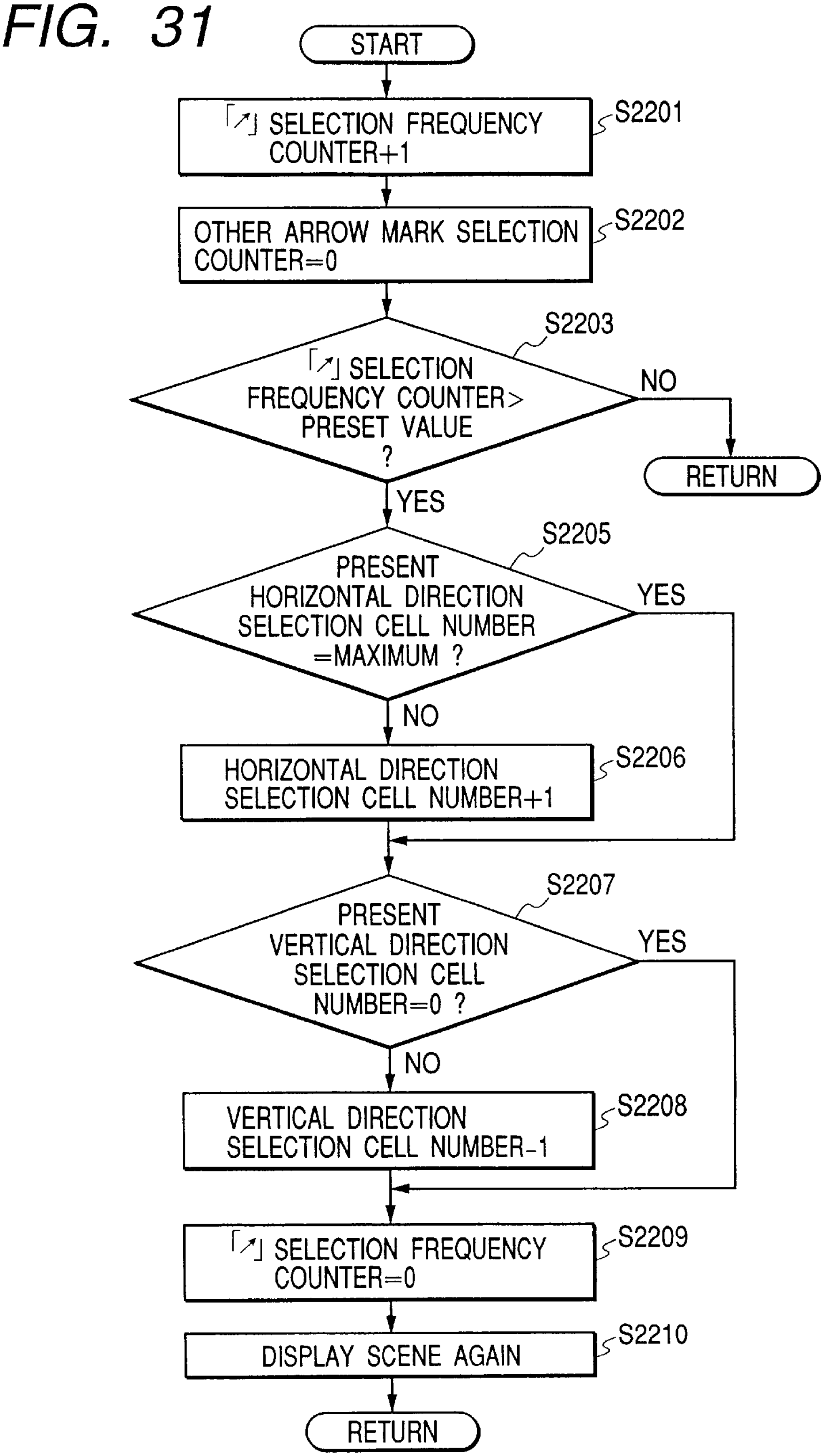
FIG. 31 is a flowchart of a right upward arrow-mark selection processing of step S1612 of FIG. 25.

The right upward arrow-mark selection processing will next be described with reference to FIG. 31. In the right upward arrow-mark selection processing, first at step S2201, a right upward arrow-mark-selection-frequency counter is incremented by one. Subsequently, at step S2202, other arrow-mark-selection-frequency counters are reset to zero. Subsequently, the processing advances to step S2203 to determine whether or not a value of right upward arrow-mark-selection-frequency counter is equal to or more than a preset value. When the value of right upward arrow-mark-selection-frequency counter is less than the preset value, the processing returns. When the value of right upward arrow-mark-selection-frequency counter is equal to or more than the preset value, the processing advances to step S2205 to determine whether or not the present horizontal-direction selection cell number is maximum, i.e., whether or not the present selected item is in the right-end cell position. When the present selected item is not in the right-end cell position, the processing advances to step S2206 to increment the horizontal-direction selection cell number by one, then advances to step S2207. On the other hand, when the present selected item is in the right-end cell position, the processing skips the step S2206 and advances to the step S2207.

At the step S2207, it is determined whether or not the present vertical-direction selection cell number is zero, i.e., whether or not the present selected item is in the uppermost cell position. When the present selected item is not in the uppermost cell position, the processing advances to step S2208 to decrement the vertical-direction selection cell number by one, then advances to step S2209. On the other hand, when the present selected item is in the uppermost cell position, the processing skips the step S2208 and advances to step S2209).

At the step S2209, the right upward arrow-mark-selection-frequency counter is reset to zero. Subsequently, at step S2210, the scene is displayed again, and the processing returns.

Figure 32:
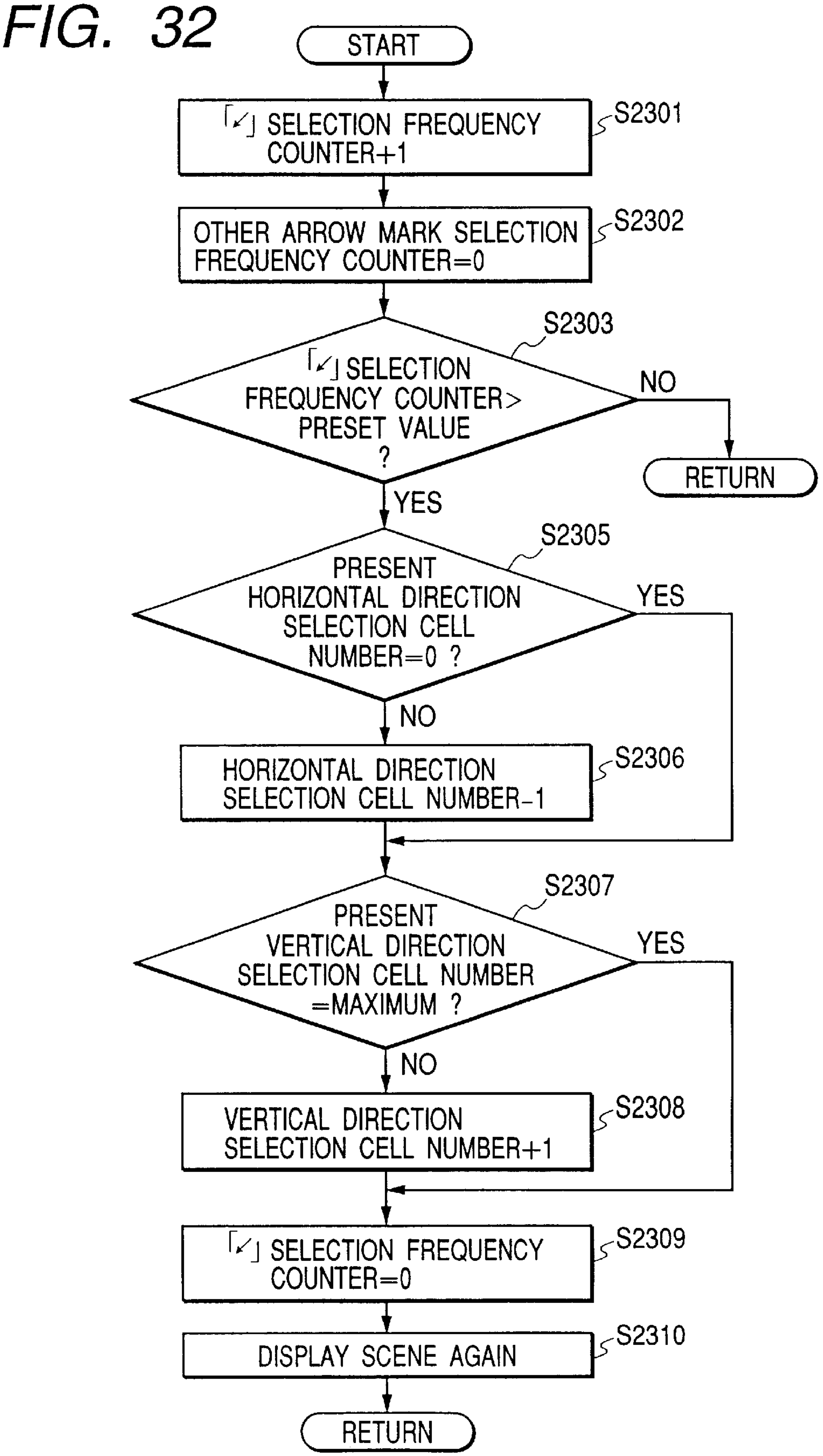
FIG. 32 is a flowchart of a left downward arrow-mark selection processing of step S1614 of FIG. 25.

The left downward arrow-mark selection processing will next be described with reference to FIG. 32. In the left downward arrow-mark selection processing, first at step S2301, a left downward arrow-mark-selection-frequency counter is incremented by one. Subsequently, at step S2302, other arrow-mark-selection-frequency counters are reset to zero. Subsequently, the processing advances to step S2303 to determine whether or not a value of left downward arrow-mark-selection-frequency counter is equal to or more than a preset value. When the value of left downward arrow-mark-selection-frequency counter is less than the preset value, the processing returns. When the value of left downward arrow-mark-selection-frequency counter is equal to or more than the preset value, the processing advances to step S2305 to determine whether or not the present horizontal-direction selection cell number is zero, i.e., whether or not the present selected item is in the left-end cell position. When the present selected item is not in the left-end cell position, the processing advances to step S2306 to decrement the horizontal-direction selection cell number by one, then advances to step S2307. On the other hand, when the present selected item is in the left-end cell position, the processing skips the step S2306 and advances to the step S2307.

At the step S2307, it is determined whether or not the present vertical-direction selection cell number is a maximum, i.e., whether or not the present selected item is in the lowermost cell position. When the present selected item is not in the lowermost cell position, the processing advances to step S2308 to increment the vertical direction selection cell number by one, then advances to step S2309. On the other hand, when the present selected item is in the lowermost cell position, the processing skips the step S2308 and advances to step S2309.

At the step S2309, the left downward arrow-mark selection frequency counter is reset to zero. Subsequently at step S2310, the scene is displayed again, and the processing returns.

Figure 33:
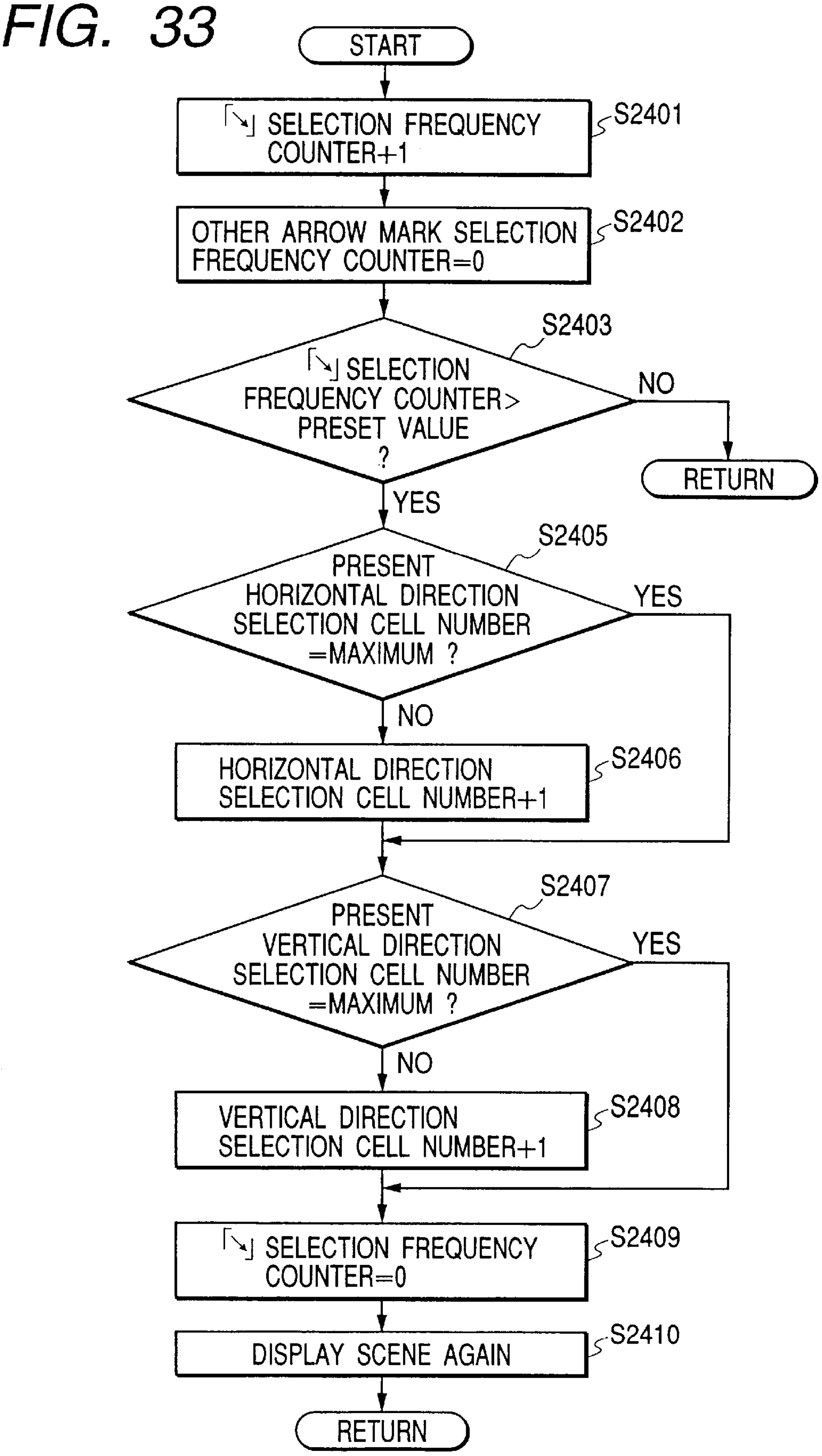
FIG. 33 is a flowchart of a right downward arrow-mark selection processing of step S1616 of FIG. 25.

The right downward arrow-mark selection processing will next be described with reference to FIG. 33. In the right downward arrow-mark selection processing, first at step S2401, a right downward arrow-mark-selection-frequency counter is incremented by one. Subsequently, at step S2402, other arrow-mark-selection-frequency counters are reset to zero. Subsequently, the processing advances to step S2403 to determine whether or not a value of right downward arrow-mark-selection-frequency counter is equal to or more than a preset value. When the value of right downward arrow-mark-selection-frequency counter is less than the preset value, the processing returns. When the value of right downward arrow-mark-selection-frequency counter is equal to or more than the preset value, the processing advances to step S2405 to determine whether or not the present horizontal-direction selection cell number is a maximum, i.e., whether or not the present selected item is in the right-end cell position. When the present selected item is not in the right-end cell position, the processing advances to step S2406 to increment the horizontal-direction selection cell number by one, then advances to step S2407. On the other hand, when the present selected item is in the right-end cell position, the processing skips the step S2406 and advances to the step S2407.

At the step S2407, it is determined whether or not the present vertical-direction selection cell number is a maximum, i.e., whether or not the present selected item is in the lowermost cell position. When the present selected item is not in the lowermost cell position, the processing advances to step S2408 to increment the vertical-direction selection cell number by one, then advances to step S2409. On the other hand, when the present selected item is in the lowermost cell position, the processing skips the step S2408 and advances to step S2409.

At the step S2409, the right downward arrow-mark-selection-frequency counter is reset to zero. Subsequently at step S2410, the scene is displayed again, and the processing returns.

As described above, in the embodiment, each of the arrow-mark keys of eight directions is selected by the visual-axis input, its selection frame is moved to the desired character or item position, and the visual-axis input satisfying the visual-axis input confirmation conditions is performed in the position, so that the character or the item present in the position is selected and inputted. Therefore, the predetermined input can securely and easily be performed, and an operation environment can be obtained to facilitate user's input operation.

(i) Ninth Embodiment

Figure 34:
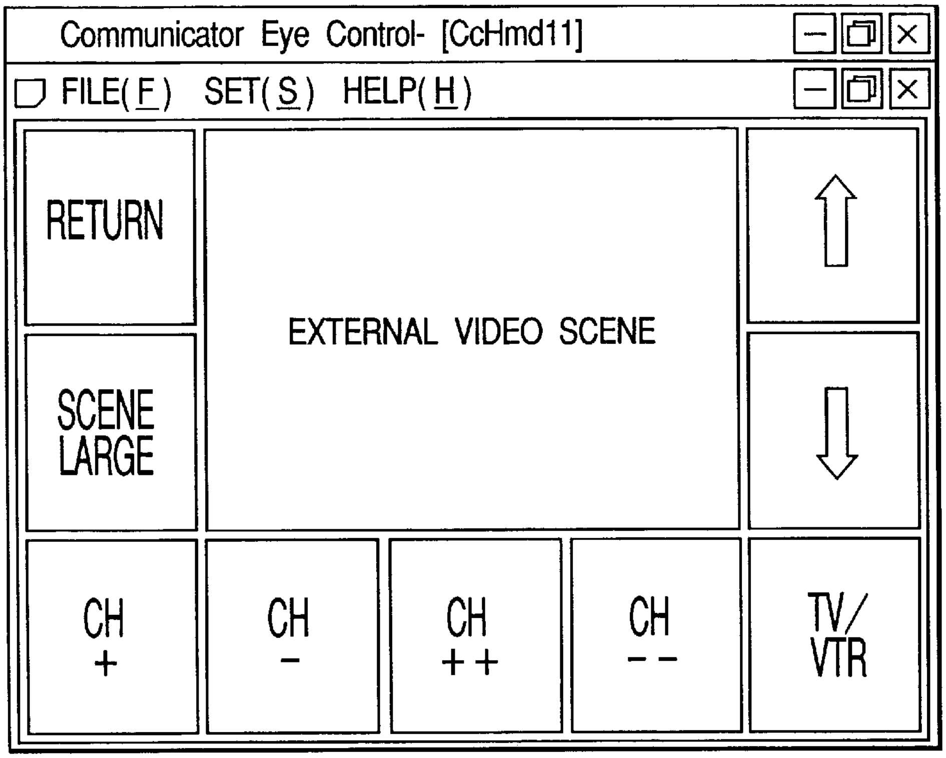
FIGS. 34 and 35 are views showing examples of a screen displayed in the head-mount display in the visual-axis input and decision-transfer device according to a ninth embodiment of the present invention.
Figure 35:
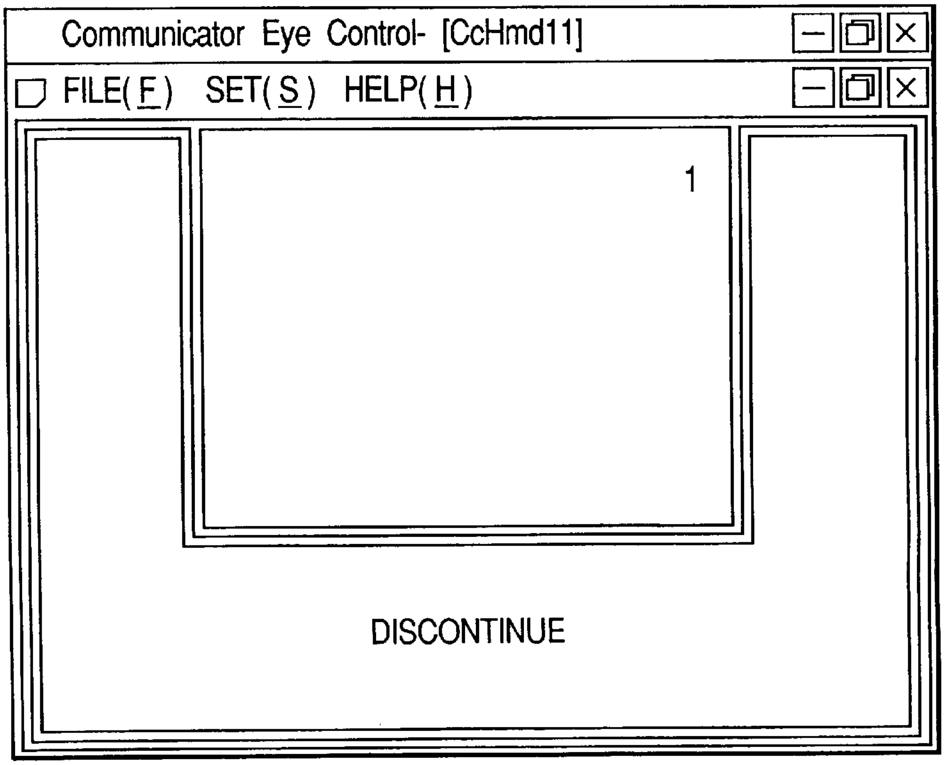
Figure 36:
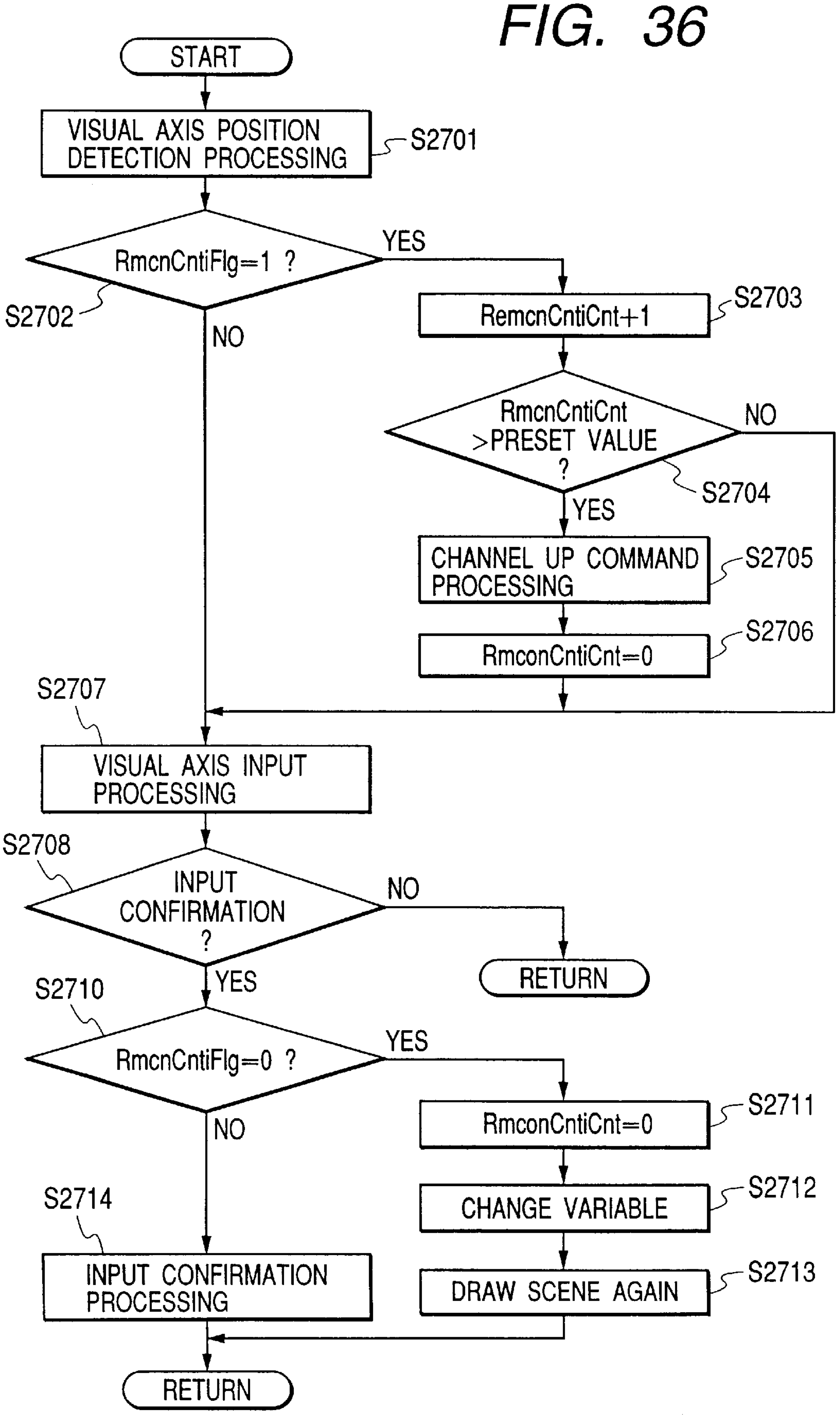
FIG. 36 is a flowchart showing a processing procedure in the visual-axis input and decision-transfer device according to the ninth embodiment of the present invention.

A ninth embodiment of the present invention will next be described with reference to FIGS. 34 to 36. FIGS. 34 and 35 are views showing examples of a selection screen displayed in the head-mount display, and FIG. 36 is a flowchart showing a processing procedure in the visual-axis input and decision-transfer device according to the ninth embodiment of the present invention.

In the embodiment, the PC 1008 comprises an interface to which an external device is connected in such a manner that the device can be controlled. Displayed in the head-mount display 1006 are selection items for continuously varying control amounts for the external device. When the selection item is selected by the visual-axis input, a command for continuously varying the control amount is generated in the PC 1008, and transmitted to the external device via the interface.

In the embodiment, for example, television is connected. Described is a case where video by television broadcasting and selection items for switching channels or adjusting the sound volume are displayed in the head-mount display 1006. The selection items include an item for instructing that channels be continuously switched one by one.

Specifically, as shown in FIG. 34, external video scene and selection items arranged in a periphery are displayed in the head-mount display 1006. Here, when an item CH++ for instructing that the channels be continuously switched one by one is selected by the visual axis input, the PC 1008 continuously transmits a channel switch command to switch the channels one by one to the television via the interface. Every time the channel switch command is received, the television switches the channels one by one. Moreover, the selection of CH++ switches the screen of the head-mount display 1006 to a screen in which an item for instructing where to stop the channels being continuously switched is displayed as shown in FIG. 35. When a user's desired channel is displayed in the switched screen, DISCONTINUE is selected by the visual-axis input. The PC 1008 stops outputting the channel switch command by the selection, so that the user can see the switched channel video.

The processing procedure will be described with reference to FIG. 36. First in step S2701, a visual-axis position detection processing is performed and, subsequently, it is determined at step S2702 whether or not a value of flag RmcnCntFlg indicating that the command is continuously transmitted to the television is one. When the value of flag RmcnCntFlg is one, it is judged that the command is continuously transmitted to the television, and the processing advances to step S2703 to increment by one a counter RmcnCntiCnt which serves as a timer for generating an output timing of the command. Subsequently, it is determined at step S2704 whether or not a value of counter RmcnCntiCnt exceeds a preset value. When the value of counter RmcnCntiCnt exceeds the preset value, the processing advances to step S2705 to perform a channel up command processing. Subsequently, after resetting the counter RmcnCntiCnt to zero at step S2706, the processing advances to step S2707. On the other hand, the value of counter RmcnCntiCnt does not exceed the preset value, the processing skips the steps S2705 and S2706, and advances to the step S2707.

At step S2707, a visual-axis input processing is performed and, subsequently, it is determined at step S2708 whether or not input is confirmed. When the input is not confirmed, the processing returns. On the other hand, in case of the input confirmation, the processing advances to step S2710 to determine whether or not the value of flag RmcnCntFlg is zero. When the value of flag RmcnCntFlg is zero, the processing advances to step S2711 to reset the counter RmcnCntiCnt to zero. Subsequently, at step S2712, a variable for setting the rate of display areas of external video and selection items displayed in the head-mount display 1006 is changed. After the scene is drawn again based on the changed variable at step S2713, the processing returns. On the other hand, when the value of flag RmcnCntFlg is not zero, the processing advances to step S2714 to perform an input confirmation processing, and returns.

When it is determined at the step S2702 that the value of flag RmcnCntFlg is not one, the processing advances to the step S2707. Thereafter, the processing is executed in the same manner as described above.

As described above, in the embodiment, the external device can be controlled by the visual-axis input in such a manner that the control amount can continuously be changed.

Additionally, in the embodiment, the case where the television channels are continuously switched has been described, but control may be performed to continuously vary the sound volume or other control amounts in the same manner.

(j) Tenth Embodiment

Figure 37:
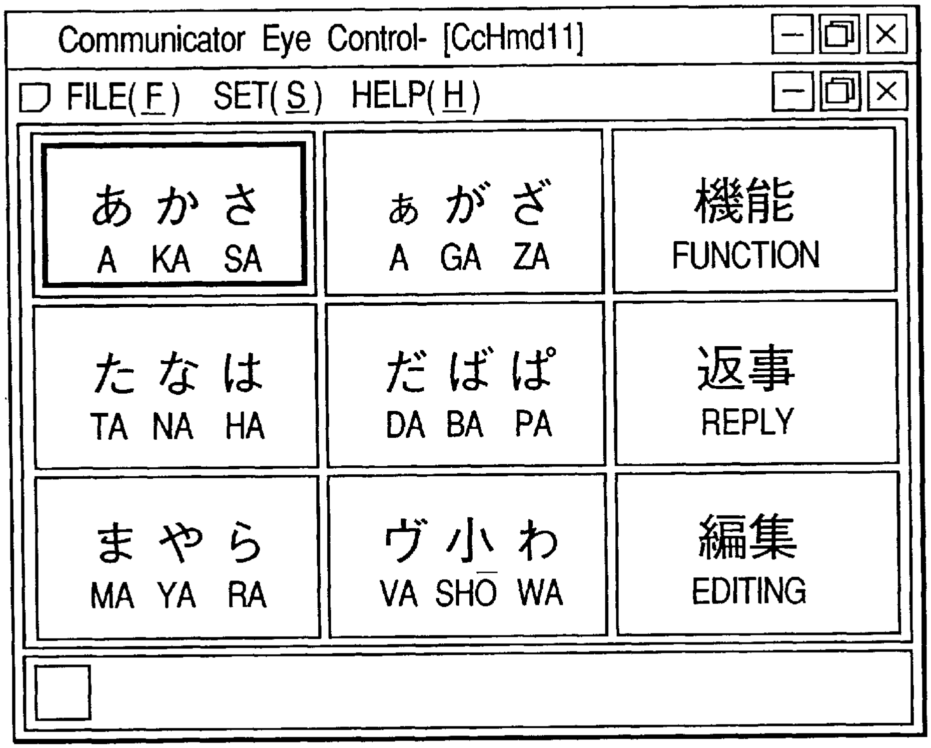
FIGS. 37 and 38 are views showing examples of a selection screen displayed in the head-mount display in the visual-axis input and decision-transfer device according to a tenth embodiment of the present invention.
Figure 38:
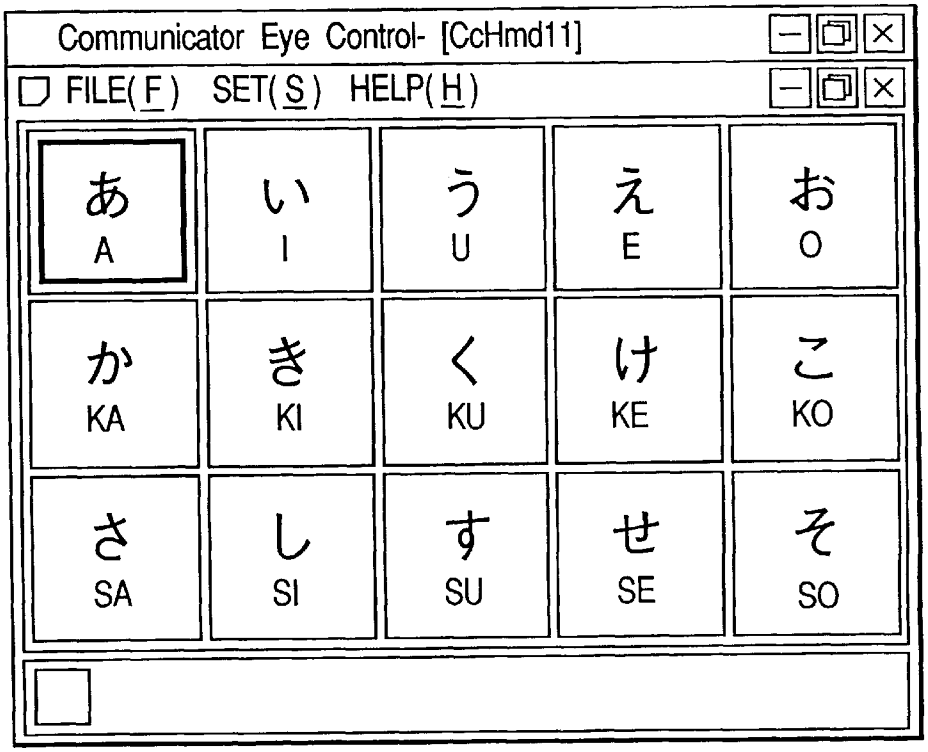

A tenth embodiment of the present invention will next be described with reference to FIGS. 37 and 38. FIGS. 37 and 38 are views showing examples of a selection screen displayed in the head-mount display in the visual-axis input and decision-transfer device according to the tenth embodiment of the present invention.

In the embodiment, control is performed in such a manner that selection items are hierarchically displayed in the head-mount display 1006, and the item to be inputted is confirmed by inputting the visual-axis while sequentially tracing selection items positioned subordinate to the selection item.

For example, in the embodiment, as shown in FIG. 37, selection items such as "AKASA", "TANAHA", and "MAYARA" are displayed as a first selection screen. Here, "AKASA" indicates an item for selecting hiragana or Japanese phonetic characters as a group of line A, KA, or SA in Japanese. Similarly, "TANAHA" indicates an item for selecting hiragana as a group of line TA, NA, or HA in Japanese, while "MAYARA" indicates an item for selecting hiragana as a group of line MA, YA, or RA in Japanese. Furthermore, FUNCTION is displayed for selecting a group of remote control function, a hiragana/katakana/English/numeric character mode switch function, a registration function, a fixed sentence call function, a function of changing various settings, and other functions.

For example, when "AKASA" is selected by the visual-axis input in the screen, the screen is switched to an individual selection screen shown in FIG. 38. In the individual selection screen, hiragana in lines A, KA, and SA are individually selected. For example, when hiragana "A" is selected and confirmed by the visual-axis input in the screen, "A" is inputted to a prepared sentence display section in a lower part of the screen.

When another item is selected in the first screen, the screen is similarly switched to the individual-selection screen to select each item from the grouped and included items. If the item selected in the individual-selection screen further includes grouped items, a selection screen is displayed by inputting the visual axis while tracing selection items positioned subordinate to the next selection item for selecting the grouped and included items.

It can arbitrarily be set what items are to be included and grouped into one item. In this case, the user designates the items to be grouped beforehand by his instructing operation, and a processing for hierarchically tracing the grouped items is performed.

As described above, in the embodiment, a plurality of items are grouped into one item, and the item is selected to select the plurality of included items. Subsequently, the corresponding item is selected from the plurality of items. The item to be inputted is selected and the input is confirmed by performing the visual-axis input while sequentially tracing the selection items positioned subordinate to the first selection item. Therefore, a large number of selection items do not need to be displayed once, and a larger display area can be secured for one item as compared with when a large number of selection items are displayed once. Moreover, the visual-axis position can easily be adjusted to the item to be selected, and generation of selection errors or the like can be reduced.

(k) Eleventh Embodiment

Figure 39:
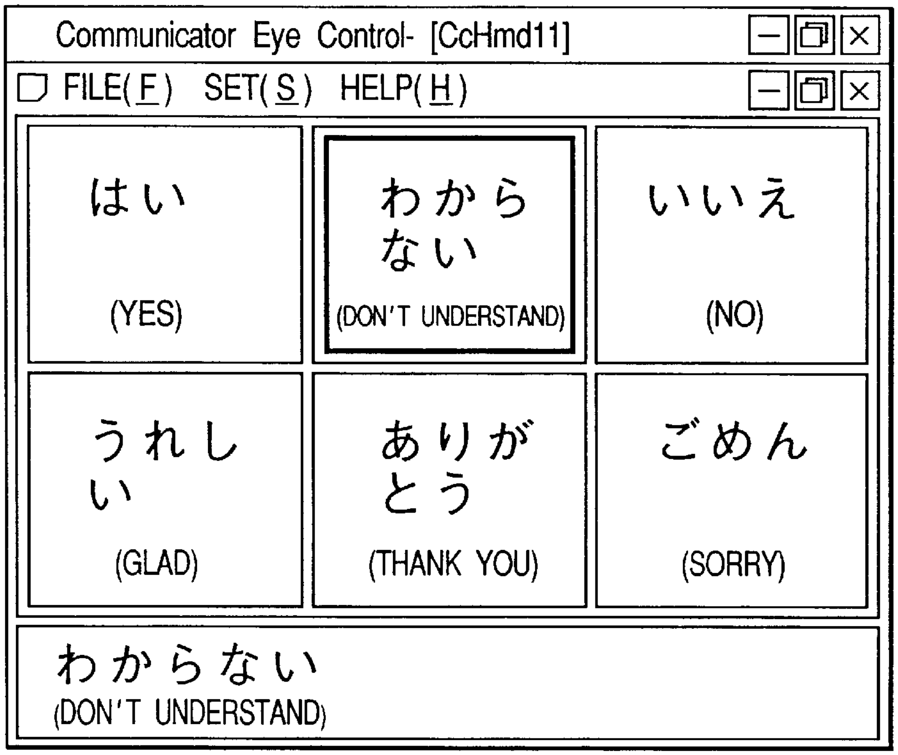
FIGS. 39 and 40 are views showing examples of a selection screen displayed in the head-mount display in the visual-axis input and decision-transfer device according to an eleventh embodiment of the present invention.
Figure 40:
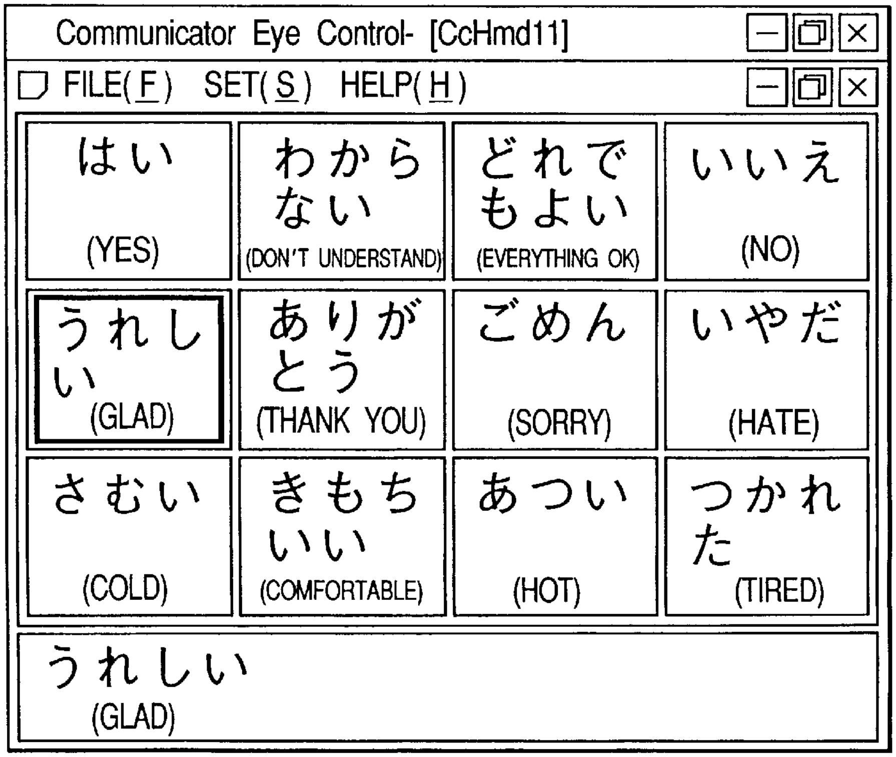

An eleventh embodiment of the present invention will next be described with reference to FIGS. 39 and 40. FIGS. 39 and 40 are views showing examples of a selection screen displayed in the head-mount display in the visual-axis input and decision-transfer device according to the eleventh embodiment of the present invention.

In the embodiment, a plurality of prepared words are selectably displayed in the head-mount display 1006, and there is provided a mode for selecting a desired word from the displayed words by the visual-axis input.

In the embodiment, for example, as shown in FIG. 39, phrases frequently used as ordinary responses such as YES, NO, THANK YOU, and the like are displayed, and YES, NO, or another response to a question or the like for the user can be selected by inputting the visual axis once. Therefore, the necessity of an operation for sequentially inputting characters to form YES is obviated, and a quick response can be made. Moreover, the screen can be used as a screen for practicing the visual-axis input.

Furthermore, as shown in FIG. 40, various responses can be made by displaying more phrases than the aforementioned screen.

As described above, according to the first to eleventh embodiments, for the detection result of a user's visual axis, the user is notified of the detection-result information indicating the visual-axis detection success or failure, blinking, selecting of the same choice, and the like. Therefore, the user can confirm the visual-axis detection result, and the possibility of user's repeating wasteful operations many times can be eliminated.

Moreover, the user can select whether or not the notification of detection result information be performed.

Furthermore, the user can be notified of the detection-result information by changing and displaying the background color, the character color, the selection frame color, or the like of the selection item included in the video on the display panel.

Additionally, the user can be notified of the detection-result information by the voice emitted from the sound emitting means.

Moreover, the user can be notified of the detection-result information by the light emitting state of the light-emitting means.

Furthermore, since the external video can be taken from the outside, and the external video and display panel are arranged and displayed in the video-observation means, the external video transmitted from the outside can be observed while looking at the display panel.

Additionally, since the video-observation means has one screen in which the display panel and external video can be arranged and displayed, and the rate of display areas of the display panel and external video in the screen of the video-observation means can arbitrarily be set based on the user's instruction, the user can observe the screen in the desired display state.

Moreover, when the external video is transmitted from the outside, and the transmitted external video is controlled to be displayed in the video-observation means, the selection item selected by the user's visual axis is controlled to be overlapped and displayed on the external video. Therefore, the selection item can be selected by the visual-axis input while seeing the external video transmitted from the outside.

Furthermore, it can be selected based on the user's instruction whether or not to overlap and display the selection item on the external video in the video-observation means.

Additionally, since the control is performed in such a manner that the display mode of the selection item on the display panel displayed by the video-observation means is changed and displayed based on the user's instruction, the selection item on the display panel can easily be visually recognized by the user.

Moreover, the background color of the selection item on the display panel can be changed and displayed based on the user's instruction.

Furthermore, the character color of the selection item on the display panel can be changed and displayed based on the user's instruction.

Additionally, the external device is connected via the connection means, and the control is performed to display the control item for the external device on the display panel. When receiving the input information for selecting the control item of the display panel whose control amount is continuously variable, the command to continuously vary the control amount is continuously transmitted to the external device via the connection means. Therefore, the external device can be controlled to continuously vary its control amount.

Moreover, the control is performed to hierarchically display the selection items in the display panel, and the selection items positioned subordinate to the first selection item are sequentially followed and selected to input the selection items according to the sequence of display, so that the mode of the user's confirming one decision to be transferred is executed. Therefore, the predetermined input can securely and easily be performed, and the operation environment for facilitating the user's input operation can be obtained.

Furthermore, the hierarchy of the selection items can be changed to an arbitrary hierarchy in accordance with the user's setting.

What is claimed is:

1. A visual axis input device comprising:

visual axis input means for detecting a visual axis of a user and inputting a visual axis detection result of the user's visual axis as input information for a display panel;

visual axis detection result notification means for notifying the user of detection result information indicating whether or not the visual axis detection is successful, in response to the visual axis detection result; and selection means for selecting whether or not to perform a notification of said detection result information by said visual axis detection result notification means.

2. The visual axis input device according to claim 1 wherein said visual axis detection result notification means notifies said user of said detection result information by changing and displaying a background color, character color, or selection frame color of the selection item included in a video of said display panel.

3. The visual axis input device according to claim 1 wherein said visual axis detection result notification means comprises sound emitting means for emitting a voice, and notifies said user of said detection result information by the voice emitted from the sound emitting means.

4. The visual axis input device according to claim 1 wherein said visual axis detection result notification means comprises light emitting means for emitting light, and notifies said user of said detection result information by a light emitting state of the light emitting means.

5. A visual axis input device which is provided with video observation means for displaying a display panel which can be observed by a user, visual axis detection means for detecting a visual axis of the user observing the display panel displayed by said video observation means, and visual axis input means for inputting a detection result of said user's visual axis by said visual axis detection means as input information for the display panel displayed in said video observation means, so that a decision of said user is transferred by the input information from said visual axis input means comprising: display control means for performing a control to arrange and display said display panel and an external video transmitted from outside in said video observation means.

6. The visual axis input device according to claim 5 wherein said video observation means comprises one screen in which said display panel and said external video can be arranged and displayed, and said display control means can set a rate of display areas of said display panel and said external video in the screen of said video observation means to an arbitrary rate based on a user's instruction.

7. A visual axis input device which is provided with video observation means for displaying video which can be observed by a user, visual axis detection means for detecting a visual axis of the user observing the video displayed by said video observation means, and visual axis input means for inputting a detection result of said user's visual axis by said visual axis detection means as input information for the video displayed in said video observation means, so that a decision of said user is transferred by the input information from said visual axis input means comprising: external video input means for inputting video from outside; and display control means for performing a control to display the external video transmitted via said external video input means in said video observation means, said display control means, when said external video is displayed in said video observation means, being able to overlap and display a choice selected by said user's visual axis on the external video.

8. The visual axis input device according to claim 7 further comprising selection means for selecting whether or not to overlap and display said choice on said external video in said video observation means based on an instruction of said user.

9. A visual axis input device which is provided with video observation means for displaying a display panel including selection items which can be observed by a user, visual axis detection means for detecting a visual axis of the user observing the display panel displayed by said video observation means, and visual axis input means for inputting a detection result of said user's visual axis by said visual axis detection means as input information for said display panel, so that a decision of said user is transferred by the input information from said visual axis input means comprising: display control means for performing a control to change and display a display mode of the selection items on said display panel displayed by said video observation means based on an instruction of said user.

10. The visual axis input device according to claim 9 wherein said display control means changes and displays a background color of the selection item on said display panel based on said user's instruction.

11. The visual axis input device according to claim 9 wherein said display control means changes and displays a character color of the selection item on said display panel based on said user's instruction.

12. A visual axis input device which is provided with visual axis input means for detecting a visual axis of a user facing a display panel, and inputting a detection result of the user's visual axis as input information for said display panel to transfer a decision of said user by the input information from said visual axis input means, comprising: connection means for connecting an external device; display control means for performing a control to display control items for said external device on said display panel; and output means for, when the input information is transmitted from said visual axis input means to select an item for continuously varying a control amount from the control items of said display panel, continuously transmitting a command to continuously vary said control amount to said external device via said connection means.

13. A visual axis input device which is provided with visual axis input means for detecting a visual axis of a user facing a display panel, and inputting a detection result of the user's visual axis as input information for said display panel to transfer a decision of said user by the input information from the visual axis input means, comprising: display control means for performing a control to hierarchically display selection items on said display panel, so that a mode of confirming one decision of said user to transfer can be executed by sequentially following and selecting selection items positioned subordinate to said selection items to input said input information according to a sequence of display of said selection items via said visual axis input means.

14. The visual axis input device according to claim 13 wherein a hierarchy of said selection items can be changed to an arbitrary hierarchy by a setting of said user.

15. A visual axis input method comprising:

a visual axis detecting step for detecting a visual axis of a user;

an inputting step for inputting a visual axis detection result of said visual axis detecting step as input information for a display panel;

a notifying step of notifying the user of detection result information indicating whether or not the visual axis detection is successful, in response to the visual axis detection result; and a selection step for selecting whether or not to perform a notification of said detection result information by said notifying step.

16. The visual axis input method according to claim 15 wherein said notifying step notifies the user of said detection result information by changing and displaying a background color, character color, or selection frame color of a selection item included in a video of said display panel.

17. The visual axis input method according to claim 15 wherein said notifying step notifies the user of said detection result information by a voice emitted from sound emitting means.

18. The visual axis input method according to claim 15 wherein said notifying step notifies the user of said detection result information by a light emitting state of light emitting means.

19. A visual axis input method for displaying a display panel which can be observed by a user by video observation means, detecting a visual axis of the user observing the display panel displayed by said video observation means, and inputting a detection result of said user's visual axis as input information for the display panel displayed by said video observation means to transfer a decision of said user, wherein an external video is taken from outside, and the external video and said display panel can be arranged and displayed in said video observation means.

20. The visual axis input method according to claim 19 wherein said video observation means comprises one screen in which said display panel and said external video can be arranged and displayed, and a rate of display areas of said display panel and said external video in the screen of said video observation means can be set to an arbitrary rate based on a user's instruction.

21. A visual axis input method for displaying a video which can be observed by a user by video observation means, detecting a visual axis of the user observing the video displayed by said video observation means, and inputting a detection result of said user's visual axis as input information for the video displayed by said video observation means to transfer a decision of said user, comprising steps of: inputting an external video from outside, and performing a control to display the inputted external video in said video observation means; and, when said external video is displayed in said video observation means, performing a control to overlap and display a choice selected by said user's visual axis on the external video.

22. The visual axis input method according to claim 21 further comprising a step of selecting whether or not to overlap and display said choice on said external video in said video observation means based on an instruction of said user.

23. A visual axis input method for displaying a display panel including selection items which can be observed by a user by video observation means, detecting a visual axis of the user observing the display panel displayed by said video observation means, and inputting a detection result of said user's visual axis as input information for said display panel to transfer a decision of said user, wherein a display mode of the selection items on said display panel displayed by said video observation means is changed and displayed based on an instruction of said user.

24. The visual axis input method according to claim 23 wherein a background color of the selection item on said display panel is changed and displayed based on said user's instruction.

25. The visual axis input method according to claim 23 wherein a character color of the selection item on said display panel is changed and displayed based on said user's instruction.

26. A visual axis input method for detecting a visual axis of a user facing a display panel, and inputting a detection result of the user's visual axis as input information for said display panel to transfer a decision of said user, comprising steps of: connecting an external device via connection means; performing a control to display control items for said external device on said display panel; and, when the input information is transmitted to select an item for continuously varying a control amount from the control items of said display panel, continuously transmitting a command to continuously vary said control amount to said external device via said connection means.

27. A visual axis input method for detecting a visual axis of a user facing a display panel, and inputting a detection result of the user's visual axis as input information for said display panel to transfer a decision of said user by the input information, comprising steps of: performing a control to hierarchically display selection items on said display panel; and executing a mode of confirming one decision of said user to transfer by sequentially following and selecting selection items positioned subordinate to said selection items to input said input information according to a sequence of display of said selection items.

28. The visual axis input method according to claim 27 wherein a hierarchy of said selection items can be changed to an arbitrary hierarchy by a setting of said user.

29. A memory medium for storing a program for controlling a visual axis input device for detecting a visual axis of a user and inputting a visual axis detection result of the user's visual axis as input information for a display panel, wherein said program comprises:

a visual axis detection result notification module instructing said visual axis input device to notify the user of detection result information indicating whether or not the visual axis detection is successful, in response to the visual axis detection result; and a selection module for instructing said visual axis input device to select whether or not to perform a notification of the detection result information by said visual axis detection result notification module.

30. The memory medium according to claim 29 wherein said visual axis detection result notification module notifies said user of said detection result information by changing and displaying a background color, character color, or selection frame color of a selection item included in a video of said display panel.

31. The memory medium according to claim 29 wherein said visual axis detection result notification module comprises a module for controlling sound emitting means for emitting a voice, and notifies said user of said detection result information by the voice emitted by said sound emitting means.

32. The memory medium according to claim 29 wherein said visual axis detection result notification module comprises a module for controlling light emitting means for emitting light, and notifies said user of said detection result information by a light emitting state of the light emitting means.

33. A memory medium for displaying a display panel including choices which can be observed by a user by video observation means, detecting a visual axis of the user observing the display panel displayed in said video observation means by visual axis detection means, and inputting a detection result of said user's visual axis by said visual axis detection means as input information for the display panel displayed in said video observation means by visual axis input means to store a program for constructing a visual axis input system for transferring a decision of said user, wherein said program comprises a display control module for performing a control to arrange and display said display panel and an external video transmitted from outside in said video observation means.

34. The memory medium according to claim 33 wherein said video observation means comprises one screen in which said display panel and said external video can be arranged and displayed, and said display control module can set a rate of display areas of said display panel and said external video in the screen of said video observation means to an arbitrary rate based on a user's instruction.

35. A memory medium for displaying a video which can be observed by a user by video observation means, detecting a visual axis of the user observing the video displayed in said video observation means by visual axis detection means, and inputting a detection result of said user's visual axis by said visual axis detection means as input information for the video displayed in said video observation means by visual axis input means to store a program for constructing a visual axis input system for transferring a decision of said user, wherein said program comprises an external video input module for inputting the video from outside, and a display control module for performing a control to display said external video transmitted via said external video input module in said video observation means, and when said external video is displayed in said video observation means, said display control module can overlap and display a choice selected by said user's visual axis on the external video.

36. The memory medium according to claim 35 wherein said program further comprises selection module means for selecting whether or not to overlap and display said choice on said external video in said video observation means based on an instruction of said user.

37. A memory medium for displaying a display panel including selection items which can be observed by a user by video observation means, detecting a visual axis of the user observing the display panel displayed in said video observation means by visual axis detection means, and inputting a detection result of said user's visual axis by said visual axis detection means as input information for said display panel by visual axis input means to store a program for constructing a visual axis input system for transferring a decision of said user, wherein said program comprises a display control module for performing a control to change and display a display mode of the selection items on said display panel displayed by said video observation means based on an instruction of said user.

38. The memory medium according to claim 37 wherein said display control module changes and displays a background color of the selection item on said display panel based on said user's instruction.

39. The memory medium according to claim 37 wherein said display control module changes and displays a character color of the selection item on said display panel based on said user's instruction.

40. A memory medium which uses a visual axis input device for detecting a visual axis of a user facing a display panel, and inputting a detection result of the user's visual axis as input information for said display panel to store a program for constructing a visual axis input system for transferring a decision of said user by the input information from said visual axis input device, wherein said program comprises a display control module for performing a control to display control items for an external device connected via connection means in said display panel, and an output module for, when the input information is transmitted from said visual axis input means to select an item for continuously varying a control amount from the control items of said display panel, continuously transmitting a command to continuously vary said control amount to said external device via said connection means.

41. A memory medium which uses a visual axis input device for detecting a visual axis of a user facing a display panel, and inputting a detection result of the user's visual axis as input information for said display panel to store a program for constructing a visual axis input system for transferring a decision of said user by the input information from the visual axis input device, wherein said program comprises a display control module for performing a control to hierarchically display selection items in said display panel, and a mode execution module for executing a mode of confirming one decision of said user to transfer by sequentially following and selecting selection items positioned subordinate to said selection items to input said input information according to a sequence of display of said selection items via said visual axis input means.

42. The memory medium according to claim 41 wherein a hierarchy of said selection items can be changed to an arbitrary hierarchy by a setting of said user.

* * * * *

UNITED STATES PATENT AND TRADEMARK OFFICE

CERTIFICATE OF CORRECTION

PATENT NO. : 6,161,932
DATED : December 19, 2000
INVENTOR(S) : Hironori Goto, et al.

It is certified that error appears in the above-identified patent and that said Letters Patent is hereby corrected as shown below:

Column 5,
Line 3, "screen a" should read -- a screen --.

Column 6,
Line 47, "*xh= (xd+xe) /2x0= (xd+xe) /2+δx*" should read -- xh= (xd+xe) /2
xO= (xd+xe) /2+δx --.

Signed and Sealed this

Thirteenth Day of November, 2001

*Attest:*

NICHOLAS P. GODICI

*Attesting Officer*

*Acting Director of the United States Patent and Trademark Office*

UNITED STATES PATENT AND TRADEMARK OFFICE

CERTIFICATE OF CORRECTION

PATENT NO. : 6,161,932 
DATED : December 19, 2000
INVENTOR(S) : Hironori Goto et al.

It is certified that error appears in the above-identified patent and that said Letters Patent is hereby corrected as shown below:

Column 5,
Line 3, "screen a" should read -- a screen --.

Column 6,
Line 47, "*xh= (xd+xe) /2x0= (xd+xe) /2+δx*" should read -- xh= (xd+xe) /2xO= (xd+xe) /2+δx --.

Signed and Sealed this

Twenty-sixth Day of October, 2004

JON W. DUDAS
*Director of the United States Patent and Trademark Office*